US009456755B2

(12) United States Patent
Soykan et al.

(10) Patent No.: US 9,456,755 B2
(45) Date of Patent: Oct. 4, 2016

(54) METHOD AND DEVICE TO MONITOR PATIENTS WITH KIDNEY DISEASE

(75) Inventors: Orhan Soykan, Shoreview, MN (US); VenKatesh R. Manda, Stillwater, MN (US); Martin T. Gerber, Maple Grove, MN (US); Christopher M. Hobot, Tonka Bay, MN (US)

(73) Assignee: Medtronic, Inc., Minneapolis, MN (US)

( * ) Notice: Subject to any disclaimer, the term of this patent is extended or adjusted under 35 U.S.C. 154(b) by 1204 days.

(21) Appl. No.: 13/451,461

(22) Filed: Apr. 19, 2012

(65) Prior Publication Data
US 2012/0277546 A1    Nov. 1, 2012

Related U.S. Application Data

(63) Continuation-in-part of application No. 13/424,525, filed on Mar. 20, 2012, and a continuation-in-part of application No. 13/424,429, filed on Mar. 20, 2012, and a continuation-in-part of application No. 13/424,479, filed on Mar. 20, 2012.

(Continued)

(51) Int. Cl.
*A61B 5/0205* (2006.01)
*A61B 5/0402* (2006.01)
(Continued)

(52) U.S. Cl.
CPC ......... *A61B 5/0205* (2013.01); *A61B 5/0402* (2013.01); *A61B 5/0452* (2013.01); *A61B 5/145* (2013.01); *A61M 1/14* (2013.01); *A61M 1/1601* (2014.02)

(58) Field of Classification Search
CPC .............. A61B 5/0452; A61B 5/0402; A61B 5/14503; A61B 5/7275
See application file for complete search history.

(56) References Cited

U.S. PATENT DOCUMENTS

| 3,602,222 A | * | 8/1971 | Herndon ............ A61B 5/0456 324/76.39 |
| 3,608,729 A | | 9/1971 | Haselden |

(Continued)

FOREIGN PATENT DOCUMENTS

| EP | 266795 A2 | 11/1987 |
| EP | 1364666 A1 | 11/2003 |

(Continued)

OTHER PUBLICATIONS

Gordhandas et al, Real-Time Extraction and Analysis of Key Morphological Features in the Electrocardiogram, for Data Compression and Clinical Decision Support, 2004, Computational Physiology, pp. 15-18.*

(Continued)

*Primary Examiner* — Jacqueline Cheng
*Assistant Examiner* — Angeline Premraj
(74) *Attorney, Agent, or Firm* — Hahn & Associates PLLC; Roger C. Hahn; Kenneth J. Collier

(57) ABSTRACT

A medical monitoring device for monitoring electrical signals from the body of a subject is described. The medical monitoring device monitors electrical signals originating from a cardiac cycle of the subject and associates each cardiac cycle with a time index. The medical monitoring device applies a forward computational procedure to generate a risk score indicative of hyperkalemia, hypokalemia or arrhythmia of the subject. The medical monitoring device can adjust the forward computational procedure based upon clinical data obtained from the subject.

25 Claims, 27 Drawing Sheets

Related U.S. Application Data

(60) Provisional application No. 61/480,544, filed on Apr. 29, 2011, provisional application No. 61/480,532, filed on Apr. 29, 2011.

(51) Int. Cl.

| | |
|---|---|
| *A61B 5/0452* | (2006.01) |
| *A61B 5/145* | (2006.01) |
| *A61M 1/14* | (2006.01) |
| *A61M 1/16* | (2006.01) |

(56) References Cited

U.S. PATENT DOCUMENTS

| | | | |
|---|---|---|---|
| 3,669,878 A | 6/1972 | Marantz | |
| 3,669,880 A | 6/1972 | Marantz | |
| 3,850,835 A | 11/1974 | Marantz | |
| 3,884,808 A | 5/1975 | Scott | |
| 3,989,622 A | 11/1976 | Marantz | |
| 4,060,485 A | 11/1977 | Eaton | |
| 4,371,385 A | 2/1983 | Johnson | |
| 4,374,382 A | 2/1983 | Markowitz | |
| 4,381,999 A | 5/1983 | Boucher | |
| 4,460,555 A | 7/1984 | Thompson | |
| 4,556,063 A | 12/1985 | Thompson et al. | |
| 4,562,751 A | 1/1986 | Nason | |
| 4,581,141 A | 4/1986 | Ash | |
| 4,650,587 A | 3/1987 | Polak | |
| 4,678,408 A | 7/1987 | Mason | |
| 4,685,903 A | 8/1987 | Cable | |
| 4,750,494 A | 6/1988 | King et al. | |
| 4,799,493 A * | 1/1989 | DuFault | A61N 1/3956 600/518 |
| 4,826,663 A | 5/1989 | Alberti | |
| 4,828,693 A | 5/1989 | Lindsay | |
| 5,080,653 A | 1/1992 | Voss | |
| 5,092,886 A | 3/1992 | Dobos-Hardy | |
| 5,097,122 A | 3/1992 | Coiman | |
| 5,127,404 A | 7/1992 | Wyborny et al. | |
| 5,284,470 A | 2/1994 | Beltz | |
| 5,302,288 A | 4/1994 | Meidl | |
| 5,305,745 A | 4/1994 | Zacouto et al. | |
| 5,318,750 A | 6/1994 | Lascombes | |
| 5,468,388 A | 11/1995 | Goddard | |
| 5,683,432 A | 11/1997 | Goedeke et al. | |
| 5,762,782 A | 6/1998 | Kenley | |
| 5,819,007 A * | 10/1998 | Elghazzawi | A61B 5/0452 600/515 |
| 5,944,684 A | 8/1999 | Roberts | |
| 6,048,732 A | 4/2000 | Anslyn | |
| 6,052,622 A | 4/2000 | Holstrom | |
| 6,058,331 A | 5/2000 | King | |
| 6,230,059 B1 | 5/2001 | Duffin | |
| 6,248,093 B1 | 6/2001 | Moberg | |
| 6,254,567 B1 | 7/2001 | Treu | |
| 6,321,101 B1 | 11/2001 | Holstrom | |
| 6,362,591 B1 | 3/2002 | Moberg | |
| 6,363,279 B1 | 3/2002 | Ben-Haim et al. | |
| 6,554,798 B1 | 4/2003 | Mann | |
| 6,555,986 B2 | 4/2003 | Moberg | |
| 6,589,229 B1 | 7/2003 | Connelly | |
| 6,602,399 B1 | 8/2003 | Fromherz et al. | |
| 6,609,023 B1 * | 8/2003 | Fischell | A61B 5/0031 600/515 |
| 6,627,164 B1 | 9/2003 | Wong | |
| 6,676,608 B1 | 1/2004 | Keren | |
| 6,711,439 B1 | 3/2004 | Bradley et al. | |
| 6,818,196 B2 | 11/2004 | Wong | |
| 6,878,283 B2 | 4/2005 | Thompson | |
| 6,960,179 B2 | 11/2005 | Gura | |
| 7,077,819 B1 | 7/2006 | Goldau et al. | |
| 7,208,092 B2 | 4/2007 | Micheli | |
| 7,276,042 B2 | 10/2007 | Polaschegg | |
| 7,404,799 B1 * | 7/2008 | Koh | A61B 5/0816 600/483 |
| 7,566,432 B2 | 7/2009 | Wong | |
| 7,575,564 B2 | 8/2009 | Childers | |
| 7,610,086 B1 * | 10/2009 | Ke | A61B 5/0452 600/517 |
| 7,674,231 B2 | 3/2010 | McCombie | |
| 7,704,361 B2 | 4/2010 | Garde | |
| 7,736,507 B2 | 6/2010 | Wong | |
| 7,754,852 B2 | 7/2010 | Burnett | |
| 7,756,572 B1 | 7/2010 | Fard | |
| 7,776,210 B2 | 8/2010 | Rosenbaum | |
| 7,794,141 B2 | 9/2010 | Perry | |
| 7,850,635 B2 | 12/2010 | Polaschegg | |
| 7,867,214 B2 | 1/2011 | Childers | |
| 7,922,686 B2 | 4/2011 | Childers | |
| 7,922,911 B2 | 4/2011 | Micheli | |
| 7,947,179 B2 | 5/2011 | Rosenbaum | |
| 7,967,022 B2 | 6/2011 | Grant | |
| 7,981,082 B2 | 7/2011 | Wang | |
| 8,034,161 B2 | 10/2011 | Gura | |
| 8,070,709 B2 | 12/2011 | Childers | |
| 8,096,969 B2 | 1/2012 | Roberts | |
| 8,183,046 B2 | 5/2012 | Lu | |
| 8,187,250 B2 | 5/2012 | Roberts | |
| 8,246,826 B2 | 8/2012 | Wilt | |
| 8,273,049 B2 | 9/2012 | Demers | |
| 8,292,594 B2 | 10/2012 | Tracey | |
| 8,313,642 B2 | 11/2012 | Yu | |
| 8,317,492 B2 | 11/2012 | Demers | |
| 8,357,113 B2 | 1/2013 | Childers | |
| 8,366,316 B2 | 2/2013 | Kamen | |
| 8,366,655 B2 | 2/2013 | Kamen | |
| 1,383,728 A1 | 3/2013 | Pudil | |
| 8,409,441 B2 | 4/2013 | Wilt | |
| 8,499,780 B2 | 8/2013 | Wilt | |
| 8,518,260 B2 | 8/2013 | Raimann | |
| 8,535,525 B2 | 9/2013 | Heyes | |
| 8,580,112 B2 | 11/2013 | Updyke | |
| 8,597,227 B2 | 12/2013 | Childers | |
| 8,696,626 B2 | 4/2014 | Kirsch | |
| 2002/0042561 A1 | 4/2002 | Schulman | |
| 2002/0112609 A1 | 8/2002 | Wong | |
| 2003/0080059 A1 | 5/2003 | Peterson | |
| 2003/0097086 A1 | 5/2003 | Gura | |
| 2003/0105435 A1 | 6/2003 | Taylor | |
| 2003/0114787 A1 | 6/2003 | Gura | |
| 2004/0019312 A1 | 1/2004 | Childers | |
| 2004/0099593 A1 | 5/2004 | DePaolis | |
| 2004/0147900 A1 | 7/2004 | Polaschegg | |
| 2004/0215090 A1 | 10/2004 | Erkkila | |
| 2005/0065760 A1 | 3/2005 | Murtfeldt | |
| 2005/0113796 A1 | 5/2005 | Taylor | |
| 2005/0126961 A1 | 6/2005 | Bissler | |
| 2005/0126998 A1 | 6/2005 | Childers | |
| 2005/0150832 A1 | 7/2005 | Tsukamoto | |
| 2005/0234357 A1 * | 10/2005 | Xue | A61B 5/04525 600/510 |
| 2005/0234381 A1 | 10/2005 | Niemetz | |
| 2005/0236330 A1 | 10/2005 | Nier et al. | |
| 2005/0274658 A1 | 12/2005 | Rosenbaum | |
| 2006/0025661 A1 | 2/2006 | Sweeney | |
| 2006/0195064 A1 | 8/2006 | Plahey | |
| 2006/0217771 A1 | 9/2006 | Soykan et al. | |
| 2006/0226079 A1 | 10/2006 | Mori | |
| 2006/0241709 A1 | 10/2006 | Soykan | |
| 2006/0247548 A1 * | 11/2006 | Sarkar | A61B 5/0464 600/515 |
| 2006/0264894 A1 | 11/2006 | Moberg | |
| 2007/0007208 A1 | 1/2007 | Brugger | |
| 2007/0038138 A1 * | 2/2007 | Gill | A61B 5/0452 600/513 |
| 2007/0066928 A1 | 3/2007 | Lannoy | |
| 2007/0138011 A1 | 6/2007 | Hofmann | |
| 2007/0175827 A1 | 8/2007 | Wariar | |
| 2007/0179431 A1 | 8/2007 | Roberts | |
| 2007/0215545 A1 | 9/2007 | Bissler | |
| 2007/0255250 A1 | 11/2007 | Moberg | |
| 2008/0006570 A1 | 1/2008 | Gura | |

(56) References Cited

U.S. PATENT DOCUMENTS

| | | |
|---|---|---|
| 2008/0021337 A1 | 1/2008 | Li et al. |
| 2008/0053905 A9 | 3/2008 | Brugger |
| 2008/0067132 A1 | 3/2008 | Ross |
| 2008/0215247 A1 | 9/2008 | Tonelli |
| 2009/0020471 A1 | 1/2009 | Tsukamoto |
| 2009/0101577 A1 | 4/2009 | Fulkerson |
| 2009/0124869 A1* | 5/2009 | Hu ................. A61B 5/0476 600/301 |
| 2009/0127193 A1 | 5/2009 | Updyke |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2010/0004588 A1 | 1/2010 | Yeh |
| 2010/0010429 A1 | 1/2010 | Childers |
| 2010/0078381 A1 | 4/2010 | Merchant |
| 2010/0078387 A1 | 4/2010 | Wong |
| 2010/0084330 A1 | 4/2010 | Wong |
| 2010/0094158 A1 | 4/2010 | Solem |
| 2010/0114012 A1 | 5/2010 | Sandford |
| 2010/0137693 A1 | 6/2010 | Porras |
| 2010/0168546 A1 | 7/2010 | Kamath |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2011/0017665 A1 | 1/2011 | Updyke |
| 2011/0066043 A1 | 3/2011 | Banet |
| 2011/0077574 A1 | 3/2011 | Sigg et al. |
| 2011/0079558 A1 | 4/2011 | Raimann |
| 2011/0087187 A1 | 4/2011 | Beck |
| 2011/0130666 A1 | 6/2011 | Dong et al. |
| 2011/0184340 A1 | 7/2011 | Tan |
| 2011/0272337 A1 | 11/2011 | Palmer |
| 2012/0016228 A1 | 1/2012 | Kroh |
| 2012/0083729 A1 | 4/2012 | Childers |
| 2012/0085707 A1 | 4/2012 | Beiriger |
| 2012/0115248 A1 | 5/2012 | Ansyln |
| 2012/0220528 A1 | 8/2012 | VanAntwerp |
| 2012/0258546 A1 | 10/2012 | Marran |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2013/0037465 A1 | 2/2013 | Heyes |
| 2013/0199998 A1 | 8/2013 | Kelly |
| 2013/0213890 A1 | 8/2013 | Kelly |
| 2013/0274642 A1 | 10/2013 | Soykan |
| 2013/0324915 A1 | 12/2013 | (Krensky) Britton |
| 2013/0330208 A1 | 12/2013 | Ly |
| 2013/0331774 A1 | 12/2013 | Farrell |
| 2014/0018728 A1 | 1/2014 | Plahey |
| 2014/0042092 A1 | 2/2014 | Akonur |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0220699 A1 | 8/2014 | Pudil |

FOREIGN PATENT DOCUMENTS

| | | |
|---|---|---|
| EP | 0906768 | 2/2004 |
| EP | 1450879 | 10/2008 |
| EP | 1592494 B1 | 6/2009 |
| EP | 2100553 A1 | 9/2009 |
| EP | 2575827 A2 | 12/2010 |
| EP | 2576453 A2 | 12/2011 |
| EP | 2701580 | 11/2012 |
| EP | 2701595 | 11/2012 |
| EP | 1345856 B1 | 3/2013 |
| EP | 2344220 B1 | 4/2013 |
| EP | 2701596 | 3/2014 |
| JP | 5099464 | 10/2012 |
| WO | 9937342 | 7/1999 |
| WO | 0057935 | 10/2000 |
| WO | 0185295 A2 | 9/2001 |
| WO | 0066197 A1 | 11/2001 |
| WO | 03043677 A2 | 5/2003 |
| WO | 03043680 | 5/2003 |
| WO | 03051422 A2 | 6/2003 |
| WO | 2004008826 | 1/2004 |
| WO | 2004009156 | 1/2004 |
| WO | 0170307 A1 | 4/2004 |
| WO | 2004030716 A2 | 4/2004 |
| WO | 2004030717 A2 | 4/2004 |
| WO | 2004064616 A2 | 8/2004 |
| WO | 2005123230 A2 | 12/2005 |
| WO | 2007089855 A2 | 8/2007 |
| WO | 2009026603 | 3/2009 |
| WO | 2009026603 A1 | 3/2009 |
| WO | 2009157877 | 12/2009 |
| WO | 2009157878 | 12/2009 |
| WO | 2010028860 A1 | 3/2010 |
| WO | 2011025705 A1 | 3/2011 |
| WO | 2012148781 | 11/2012 |
| WO | 2012148786 | 11/2012 |
| WO | 2012148789 | 11/2012 |
| WO | 2012162515 A2 | 11/2012 |
| WO | 2012172398 | 12/2012 |
| WO | 2013019179 A1 | 2/2013 |
| WO | 2013019994 | 2/2013 |
| WO | 2013025844 | 2/2013 |
| WO | 2013028809 A3 | 2/2013 |
| WO | 2013103607 A1 | 7/2013 |
| WO | 2013103906 | 7/2013 |
| WO | 2013114063 A | 8/2013 |
| WO | 2013121162 A1 | 8/2013 |
| WO | 2014066254 | 5/2014 |
| WO | 2014066255 | 5/2014 |
| WO | 2014077082 | 5/2014 |
| WO | 2014121162 | 8/2014 |
| WO | 2014121163 | 8/2014 |
| WO | 2014121167 | 8/2014 |
| WO | 2014121169 | 8/2014 |

OTHER PUBLICATIONS

Lakerveld et al, Primary prevention of diabetes mellitus type 2 and cardiovascular diseases using a cognitive behavior program aimed at lifestyle changes in people at risk: Design of a randomized controlled trial, 2008, BMC Endocrine Disorders, 8(6): 1-19.*
U.S. Appl. No. 60/650,497.
Roberts, The regenerative dialysis (REDY) sorbent system Nephrology, 1998, 275-278 : 4.
Bleyer, et al., Sudden and cardiac death rates in hemodialysis patients, Kidney International, 1999, 1553-1559 : 55.
U.S. Appl. No. 61/480,539.
Weiner, et. al., Article: Cardiac Function and Cardiovascular Disease in Chronic Kidney Disease, Book: Primer on Kidney Diseases (Author Greenberg, et al), 2009, 499-505, 5th Ed., Saunders Elsevier, Philadelphia, PA.
Ronco, et. al., Cardiorenal Syndrome, J. Am. Coll. Cardiol., 2008, 1527-1539 : 52.
Wang, Fundamentals of intrathoracic impedance monitoring in heart failure, Am. J. Cardiology, 2007, 3G-10G : Suppl.
Siegenthalar, et. al., Pulmonary fluid status monitoring with intrathoracic impedance, Journal of Clinical Monitoring and Computing, 2010, 449-451 : 24.
U.S. Appl. No. 61/480,532.
U.S. Appl. No. 13/424,479.
U.S. Appl. No. 13/424,429.
U.S. Appl. No. 13/424,525.
U.S. Appl. No. 61/480,544.

(56) References Cited

OTHER PUBLICATIONS

Maclean, et. al., Effects of hindlimb contraction on pressor and muscle interstitial metabolite responses in the cat, J. App. Physiol., 1998, 1583-1592, 85(4).
Overgaard, et. al., Activity-induced recovery of excitability in K+-depressed rat soleus muscle, Am. J. Physiol, Regulatory Integrative Comp. Physiol., 2001, R48-R55, vol. 280.
Overgaard, et. al., Relations between excitability and contractility in rate soleus muscle: role of the NA+-K+ pump and NA+-K+ gradients, Journal of Physiology, 1999, 215-225, 518(1).
U.S. Appl. No. 61/480,541.
U.S. Appl. No. 61/480,535.
U.S. Appl. No. 61/480,530.
U.S. Appl. No. 61/480,528.
ISA Invitation to Pay Additional Fees , PCT/US2012/034323 mailed Aug. 2, 2012.
International Search Report, PCT/US2012/034330 mailed Aug. 28, 2012.
International Search Report, PCT/US2012/034333 mailed Aug. 29, 2012.
U.S. Appl. No. 13/757,794, filed Feb. 2, 2013.
U.S. Appl. No. 13/757,722, filed Feb. 1, 2013.
U.S. Appl. No. 13/757,792, filed Feb. 2, 2013.
U.S. Appl. No. 13/791,755, filed Mar. 8, 2013.
PCT/US2014/014357 International Search Report and Written Opinion.
Leifer, I., et al., A Study on the Temperature Variation of Rise Velocity for Large Clean Bubbles, J. Atmospheric & Oceanic Tech., vol. 17, pp. 1392-1402.
Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
Talaia, MAR, Terminal Velocity of a Bubble Rise in a Liquid Column, Talaia, World Acad. of Sci., Engineering & Tech., vol. 28, pp. 264-268.
The FHN Trial Group. In-Center. Hemodialysis Six Times per Week versus Three Times per Week, New England Journal of Medicine, 2010.
U.S. Appl. No. 13/757,693, filed Feb. 1, 2013.
Coast, et al. 1990, An approach to Cardiac Arrhythmia analysis Using Hidden Markov Models, IEEE Transactions on Biomedical Engineering. 1990, 37 (9):826-835.
PCT/US2012/034330, International Preliminary Report on Patentability, Oct. 29, 2013.
U.S. Appl. No. 13/837,287, filed Mar. 15, 2013.
PCT Application, PCT/US20013/020404, filed Jan. 4, 2013.
U.S. Appl. No. 14/261,651, filed Apr. 25, 2014.
U.S. Appl. No. 13/836,973, filed Mar. 15, 2013.
U.S. Appl. No. 14/259,655, filed Apr. 23, 2014.
U.S. Appl. No. 14/259,589, filed Apr. 23, 2014.
PCT/US2012/034333, International Preliminary Report on Patentability, Oct. 29, 2013.
PCT/US2012/034333, International Search Report, Aug. 29, 2013.
Ang, Fundamentals of intrathoracic impedance monitoring in heart failure, Am. J. Cardiology, 2007, 3G-310: Suppl.
Brynda, et. al., The detection of toman 2-microglcbuiin by grating coupler immunosensor with three dimensional antibody networks. Biosensors & Bioelectronics, 1999, 363-368, 14(4).
Hemametrics, Crit-Line Hematocrit Accuracy, 2003, 1-5, vol. 1, Tech Note No. 11 (Rev. D).
Lima, et. al., An electrochemical sensor based on nanostructure hollsndite-type manganese oxide for detection of potassium ion, Sensors, 2009, 6613-8625, 9.
Nedelkov, et. al., Design of buffer exchange surfaces and sensor chips for biosensor chip mass spectrometry, Proteomics, 2002, 441-446, 2(4).
PCT/US/2012/034327, International Search Report, Aug. 13, 2013.
PCT/US/2012/034329, International Search Report, Dec. 3, 2012.
PCT/US2012/034331, International Search Report, Jul. 9, 2012.
PCT/US2012/034332, International Search Report, Jul. 5, 2012.
PCT/US2012/034334, International Search Report, Jul. 6, 2012.
PCT/US2012/034335, International Search Report, Sep. 5, 2012.
Redfield, et. al, Restoration of renal response to atria! natriuretic factor in experimental low-output heat failure, Am. J. Physiol., 1989, R917-923 : 257.
Rogoza, et. al., Validation of A&D UA-767 device for the self-measurement of blood pressure, Blood Pressure Monitoring, 2000, 227-231, 5(4).
Secemsky, et. al, High prevalence of cardiac autonomic dysfunction and T-wave alternans in dialysis patients. Heart Rhythm, Apr. 2011, 592-598 : vol. 8, No. 4.
Wei, et. al., Fullerene-cryptand coated piezoelectric crystal urea sensor based on urease, Analytica Chimica Acta, 2001,77-85:437.
Zhong, et. al., Miniature urea sensor based on H(+)-ion sensitive field effect transistor and its application in clinical analysis, Chin. J. Biotechnol., 1992, 57-65. 8(1).
U.S. Appl. No. 13/757,794, filed Feb. 2, 2012.
U.S. Appl. No. 13,837,287, filed Mar. 15, 2013.

* cited by examiner

METHOD AND DEVICE TO MONITOR PATIENTS WITH KIDNEY DISEASE

FIELD OF THE INVENTION

The invention relates to an electronic medical device for monitoring a mammal with kidney disease and issuing alerts if a kidney disease condition of the subject worsens. The systems and methods of the invention include an electronic circuit, sensors, a computer processor, a computational procedure and telecommunication means. The invention further relates to methods for signal processing and parameter identification.

BACKGROUND

Dialysis simulates kidney function by periodically removing waste solutes and excess fluid such as urea and ions from a patient's blood. This is accomplished by allowing the body fluids, usually blood, to come into close proximity with a dialysate, which is a fluid that serves to cleanse the blood and that actively removes the waste products including salts and urea, and excess water. Each dialysis session lasts a few hours and may typically be repeated as often as three times a week or more, such as 7 days a week.

Although effective at removing wastes from blood, dialysis treatments performed at dialysis centers are administered intermittently and therefore fail to replicate the continuous waste removal aspect of a natural and functioning kidney. Once a dialysis session is completed, fluid and other substances such as the sodium and potassium salts immediately begin to accumulate again in the tissues of the patient. Notwithstanding the benefits of dialysis, statistics indicate that three out of five dialysis patients die within five years of commencing treatment. Studies have shown that increasing the frequency and duration of dialysis sessions can improve the survivability of dialysis patients. Increasing the frequency and duration of dialysis sessions more closely resembles continuous kidney function. However, the requirement for patients to travel to the dialysis centers and the costs associated with the hemodialysis procedure itself pose an upper limit on the frequency of dialysis procedures.

Another complication is that as blood potassium levels increase between dialysis sessions, patients become more susceptible to life threatening arrhythmias. Similarly, low concentration of potassium can be dangerous by causing muscle weakness. Significant deviations from a normal physiological range of potassium must be detected and prevented to avoid worsening of patient conditions. In particular, patients with kidney disease (KD) are not able to adequately regulate bodily fluid levels and common blood solutes such as potassium ion. As such, KD patients are at risk for developing hyperkalemia (high blood potassium concentration) or hypokalemia (low blood potassium concentration). Normal blood potassium level is from 3.5 to 5.0 mEq; however, KD patients may tend to fall outside this range between treatments. Hyperkalemia and hypokalemia can lead to heart palpitations and arrhythmias.

Since patients with kidney failure cannot effectively eliminate potassium from their bodies, potassium must be removed during hemodialysis sessions. Between dialysis sessions of hyperkalemic patients, serum potassium concentration increases gradually until the next dialysis session. This increase in the potassium concentrations is a major cause of the increased rate of cardiovascular complications that is observed in the patients with kidney disease. Approximately 30% of these patients have atrial fibrillation, and according to the 2003-2005 USRDS data, an additional 6.2% deaths/year are caused by cardiac arrests or arrhythmias ("Primer on Kidney Diseases", 5th Ed., A. Greenberg et al., pp 504-5). Hence, there is a clear unmet need for monitoring patients between dialysis sessions. There is also an unmet need for monitoring and managing hyperkalemia, hypokalemia or arrhythmias in patients with KD.

In addition to being in danger of exposure to the complications of abnormal potassium levels between dialysis sessions, many kidney patients also experience an extreme variation of potassium levels during their dialysis sessions that increases their health risk. During hemodialysis, there is a net addition of base in the form of bicarbonate, which increases the cellular uptake of potassium and attenuates the overall removal of potassium from the cells. Hence, patients may initially experience an increase in their intracellular potassium levels followed by a reduction in levels resulting in hypokalemia. This condition is of particular concern to patients with underlying cardiac conditions. As such, there is a clear unmet need to guard against risk to patients during the dialysis sessions and during the post-treatment period.

SUMMARY OF THE INVENTION

The invention is directed to a medical device for monitoring subjects with kidney disease (KD) receiving dialysis treatment. Related medical systems and methods for implantable devices as well as external monitoring and treatment devices are provided.

In certain embodiments, the medical monitor has a medical device for determining body potassium status by monitoring electrical signals of the body of a subject, a processor for applying a forward computational procedure to the electrical signals monitored from the body in communication with the implantable medical device, and a communication system indicating a condition of hyperkalemia, hypokalemia or arrhythmia of the subject wherein the implantable medical device associates a cardiac cycle of the subject with a time index and calculates at least one risk score associated with the time index. The monitoring means can be implanted or external to the body. The processor is configured to receive clinical information regarding the physiological state of the subject associated with the time index and make an adjustment to the forward computational procedure based upon an error between the at least one risk score and the clinical information.

In certain embodiments, the medical device associates a cardiac cycle of the subject with a time index and calculates at least one risk score associated with the time index, and the processor configured to receive clinical information regarding the physiological state of the subject associated with a time index and make an adjustment to the forward computational procedure based upon an error between the at least one risk score and the clinical information. The medical monitor identifies a plurality of features from electrical signals monitored from the body of a patient, wherein the plurality of features includes one or more selected from the group consisting of P-R interval, QRS width, Q-T interval, QT-dispersion, P-wave amplitude, P-wave peak, S-T segment depression, T-wave inversion, U-wave amplitude, T-wave peak amplitude, T-wave morphology (e.g., spiked, rounded, etc.) and heart rate variability.

In certain embodiments, a medical monitor calculates a disease risk score from a plurality of features.

In certain embodiments, a first risk score is calculated for a time index by applying a first forward computational procedure to one or more of the features of P-R interval, S-T segment depression, T-wave inversion and U-wave amplitude.

In certain embodiments, a second score is calculated for a time index by applying a second forward computational procedure to the features of QRS width, Q-T interval, P-wave amplitude, P-wave peak, T-wave amplitude, and heart rate variation.

In certain embodiments, a processor of the medical monitor increases an alert counter by an incremental amount for each time index where a risk score exceeds a predetermined threshold and an alert is issued when the alert counter exceeds the predetermined threshold.

In one embodiment, the medical device is implanted and records physiological signals and sends the traces to an external processing unit for interpretation. In another embodiment, the medical device records the physiological signals external to the body and sends these traces to an external processing unit for interpretation. Resulting interpretation is provided to a medical professional as an aid for additional decisions.

In another embodiment, the medical device records and processes the physiological signals and sends interpretations of the subject's condition to the external units. At the same time, the device also warns the subject or a care giver with audible warnings or by other means. Resulting interpretation is again provided to a medical professional as an aid for additional decisions.

In another embodiment, parameters of the computational procedure used by the medical device are determined and adjusted by the medical professional.

In another embodiment, parameters of the computational procedure used by the medical device are learned by the computational procedure itself based on the arrhythmic outcomes of the patient.

In another embodiment, parameters of the computational procedure used by the medical device are learned by the computational procedure itself based on the medical outcomes of the patient, such as hospitalizations.

In certain embodiments, a has the steps of: (i) initiating a blood fluid removal session with initial system parameters; (ii) acquiring a first set of data regarding one or more patient physiological parameters; (iii) storing the first data set in a "most effective to date" data set memory; (iv) associating the initial system parameters in an increased effectiveness lookup table with the first data set; (v) adjusting at least one parameter of the blood fluid removal session to arrive at adjusted system parameters; (vi) acquiring a second set of data regarding the one or more patient physiological parameters after the at least one parameter of the blood fluid removal session has been adjusted; and (vii) if at least one value of the second data set is closer to the target value than a corresponding at least one value of the first data set: replacing the first data set in the most effective to date data set memory with the second data set; storing in the increased effectiveness lookup table data regarding the second data set; and associating data regarding the adjusted system parameters with the second data set.

In another embodiment, a method has steps of: (i) storing the first data set in a least effective to date data set memory; (ii) associating the initial system parameters in a becoming less effective lookup table with the first data set prior to adjusting the at least one parameter of the blood fluid removal session; and (iii) if the at least one value of the second data set is not closer to the target value than the corresponding at least one value of the first data set: replacing the first data set in the least effective to date data set memory with the second data set; storing in the becoming less effective lookup table data regarding the second data set; and associating data regarding the adjusted system parameters with the second data set.

In one more embodiment, a method has steps of: (i) further adjusting at least one parameter of the blood fluid removal session to arrive at further adjusted system parameters; (ii) acquiring a third set of data regarding the one or more patient physiological parameters after the at least one parameter of the blood fluid removal session has been further adjusted; and (iii) if at least one value of the third data set is closer to the target value than a corresponding at least one value stored in the most effective to date data set memory: replacing the data set in the most effective to date data set memory with the third data set; and storing in the increased effectiveness lookup table data regarding the third data set and associating data regarding the further adjusted system parameters with the third data set.

In certain embodiments, a method has the steps of: (i) further adjusting at least one parameter of the blood fluid removal session to arrive at further adjusted system parameters; (ii) acquiring a fourth set of data regarding the one or more patient physiological parameters after the at least one parameter of the blood fluid removal session has been further adjusted; and (iii) if at least one value of the fourth data set is not closer to the target value than a corresponding at least one value stored in the least effective to date data set memory: replacing the data set in the least effective to date data set memory with the fourth data set; and storing in the becoming less effective lookup table data regarding the fourth data set and associating data regarding the further adjusted system parameters with the fourth data set.

In another embodiment, a method has the steps of: (i) acquiring a fifth set of data regarding one or more patient physiological parameters; (ii) comparing the fifth data set to the increased effectiveness lookup table; and (iii) adjusting the system parameters the system parameters associated with the data set stored in the increased effectiveness lookup table if at least one parameter of the data set stored in the improvement lookup table is within a predetermined range of at least one corresponding parameter of the fifth data set.

In one more embodiment, a method has the steps of: (i) stopping the blood fluid removal session; (ii) acquiring a sixth set of data regarding one or more patient physiological parameters; (iii) comparing the sixth data set to the increased effectiveness lookup table; and (iv) initiating a second blood fluid removal session with the system parameters associated with the data set stored in the increased effectiveness lookup table if at least one parameter of the data set stored in the increased effectiveness lookup table is within a predetermined range of at least one corresponding parameter of the sixth data set.

In certain embodiments, a method has at least one of the one or more patient parameters selected from the group consisting of blood pressure, heart rate, pH and concentration of an electrolyte.

In certain embodiments, the electrolyte is potassium.

In certain embodiments, the system parameters have one or more of fluid removal rate and concentration of one or more electrolyte.

In certain embodiments, a dialysis system has: (a) a blood fluid removal medium or membrane configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; and (d) control electronics comprising memory and a processor, wherein the control electronics are in operable communication with the one or more sensors and are operably coupled to the one or more control elements, wherein the control electronics are configured to carry out a method described herein.

In certain embodiments, the blood fluid removal medium or membrane and the control electronics are housed within a blood fluid removal device.

In certain embodiments, a blood fluid removal or dialysis system has a computer readable, wherein the computer readable medium comprises instructions that cause the control electronics to carry out the methods.

In certain embodiments, a blood fluid removal or dialysis system has: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; and (d) control electronics comprising memory and a processor, wherein the control electronics are in operable communication with the one or more sensors and are operably coupled to the one or more control elements, wherein the control electronics are configured to (i) initiate a blood fluid removal session with initial system parameters; (ii) acquire a first set of data regarding one or more patient physiological parameters; (iii) store the first data set in a most effective to date data set memory; (iv) associate the initial system parameters in an increased effectiveness lookup table with the first data set; (v) adjust at least one parameter of the blood fluid removal session to arrive at adjusted system parameters; (vi) acquire a second set of data regarding the one or more patient physiological parameters after the at least one parameter of the blood fluid removal session has been adjusted; and (vii) if at least one value of the second data set is closer to a target value than a corresponding at least one value of the first data set: replace the first data set in the most effective to date data set memory with the second data set; store in the increased effectiveness lookup table data regarding the second data set; and associate data regarding the adjusted system parameters with the second data set.

In certain embodiments, a computer-readable medium has instructions that, when executed by a blood fluid removal device, cause the device to (i) initiate a blood fluid removal session with initial system parameters; (ii) acquire a first set of data regarding one or more patient physiological parameters; store the first data set in a most effective to date data set memory; (iii) associate the initial system parameters in an increased effectiveness lookup table with the first data set; (iv) adjust at least one parameter of the blood fluid removal session to arrive at adjusted system parameters; (v) acquire a second set of data regarding the one or more patient physiological parameters after the at least one parameter of the blood fluid removal session has been adjusted; and (vi) if at least one value of the second data set is closer to a target value than a corresponding at least one value of the first data set: replace the first data set in the most effective to date data set memory with the second data set; store in the increased effectiveness lookup table data regarding the second data set; and associate data regarding the adjusted system parameters with the second data set.

In certain embodiments, a method has the steps of: (a) acquiring data regarding one or more of: (i) one or more patient physiological parameters; and (ii) time since last blood fluid removal session; (b) acquiring data regarding one or more target outcomes of a blood fluid removal session; (c) comparing the data regarding at least one of the one or more target outcomes of the blood fluid session to corresponding data regarding at least one prior patient outcome stored in a lookup table, wherein the lookup table comprises data regarding system parameters used in one or more prior blood fluid removal sessions of the patient and comprises patient data prior to the previous session regarding one or more of (i) one or more patient physiological parameters; and (ii) time since last blood fluid removal session; (d) comparing the data regarding the one or more of (i) one or more patient physiological parameters; and (ii) time since last blood fluid removal session to corresponding patient data prior to the previous session stored in the lookup table; and (e) initiating a blood fluid removal session employing the system parameters used the prior blood fluid removal session if the at least one of the one or more target outcomes is within a predetermined range of the corresponding data regarding the at least one prior patient outcome stored in the lookup table and the data regarding the one or more of (i) one or more patient physiological parameters; and (ii) time since last blood fluid removal session is within a predetermined range of the corresponding patient data prior to the previous session stored in the lookup table.

In certain embodiments, a method has at least one of the one or more patient parameters selected from the group consisting of blood pressure, heart rate, pH and concentration of an electrolyte.

In certain embodiments, the system parameters are one or more of fluid removal rate and concentration of one or more electrolyte.

In certain embodiments, a blood fluid removal system has: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; (d) an input configured to allow entry of data regarding patient or system parameters; and (e) control electronics comprising memory and a processor, wherein the control electronics are in operable communication with the one or more sensors and are operably coupled to the one or more control elements and the input, wherein the control electronics are configured to carry out a method described herein.

In certain embodiments, the blood fluid removal medium or membrane and the control electronics are housed within a blood fluid removal or dialysis device.

In certain embodiments, a blood fluid removal or dialysis system has a computer readable, wherein the computer readable medium has instructions that cause control electronics to carry out a method described herein.

In certain embodiments, a blood fluid removal or dialysis system has: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; (d) an input configured to allow entry of data regarding patient or system parameters; and (e) control electronics comprising memory and a processor, wherein the control electronics are in operable communication with the one or more sensors and are operably coupled to the one or more control elements and the input, wherein the control electronics are configured to: (i) acquire data regarding one or more of: one or more patient physiological parameters; and time since last blood fluid removal session; (ii) acquire data regarding one or more target outcomes of a blood fluid removal session; (iii) compare the data regarding at least one of the one or more target outcomes to corresponding data regarding at least one prior patient outcome stored in a lookup table, wherein the lookup table comprises data regarding system parameters used in one or more prior blood fluid removal sessions of the patient and comprises patient data prior to the previous session regarding one or more of (i) one or more patient physiological parameters; and (ii) time since last blood fluid removal session; (iv) compare the data regarding the one or more of (i) one or more patient physiological parameters; and (ii) time since last blood fluid removal session to corresponding patient data prior to the previous session stored in the lookup table; and (v) initiate a blood fluid removal session employing the system parameters used in the prior blood fluid removal session if the at least one of the one or more target outcomes is within a predetermined range of the corresponding data regarding the at least one prior patient outcome stored in the lookup table and the data regarding the one or more of (i) one or more patient physiological parameters; and (ii) time since last blood fluid removal session is within a predetermined range of the corresponding patient data prior to the previous session stored in the lookup table.

In certain embodiments, a computer-readable medium has instructions that, when executed by a blood fluid removal or dialysis device, cause the device to (i) acquire data regarding one or more of: one or more patient physiological parameters; and time since last blood fluid removal session; (ii) acquire data regarding one or more target outcomes of a blood fluid removal session; (iii) compare the data regarding the at least one of the one or more target outcomes to corresponding data regarding at least one prior patient outcome stored in a lookup table, wherein the lookup table comprises data regarding system parameters used in one or more prior blood fluid removal sessions of the patient and comprises patient data prior to the previous session regarding one or more of one or more patient physiological parameters and time since last blood fluid removal session; (iv) compare the data regarding the one or more of (i) one or more patient physiological parameters; and (ii) time since last blood fluid removal session to corresponding patient data prior to the previous session stored in the lookup table; and (v) initiate a blood fluid removal session employing the system parameters used in the prior blood fluid removal session if the at least one of the one or more target outcomes is within a predetermined range of the corresponding data regarding the at least one prior patient outcome stored in the lookup table and the data regarding the one or more of (i) one or more patient physiological parameters; and (ii) time since last blood fluid removal session is within a predetermined range of the corresponding patient data prior to the previous session stored in the lookup table.

In certain embodiments, a method has the steps of: (i) collecting first data regarding a patient, the data including one or more of a physiological parameter and time since last blood fluid removal session; (ii) collecting second data regarding system parameters employed in blood fluid removal sessions of the patient; (iii) determining, based on the first and second collected data, whether at least one physiological parameter of the patient became more effective as a result of the system parameters employed; (iv) determining whether a value of current patient data is within a predetermined range of a corresponding value of first collected data; and (v) employing the system parameters that resulted in increased effectiveness, if such parameters are determined to exist and if the current patient data is determined to be within the predetermined range.

In certain embodiments, a blood fluid removal or dialysis system has: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; (d) an input configured to allow entry of data regarding patient or system parameters; and (e) control electronics comprising memory and a processor, wherein the control electronics are in operable communication with the one or more sensors and are operably coupled to the one or more control elements and the input, wherein the control electronics are configured to carry out a method described herein.

In certain embodiments, a blood fluid removal system or dialysis system has a computer readable media, wherein the computer readable media comprises instructions that cause control electronics to carry out a method described herein.

In certain embodiments, a system has: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; (d) an input configured to allow entry of data regarding patient or system parameters; and (e) control electronics comprising memory and a processor, wherein the control electronics are in operable communication with the one or more sensors and are operably coupled to the one or more control elements and the input, wherein the control electronics are configured to: (i) collect first data regarding a patient, the data including one or more of a physiological parameter and time since last blood fluid removal session; (ii) collect second data regarding system parameters employed in blood fluid removal sessions of the patient; (iii) determine, based on the first and second collected data, whether at least one physiological parameter of the patient became more effective as a result of the system parameters employed; (iv) determine whether a value of current patient data is within a predetermined range of a corresponding value of first collected data; and (v) employ the system parameters that resulted in increased effectiveness, if such parameters are determined to exist and if the current patient data is determined to be within the predetermined range.

In certain embodiments, a computer-readable medium has instructions that, when executed by a blood fluid removal device, cause the device to (i) collect first data regarding a patient, the data including one or more of a physiological parameter and time since last blood fluid removal session; (ii) collect second data regarding system parameters employed in blood fluid removal sessions of the patient; (iii) determine, based on the first and second collected data, whether at least one physiological parameter of the patient became more effective as a result of the system parameters employed; (iv) determine whether a value of current patient data is within a predetermined range of a corresponding value of first collected data; and (v) employ the system parameters that resulted in increased effectiveness, if such parameters are determined to exist and if the current patient data is determined to be within the predetermined range.

In certain embodiments, a method has the steps of: (i) storing system parameters from a first blood fluid removal session in memory; (ii) acquiring a first set of data regarding one or more patient parameters following the first session but before a second session; (iii) storing the first data set in a most effective to date data set memory; (iv) associating the first system parameters in an increased effectiveness lookup table with the first data set; (v) storing system parameters from the second blood fluid removal session in memory; (vi) acquiring a second set of data regarding the one or more patient parameters following the second session; (vii) determining whether at least one value of the second data set is closer to a target value than at least one corresponding value of the first data set; and (viii) if the at least one value of the second data set is determined to be closer to the target value than the corresponding at least one value of the first data set: replacing the first data set in the most effective to date data set memory with the second data set; storing in the increased effectiveness lookup table data regarding the second data set; and associating data regarding the second system parameters with the second data set.

In certain embodiments, a method has the steps of: (i) storing the first data set in a least effective to date data set memory; (ii) associating the first system parameters in a decreased effectiveness lookup table with the first data set; and (iii) if the at least one value of the second data set is determined not to be closer to the target value than the corresponding at least one value of the first data set: replacing the first data set in the least effective to date data set memory with the second data set; storing in the decreased effectiveness lookup table data regarding the second data set; and associating data regarding the second system parameters with the second data set.

In certain embodiments, a method has the steps of: (i) storing system parameters for a third blood fluid removal session in memory; (ii) acquiring a third set of data regarding the one or more patient parameters following the third session; (iii) determining whether at least one value of the third data set is closer to a target value than at least one corresponding value stored in the most effective to date data set memory; and (iv) if the at least one value of the third data set is determined to be closer to the target value than the corresponding at least one value stored in the most effective to date data set memory: replacing the data set in the most effective to date data set memory with the third data set; and storing in the increased effectiveness lookup table data regarding the third data set and associating data regarding the third system parameters with the third data set.

In certain embodiments, a method has the steps of: (i) storing system parameters from a fourth blood fluid removal session in memory; (ii) acquiring a fourth set of data regarding the one or more patient parameters following the fourth session; (iii) determining whether at least one value of the fourth data set is further from a target value than at least one corresponding value stored in the least effective to date data set memory; and (iv) if the at least one value of the fourth data set is determined not to be closer to the target value than the corresponding at least one value stored in the least effective to date data set memory: replacing the data set in the least effective to date data set memory with the fourth data set; and storing in the decreased effectiveness lookup table data regarding the fourth data set and associating data regarding the fourth system parameters with the fourth data set.

In certain embodiments, a method has the steps of: (i) acquiring a fifth set of data regarding one or more patient parameters; (ii) consulting the increased effectiveness lookup table to determine whether at least one parameter of a data set stored in the increased effectiveness lookup table is within a predetermined range of the fifth data set; and (iii) setting system parameters for a next blood fluid removal session to the system parameters associated with the data set stored in the increased effectiveness lookup table.

In certain embodiments, at least one of the one or more patient parameters are selected from the group consisting of blood pressure, heart rate, pH and concentration of an electrolyte.

In certain embodiments, the system parameters have one or more of fluid removal rate and concentration of one or more electrolyte.

In certain embodiments, the method is carried out by a blood fluid removal system.

In certain embodiments, a blood fluid removal system has the steps of: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; and (d) control electronics comprising memory and a processor, wherein the control electronics are in operable communication with the one or more sensors and are operably coupled to the one or more control elements.

In certain embodiments, the blood fluid removal medium and the control electronics are housed within a blood fluid removal device.

In certain embodiments, a blood fluid removal system has a computer readable media, wherein the computer readable media has instructions that cause control electronics to carry out a method described herein.

In certain embodiments, a system has: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; and (d) control electronics comprising memory and a processor, wherein the control electronics are in operable communication with the one or more sensors and are operably coupled to the one or more control elements, wherein the control electronics are configured to (i) store system parameters from a first blood fluid removal session in memory; (ii) acquire a first set of data regarding one or more patient parameters following the first session but before a second session; (iii) store the first data set in a most effective to date data set memory; (iv) associate the first system parameters in an increased effectiveness lookup table with the first data set; (v) store system parameters from the second blood fluid removal session in memory; (vi) acquire a second set of data regarding the one or more patient parameters following the second session; (vii) determine whether at least one value of the second data set is closer to a target value than at least one corresponding value of the first data set; and (viii) if the at least one value of the second data set is determined to be closer to the target value than the corresponding at least one value of the first data set: replace the first data set in the most effective to date data set memory with the second data set; store in the increased effectiveness lookup table data regarding the second data set; and associate data regarding the second system parameters with the second data set.

In certain embodiments, a computer-readable medium has instructions that, when executed by a blood fluid removal device, cause the device to (i) store system parameters from a first blood fluid removal session in memory; (ii) acquire a first set of data regarding one or more patient parameters following the first session but before a second session; (iii) store the first data set in a most effective to date data set memory; (iv) associate the first system parameters in an increased effectiveness lookup table with the first data set; (v) store system parameters from the second blood fluid removal session in memory; (vi) acquire a second set of data regarding the one or more patient parameters following the second session; (vii) determine whether at least one value of the second data set is closer to a target value than at least one corresponding value of the first data set; and (viii) if the at least one value of the second data set is determined to be closer to the target value than the corresponding at least one value of the first data set: replace the first data set in the most effective to date data set memory with the second data set; store in the increased effectiveness lookup table data regarding the second data set; and associate data regarding the second system parameters with the second data set.

In certain embodiments, a method has the steps of (i) identifying a patient for which a blood fluid removal session is indicated; and (ii) chronically monitoring an indicator of blood electrolyte concentration or blood pH of the patient via an implantable sensor device.

In certain embodiments, a method has the steps of: (i) determining whether the monitored indicator crosses a predetermined threshold; and (ii) alerting the patient if the indicator is determined to cross the threshold.

In certain embodiments, a method has the step of alerting a healthcare provider if the indicator is determined to cross the threshold.

In certain embodiments, a method has the step of determining an appropriate electrolyte concentration or buffer concentration for a fluid to be used in a blood fluid removal session based on the monitored indicator.

In certain embodiments, a fluid to be used in a blood fluid removal or dialysis session comprises dialysate fluid.

In certain embodiments, a fluid to be used in a blood fluid removal session or dialysis session comprises replacement fluid.

In certain embodiments, a method has the step of transmitting data regarding a monitored indictor to a blood fluid removal device, or control electronics configured to control a blood fluid removal device, wherein the blood fluid removal or dialysis device, monitoring device or control electronics determines the appropriate electrolyte concentration or buffer concentration.

In certain embodiments, monitoring includes monitoring the indicator via an implantable sensor.

In certain embodiments, a method has the step of: monitoring an indicator via an external sensor, and calibrating an implantable sensor based on data acquired from the external sensor.

In certain embodiments, monitoring via an external sensor occurs during a blood fluid removal or dialysis session, and wherein the calibrating occurs during a blood fluid removal or dialysis session.

In certain embodiments, a method has the steps of: (i) chronically monitoring, via an implantable sensor, an indicator of blood electrolyte concentration or blood pH of the patient during the blood fluid removal session; and (ii) initiating blood fluid removal procedure for a patient in need thereof, wherein the procedure comprises use of a dialysate fluid and a dialysate membrane, as at least a part of a blood fluid removal medium or membrane, across which electrolytes may be exchanged between blood and dialysate fluid, wherein the concentration of electrolyte in the dialysate fluid is based on a value of the monitored indicator.

In certain embodiments, a method has the steps of: (i) chronically monitoring, via an implantable sensor, an indicator of blood electrolyte concentration or blood pH of the patient during the blood fluid removal session; and (ii) initiating blood fluid removal procedure for a patient in need thereof, wherein the procedure comprises use of a dialysate fluid and a dialysate membrane, as at least a part of a blood fluid removal medium or membrane, across which electrolytes may be exchanged between blood and dialysate fluid, wherein the rate of flow of the dialysate fluid or the blood is based on a value of the monitored indicator.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

DETAILED DESCRIPTION OF THE INVENTION

Figure 1:
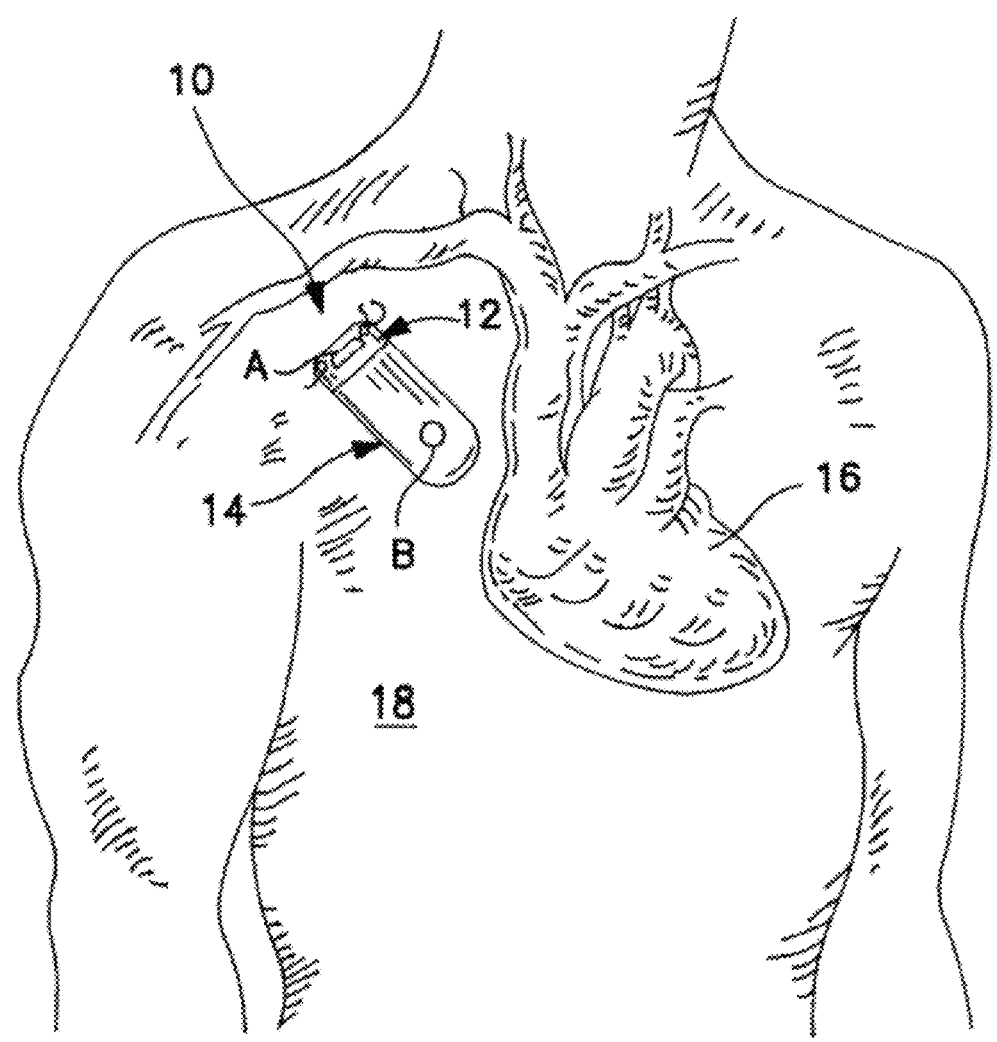
FIG. 1 is an exemplary embodiment of an EKG monitor.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

"Chronic kidney disease" (CKD) is a condition characterized by the slow loss of kidney function over time. The most common causes of CKD are high blood pressure, diabetes, heart disease, and diseases that cause inflammation in the kidneys. Chronic kidney disease can also be caused by infections or urinary blockages. If CKD progresses, it can lead to end-stage renal disease (ESRD), where the kidneys function is inadequate to sustain life without supplemental treatment.

The terms "communicate" and "communication" include but are not limited to, the connection of system electrical elements, either directly or wirelessly, using optical, electromagnetic, electrical or mechanical connections, for data transmission among and between said elements.

The term "comprising" includes, but is not limited to, whatever follows the word "comprising." Thus, use of the term indicates that the listed elements are required or mandatory but that other elements are optional and may or may not be present.

The term "consisting of" includes and is limited to whatever follows the phrase the phrase "consisting of." Thus, the phrase indicates that the limited elements are required or mandatory and that no other elements may be present.

A "control system" consists of combinations of components that act together to maintain a system to a desired set of performance specifications. The performance specifications can include sensors and monitoring components, processors, memory and computer components configured to interoperate.

A "controller" or "control unit" is a device which monitors and affects the operational conditions of a given system. The operational conditions are typically referred to as output variables of the system, which can be affected by adjusting certain input variables.

A "patient" is a member of any animal species, preferably a mammalian species, optionally a human. The subject can be an apparently healthy individual, an individual suffering from a disease, or an individual being treated for an acute condition or a chronic disease.

The term "programmable" as used herein refers to a device using computer hardware architecture and being capable of carrying out a set of commands, automatically.

The term "sensory unit" refers to an electronic component capable of measuring a property of interest.

The terms "treating" and "treatment" refer to the management and care of a patient having a pathology or condition. Treating includes administering one or more embodiments of the present invention to prevent or alleviate the symptoms or complications or to eliminate the disease, condition, or disorder.

As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a patient.

Electrocardiogram or ECG is a time varying waveform, produced by the electrical activity of the cardiac muscle and the associated electrical network within the myocardium. Term is used interchangeably for the tracing that is available from the surface of the subject, or from an implantable or external device.

The term "P-R interval" refers to the length of time from the beginning of the P wave to the beginning of the QRS complex.

The term "QRS width" refers to the length of time of the QRS complex.

The term "Q-T interval" refers to the length of time from the beginning of the QRS complex to the end of the T-wave.

The term "Q-T dispersion" refers to the difference between the maximum and minimum QT intervals measured in a time period.

The term "P-wave amplitude" refers to the maximum potential reached by the P-wave.

The term "P-wave peak" refers to the rate of change in the P wave in units of potential change per unit time.

The term "S-T segment" refers to the interval between the QRS complex and the beginning of the T wave. S-T segment is depressed if it has a downward concavity.

The term "T wave" refers to the wave after the QRS complex and the S-T segment. An inverted T wave has a negative amplitude.

The term "U wave amplitude" refers to the maximum potential of a wave that follows the T wave. The U wave is not always observed in a cardiac cycle.

The term "heart rate variability" refers to the time difference between the peaks of R-waves over time in cardiac cycles.

The term "scalar quantity" or "scalar value" refers to a property, value or quantity that is completely expressed in terms of magnitude.

The term "feature," "cardiac feature," "ECG feature" or "feature of a cardiac cycle" refers to a property of the a cardiac cycle, as observed by ECG or other means, that is reducible to numerical form. Features include, but are not limited to, P-R interval, QRS width, Q-T interval, P-wave amplitude, S-T segment depression, T wave inversion, U wave amplitude and T wave amplitude.

The term "feature value" refers to a feature of a cardiac cycle expressed as a scalar quantity or qualitative property such as depressed or inverted.

The term "feature score" refers to a feature value that has been converted to a common scale.

The term "common scale" refers to a unitless scale for expressing feature values where the common scale has a minimum possible value and a maximum possible value and the feature values differ in units or lack a common range of magnitude. In some embodiments, the common scale has a minimum value of 0 and a maximum value of 1.

The term "determinant" or "determinate value" refers to a quantity or criterion that a feature value or feature score is compared to for the purposes of calculating a risk score.

The term "risk score" or "disease risk score" refers to value calculated with one or more feature values or scores that indicates an undesirable physiological state of the patient.

The term "exponential factor," "value k," or "variable k" refers to a modifiable variable present in an exponent (e.g. $e^k$) in a computational procedures used to convert a feature value to a feature score.

The term "weighting factor" or "weighting coefficient" refers to an adjustable coefficient to terms for addition to calculate a disease risk score.

The term "hypokalemia" refers to a physiological state wherein the concentration of potassium ions in the blood serum or interstitial fluid is less than the normal physiological range of 3.5 to 5 mEq/L.

The term "hyperkalemia" refers to a physiological state wherein the concentration of potassium ions in the blood serum or interstitial fluid is more than the normal physiological range of 3.5 to 5 mEq/L.

"Kidney disease" (KD) is a condition characterized by the slow loss of kidney function over time. The most common causes of KD are high blood pressure, diabetes, heart disease, and diseases that cause inflammation in the kidneys. Kidney disease can also be caused by infections or urinary blockages. If KD progresses, it can lead to end-stage renal disease (ESRD), where kidney function is inadequate to sustain life without supplemental treatment. KD can be referred to by different stages indicated by Stages 1 to 5. Stage of KD can be evaluated by glomerular filtration rate of the renal system. Stage 1 KD can be indicated by a GFR greater than 90 mL/min/1.73 m² with the presence of pathological abnormalities or markers of kidney damage. Stage 2 KD can be indicated by a GFR from 60-89 mL/min/1.73 m², Stage 3 KD can be indicated by a GFR from 30-59 mL/min/1.73 m² and Stage 4 KD can be indicated by a GFR from 15-29 mL/min/1.73 m². A GFR less than 15 mL/min/1.73 m² indicates Stage 5 KD or ESRD. It is understood that KD, as defined in the present invention, contemplates KD regardless of the direction of the pathophysiological mechanisms causing KD and includes CRS Type II and Type IV and Stage 1 through Stage 5 KD among others. Kidney disease can further include acute renal failure, acute kidney injury, and worsening of renal function. In the Cardiorenal Syndrome (CRS) classification system, CRS Type I (Acute Cardiorenal Syndrome) is defined as an abrupt worsening of cardiac function leading to acute kidney injury; CRS Type II (Chronic Cardiorenal syndrome) is defined as chronic abnormalities in cardiac function (e.g., chronic congestive heart failure) causing progressive and permanent kidney disease; CRS Type III (Acute Renocardiac Syndrome) is defined as an abrupt worsening of renal function (e.g., acute kidney ischaemia or glomerulonephritis) causing acute cardiac disorders (e.g., heart failure, arrhythmia, ischemia); CRS Type IV (Chronic Renocardiac syndrome) is defined as kidney disease (e.g., chronic glomerular disease) contributing to decreased cardiac function, cardiac hypertrophy and/or increased risk of adverse cardiovascular events; and CRS Type V (Secondary Cardiorenal Syndrome) is defined as a systemic condition (e.g., diabetes mellitus, sepsis) causing both cardiac and renal dysfunction (Ronco et al., Cardiorenal syndrome, J. Am. Coll. Cardiol. 2008; 52:1527-39).

Monitoring of Dialysis Treatment

As discussed above, a patient's serum potassium level can be unstable and/or drift after dialysis treatment. Due to the requirement for proper polarization for cardiac function, changes in potassium serum levels after treatment are a contributor to arrhythmias and other cardiac complications in patients undergoing kidney dialysis therapy. During dialysis treatment, small solutes in the blood or other body fluids, such as potassium ions, freely interchange with a dialysate fluid. However, due to the action of the sodium-potassium pump, the vast majority of potassium in the body is present intracellularly and not directly accessible during dialysis. Due to the sequestering of potassium within cells, potassium serum levels can change significantly following dialysis treatment sessions. Specifically, dialysis treatment can enhance the movement of potassium ions into the cells, which can efflux out of the cells following treatment leading to significant changes in potassium ion concentration over time.

Normal serum potassium level ranges from 3.5 to 5 mEq/L, wherein a dialysate solution is at a lower concentration to drive the movement of potassium ions from the serum to the dialysate. As dialysis functions to remove potassium ions from the blood serum as a result of a concentration gradient between the patient's blood serum and the dialysate, additional potassium ions are drawn out from cells into the intracellular fluids to provide for further removal of potassium ions. However, the movement of potassium ions from inside cells to the extracellular fluids is not consistent in all patients. In particular, acid-base balance can affect the influx and efflux of potassium ions from cells. Tonicity, glucose and insulin concentrations and catecholamine activity also affect the balance of potassium between cells and the extracellular fluid. Patients can experience slight alkalosis during at the beginning of dialysis treatment, which can persist during a multi-hour dialysis treatment. Alkalosis is caused by the bicarbonate present in the dialysate, which acts as a pH buffer. During alkalosis, it is possible for intracellular potassium ion concentrations to increase even while the serum potassium ion concentration is simultaneously being reduced by dialysis. As such, the rate of potassium removal is not uniform during dialysis.

At the end of dialysis treatment, an efflux of intracellular potassium back into the blood serum can result in hyperkalemia. Hyperkalemia can also occur through the accumulation of potassium in the patient's diet. Conversely, potassium in the blood serum can remain low following dialysis resulting in hypokalemia. The innovations disclosed herein enable the monitoring of a patient's serum potassium level during dialysis, after dialysis or both during and after dialysis. In certain embodiments, ECG signals from the patient can be evaluated to determine potassium status. For example, hyperkalemia can cause a reduction in P wave amplitude, peaked or inverted T waves as well as changes in the time width of the QRS complex.

Using the innovations described herein, a patient can be monitored for potentially life-threatening hyperkalemia or hypokalemia after a dialysis session possibly before the patient becomes aware of symptoms. In certain embodiments, the information gained regarding the patient's blood serum potassium levels following dialysis can be used to adjust dialysis treatments provided to that patient. For example, a patient that shows a pattern of a high serum potassium levels after dialysis treatment be administered treatment where the amount of potassium salt in the dialysate fluid is adjusted, for example by a gradient, from a high concentration at the beginning of dialysis to a lower concentration at the end of dialysis to reduce the large changes in potassium plasma levels during treatment that can result in hyperkalemia. Alternatively, a patient showing a tendency toward hyperkalemia can receive more frequent treatments and/or more frequent treatments of shorter duration to affect a greater degree of potassium removal. A patient can even be advised to modify their diet passed upon blood serum potassium levels following dialysis. Similarly, a patient showing a tendency toward hypokalemia following dialysis can receive less frequent treatment or treated with a dialysate fluid having a higher concentration of potassium salt.

In some embodiments, serum potassium concentration, electrolyte levels and or pH can be monitored before and/or during a dialysis treatment for better management of electrolytes, including potassium, in the patient. Any suitable transducer or sensor can be employed to detect pH or various electrolytes in the blood prior to initiation of a dialysis treatment. In embodiments, the transducer or sensor is an ion-selective electrode configured to detect $H^+$ ions (pH), $K^+$ ions, $Na^+$ ions, $Ca^{2+}$ ions, $Cl^-$ ions, phosphate ions, magnesium ions, acetate ions, amino acids ions, or the like. Data from the pH and/or ion sensors/electrodes can be employed to appropriately select an initial dialysate composition prior to the beginning of a dialysis treatment. Data acquired from the sensors can be transmitted to a processor or other device or devices in communication with a dialysis treatment system, wherein the initial pH and electrolyte composition of a dialysate or a replacement fluid can be adjusted. The pH and electrolyte concentration of the fluid (dialysate or replacement fluid) can be adjusted in any suitable manner.

In particular, data from pH and/or ion sensors/electrodes can be transmitted to be available to a healthcare provider through the processor or other device and used to adjust the concentration of electrolytes or pH in a dialysate or replacement fluid. In some embodiments, the dialysate is generated from water or a low-concentration solution present in a dialysate circuit in fluid communication with the patient, wherein one or more pumps controls the addition of one or more infusate solutions to the dialysate circuit to constitute a desired dialysate immediately prior to contact with the patient or a hemodialyzer. The dialysate can be constitute to affect a specific mass transfer of electrolytes from the blood of a patient to the dialysate or from the dialysate to the blood of a patient in a manner to correct any determined electrolyte imbalances or non-ideal electrolyte ranges. Similarly, the amount of a buffer, such as bicarbonate, in the dialysate can be adjusted to vary the amount of bicarbonate uptake by the patient during treatment.

Medical Device

The systems and medical devices of the present invention monitor physiological signals from patients. The medical devices provide many advantages including full patient compliance, complete patient mobility, lower maintenance requirements and lower chances for device related infections. The medical devices can be powered with internal batteries and can be implanted or external to the body. Data transmission to and from the devices is accomplished by electromagnetic or electroconductive telemetry means. In embodiments of the invention, the medical devices contain one or multiple sets of sensors. For example, the devices can sense the ECG of a patient and change in activity or posture of the patient. The sensed signals can be stored in memory and transmitted via radio telemetry. Furthermore, the processor units within the medical devices can be used to process the detected or recorded signals.

The ECG signals can be processed to extract features from the ECG signal. These features include but are not limited to P-R interval, QRS width, Q-T interval, QT-dispersion, P-wave amplitude, P-wave peak, S-T segment depression, Inverted T-waves, U-wave observation, T-wave peak amplitude, Heart Rate Variability. While some features are measured for each cardiac cycle such as the P-R interval, others are calculated as a time average such as heart rate variability.

Many factors affect the features of the ECG. For example, heart rate varies as a result of changes in metabolic demand. During exercise, an increased demand for oxygen causes the heart rate to increase. Correspondingly, the P-R interval decreases during exercise. Another factor that modulates the features of the ECG is changes in the concentrations of the ions in the body. An ion that modulates the ECG and is important for the management of KD patients is potassium ion. In general, changes in potassium concentrations manifest as alterations of some of the features of the ECG. However, these alterations vary from one patient to another patient and can necessitate the individualization of the detection computational procedure as described herein.

In particular, the medical device of the present invention monitors a patient electrocardiogram (ECG) wherein an internal or external processing unit extracts features from the ECG and processes the resulting data. An optional telemetry system or any other alert system, such as an audio feedback device, can communicate the results to the patient and medical care personnel as needed. In certain embodiments, the device has an electrical pulse generator configured to contact the tissue of a patient such as muscle tissue or cardiac tissue, and a sensor to detect a response of the tissue where the response provides an indication of the potassium ion concentration in the extracellular fluid. In another embodiment, the device comprises a pulse generator configured to generate electrical stimulation wherein an electrode delivers electrical stimulation to a tissue such as a skeletal muscle in a patient. The device can include a sensor configured to detect at least one response of the tissue to electrical stimulation, and a processor configured to determine a concentration of potassium ions in the extracellular fluid of the patient as a function of the response. In particular, the processor can be configured to determine a concentration of potassium ions as a function of a sustained contraction of the tissue, for example, or a rippled contraction of the tissue, a rate of relaxation of the tissue, a pulse width of the response, the occurrence of summation in the response or the amplitude of the response. The system can be external, partially implantable or fully implantable. Notably, a healthy level of potassium in the human blood is about 3.5-5 mEq/L, but in patients with KD, the concentration could rise to 6-8 mM. Most patients are dialyzed with hypo-osmotic dialysate solutions where the potassium concentration is fixed at a hypo-osmotic level, such as 2 mM, to assure the transfer of potassium ions from the patient's blood into the dialysate solution.

The medical device can be a unit with no leads or may contain leads and external sensors. Units with no leads such as the Medtronic Reveal® device, or other known devices familiar to those of ordinary skill, may have electrodes for sensing electrocardiograms or for delivering electrical stimulation. Units with leads, such as pacemakers, cardiac resynchronization devices and defibrillators, utilize their leads for sensing electrocardiograms. The medical device may also have other sensors, such as an internal accelerometer and an external pressure sensor, which is external to the device yet still reside inside the patient. The device can contain a power source such as a battery, a computing hardware, a data storage unit such as electronic memory and communication hardware or related systems.

FIG. 1 presents an embodiment of an implantable medical device that may be used to obtain ECG data without the use of leads. However, external embodiments are contemplated by the invention. A monitor 10 is implanted subcutaneously in the upper thoracic region of the patient's body 18 near the patient's heart 16. The monitor 10 comprises a nonconductive header module 12 attached to a hermetically sealed enclosure 14. The enclosure 14 contains the operating system of the monitor 10 and is preferably conductive but can be covered in part by an electrically insulating coating. A first, subcutaneous, sensing electrode A is formed on the surface of the header module 12 and a second, subcutaneous, sensing electrode B is formed by an exposed portion of the enclosure 14. A feed-through extends through the mating surfaces of the header module 12 and the enclosure 14 to electrically connect the first sensing electrode A with the sensing circuitry (not shown) within the enclosure 14, and the conductive sensing electrode B directly to the sensing circuitry.

The electrical signals attendant to the depolarization and re-polarization of the heart 16 referred to as the ECG are sensed across the sensing electrodes A and B. The monitor 10 is sutured to subcutaneous tissue at a desired orientation for electrodes A and B relative to the axis of the heart 16 to detect and record the ECG in a sensing vector A-B for subsequent uplink telemetry transmission to an external programmer (not shown). FIG. 1 shows only one possible orientation of the sensing electrodes A and B and sensing vector A-B. It will be understood by those of ordinary skill in the art that additional orientations are possible. The hermetically sealed enclosure 14 includes a battery, circuitry that controls device operations and records ECG data in memory registers, and a telemetry transceiver antenna or transceiver electrodes and circuit that receives downlink telemetry commands from and transmits stored data in a telemetry uplink to the external programmer. The circuitry and memory can be implemented in discrete logic or a micro-computer based system with Analog/Digital conversion of sampled ECG amplitude values.

Figure 2:
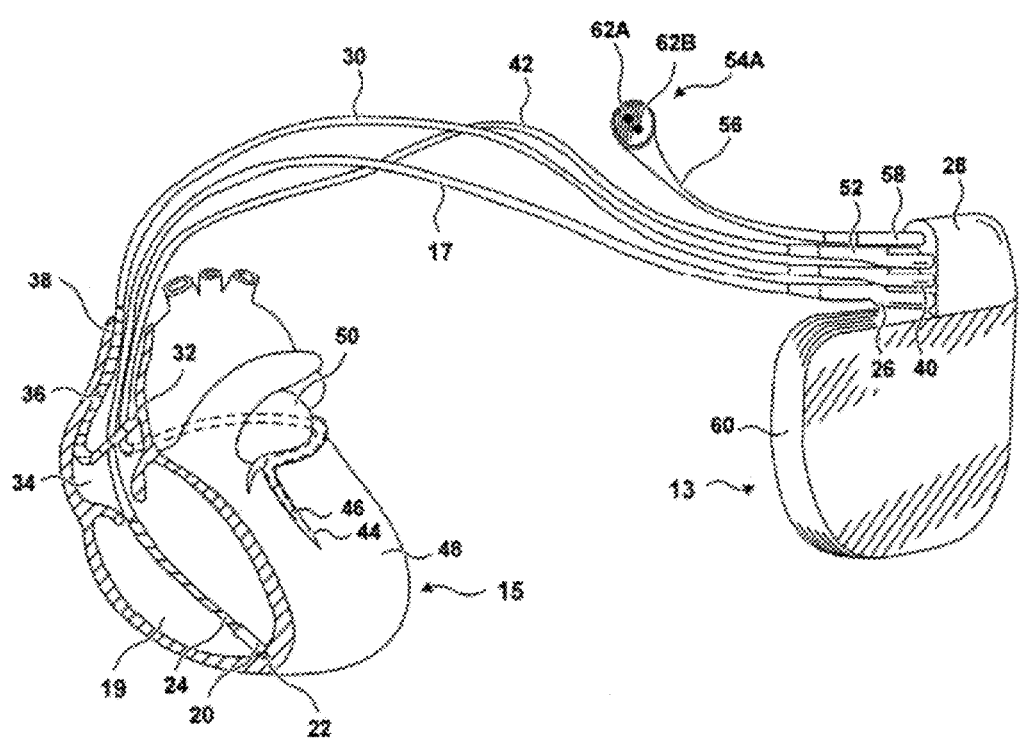
FIG. 2 is an exemplary embodiment of an EKG monitor having additional functionality to supply an electrical stimulation to muscle tissue and a sensor to observe a mechanical response.

As depicted in FIG. 2, an implantable medical device (IMD) 13 is a multichamber pacemaker that can both deliver electrical stimulation and monitor potassium levels, as described in U.S. Patent Publication 2006/0217771 A1, the contents of which are incorporated in their entirety. The dual capability of IMD 13 is particularly well suited for patients suffering from cardiac disease requiring pacing and concomitant kidney disease requiring monitoring of potassium concentrations for dialysis. The exemplary embodiment can deliver electric stimulation and record ECG data in the heart 15 of a patient. A right ventricular lead 17 has an elongated insulated lead body carrying one or more concentric coiled conductors separated from one another by tubular insulated sheaths. The distal end of right ventricular lead 17 is deployed in the right ventricle 19 of heart 15. Located adjacent to the distal end of the lead body are one or more pacing/sensing electrodes 20, which are configured to deliver cardiac pacing and are further configured to sense depolarizations of right ventricle 19. A fixation mechanism 22, such as tines or a screw-in element anchors the distal ends in right ventricle 19. The distal end also includes an elongated coil electrode 24 configured to apply cardioversion or defibrillation therapy. Each of the electrodes is coupled to one of the coiled conductors within the lead body. At the proximal end of right ventricular lead 17 is a connector 26, which couples the coiled conductors in the lead body to IMD 13 via a connector module 28. A right atrial lead 30 includes an elongated insulated lead body carrying one or more concentric coiled conductors separated from one another by tubular insulated sheaths corresponding to the structure of right ventricular lead 17. Located adjacent the J-shaped distal end of right atrial lead 30 are one or more pacing/sensing electrodes 32, which are configured to sense depolarizations and deliver pacing stimulations to right atrium 34.

Also shown in FIG. 2 is an elongated coil electrode 36 proximate to the distal end of right atrial lead 30, and located in right atrium 34 and the superior vena cava 38. At the proximal end of the lead is a connector 40, which couples the coiled conductors in right atrial lead 30 to IMD 13 via connector module 28. A coronary sinus lead 42 includes an elongated insulated lead body deployed in the great cardiac vein 44. The lead body carries one or more coiled conductors coupled to one or more pacing/sensing electrodes 46. Electrodes 46 are configured to deliver ventricular pacing to left ventricle 48 and are further configured to sense depolarizations of left ventricle 48. Additional pacing/sensing electrodes (not shown) may be deployed on coronary sinus lead 42 that are configured to pace and sense depolarizations of the left atrium 50. At the proximal end of coronary sinus lead 42 is connector 52, which couples the coiled conductors in coronary sinus lead 42 to connector module 28. An exemplary electrode element 54A is coupled to the distal end of a lead 56. Lead 56 carries one or more conductors separated from one another by insulated sheaths. A connector 58 at the proximal end of the lead couples the conductors in lead 56 to IMD 13 via connector module 28. In addition to connector module 28, IMD 13 has a housing 60 formed from one or more materials, including conductive materials such as stainless steel or titanium. Housing 60 can include insulation, such as a coating of Parylene® (poly(p-xylylene)) or silicone rubber, and in some variations, all or a portion of housing 60 can be left uninsulated. The uninsulated portion of housing 60 can serve as a subcutaneous electrode and a return current path for electrical stimulations applied via other electrodes.

Also shown in FIG. 2 is electrode element 54A that includes two electrodes 62A and 62B. At least one of electrodes 62A and 62B is deployed in or near test tissue and delivers stimulation to the tissue, while the other provides a return current path. The test tissue can comprise a collection of autologous or non-autologous cells that are sensitive to $[K^+]$. For example, the test tissue may be one of cardiac muscle, skeletal muscle, smooth muscle, nerve tissue, skin, or the like. The IMD 13 includes a sensor that detects the electromechanical response of the muscle to the stimulation delivered by electrodes 62A and 62B. The detected electromechanical response can include muscle tension, muscle strength, muscle density, muscle length and pressure generated by the muscled. The electromechanical sensor can be incorporated completely within the housing of IMD 13 or can be present outside the housing. Example sensors include optical sensors for observing mechanical responses and an accelerometer that responds to muscle movement. Further embodiments of the sensor for detecting an electromechanical response include pressure sensors and piezoelectric sensors.

In certain embodiments, the accelerometer can have a 3-axis accelerometer capable of separately detecting heart and lung sounds or movement and respiration rate. Heart and lung movement and respiration rate can indicate fluid volume overload. Any implantable device to obtaining ECG or other data can also have temperature sensing capabilities.

Figure 3:
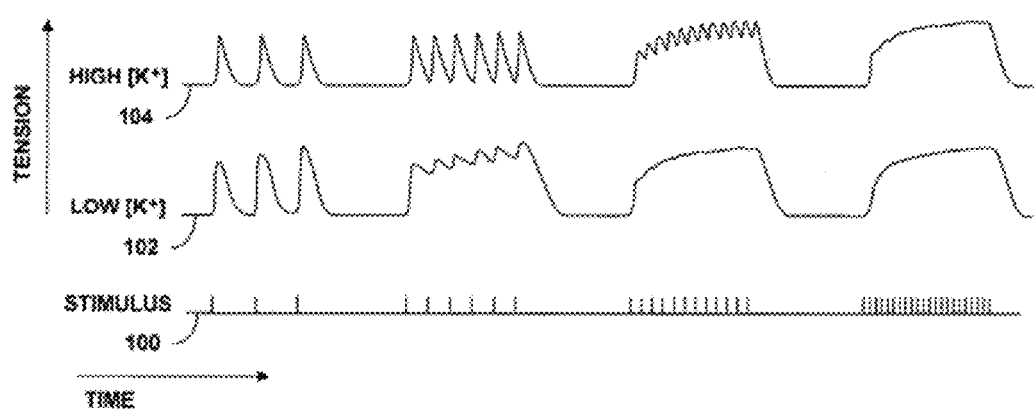
FIG. 3 is an illustrative mechanical response of muscle tissue to electrical stimulation depending upon a potassium environment.

FIG. 3 shows graphs of muscle force that illustrate exemplary techniques to determine a concentration of $[K^+]$ in extracellular fluid (ECF) as a function of the response of skeletal muscle to stimulations from an electrode element such as electrode elements 54A. Each stimulus can have an amplitude of about 2 to about 20 Volts, for example, and a pulse width of about 0.1 to 1.0 milliseconds. Stimulus line 100 shows the timing of stimuli delivered to the skeletal muscle via electrodes such as electrodes 62A-B of FIG. 2. Response line 102 depicts a response of skeletal muscle to the stimulations in an environment where [K$^+$] is low relative to concentrations in intracellular fluid (ICF). In other words, response line 102 depicts a response of skeletal muscle in a "normal" patient. By contrast, response line 104 depicts a response of skeletal muscle in a patient having elevated [K$^+$].

The frequency of stimuli can vary from about 10 to about 150 Hz. Muscle in a normal environment has longer duration contractions and can exhibit some summation. Muscle contractions in a lower [K$^+$] environment have a larger amplitude and have a longer duration than a high [K$^+$] environment. As described in FIG. 3, data obtained from electrical stimulation of potassium-sensitive tissue can be used to supplement the analysis of ECG data described herein.

Those skilled in the art will readily understand that the innovations disclosed here can readily be applied to data and electrical signals, including ECG data, obtained from non-implantable devices. For example, a plurality of electrodes can be placed on the skin of a subject. The plurality of electrodes can connected to a medical device for measuring electrical signals or a patch ECG device that transmits ECG by wireless telemetry to a receiver that can interpret the ECG data, such as the V-PATCH™ from VPMS Asia Pacific (Victoria, Australia). Electrical signals related to heart or lung activity and/or ECG data, regardless of source, can be used in conjunction with the embodiments described below.

Processing Unit and Computational Procedure

The physiological signals obtained by the medical device of the present invention are processed by a processing unit. The processing unit can be computing hardware that is disposed within the implantable medical device or external to the device. Alternatively, the processing unit can be external to the patient and receive the physiological data from the implantable medical device and process the data either in real time or at a later time. A computational procedure, which can be referred to as the forward computational procedure, is used to convert the physiological signals into disease scores, which will be described below in detail.

The processing unit can extract several details from each cardiac cycle. The complete cardiac cycle of the patient can be stored by the implanted medical device or the processing unit and associated with a time index. In certain embodiments, not every cardiac cycle of the patient is required to be stored by the medical system and associated with a time index. For example, every other cardiac cycle or every nth integer cardiac cycle can be processed. Alternatively, cardiac cycles that overlap certain time points can be analyzed since the time period of cardiac cycles depends upon heart rate. In some embodiments, the time indices of cardiac cycles indicate the chronological order of cardiac cycles, wherein adjacent time indexes are not restricted to immediately proximal cardiac cycles.

Table 1 lists various parameters or features that can be extracted from the ECG of each cardiac cycle. Each feature represents a scalar quantity that describes a feature of the ECG of the cardiac cycles.

TABLE 1

Features extracted from the electrocardiogram

| Feature | Definition |
| --- | --- |
| F1 | P-R interval |
| F2 | QRS width |
| F3 | Q-T interval or QT-dispersion |
| F4 | P-wave amplitude |
| F5 | P-wave peak |
| F6 | S-T segment depression |
| F7 | Inverted T-waves |
| F8 | U-wave observation |
| F9 | T-wave peak amplitude |
| F10 | Heart Rate Variability |

The scalar values for features F1 through F10 have diverse magnitudes and units which complicate arriving at a combination of the features into one or more risk scores that can be used to assess the potassium state of the patient. In particular, various features are typically reduced to a scalar quantity in the following units: P-R interval in time units, U-wave amplitude in potential units, S2 based upon a comparison with the feature QRS width in time units, Q-T interval in time units, P-wave amplitude in potential units per time unit, P-wave peak in potential units, and T-wave amplitude in potential units. Other features are indicated by a yes/no observations such as depression of S-T segment and inversion of the T-wave. Therefore, each of the features F1 through F10 can be converted to a value on a scale from 0 to 1 to allow direct comparison and or combination of features F1 through F10, which can herein be referred to as the common scale. Those skilled in the art will understand that scales having other ranges can be used.

Figure 4:
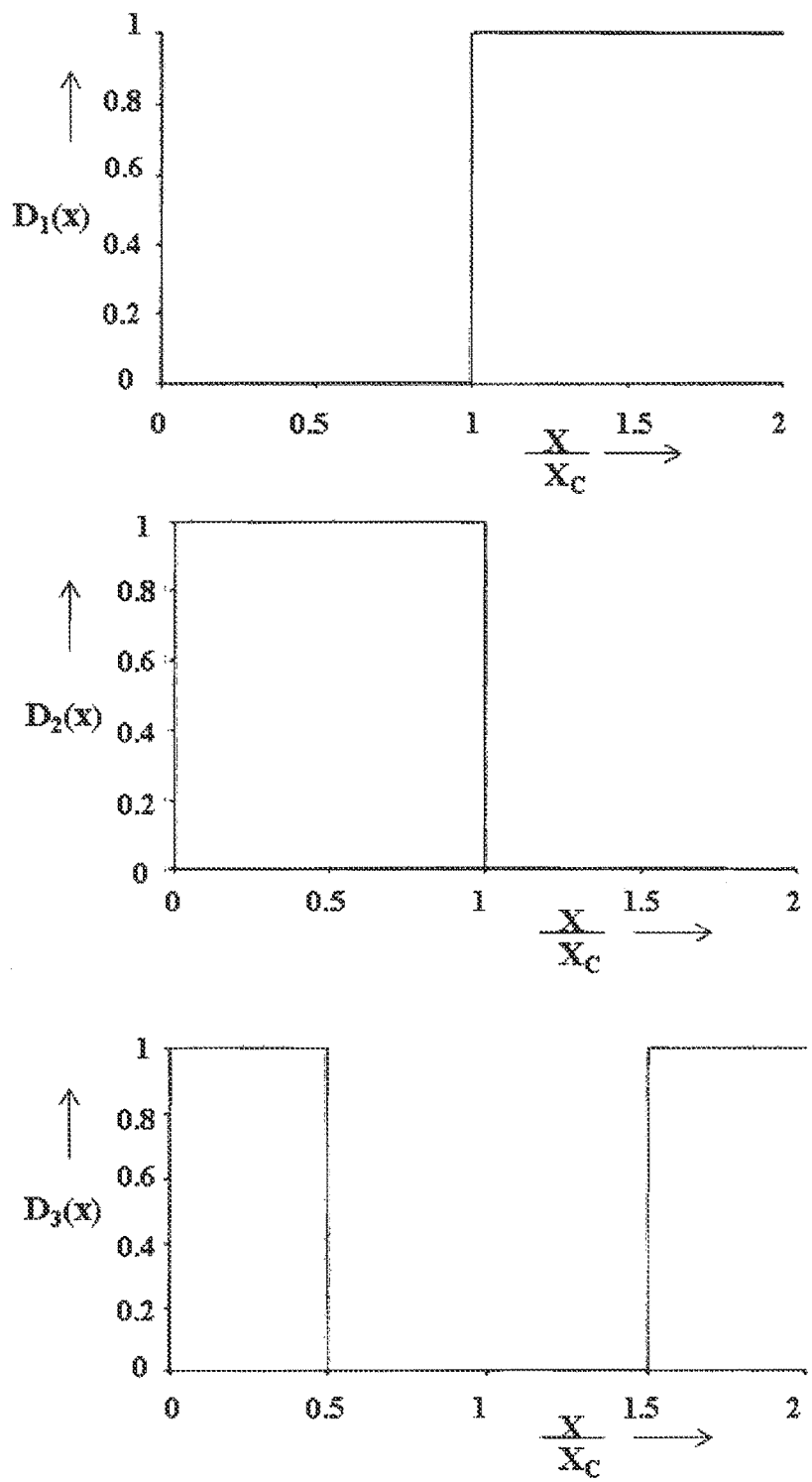
FIG. 4 is a graphical representation of discrete computational procedures to determine feature scores in accordance with some embodiments of the invention.
Figure 5:
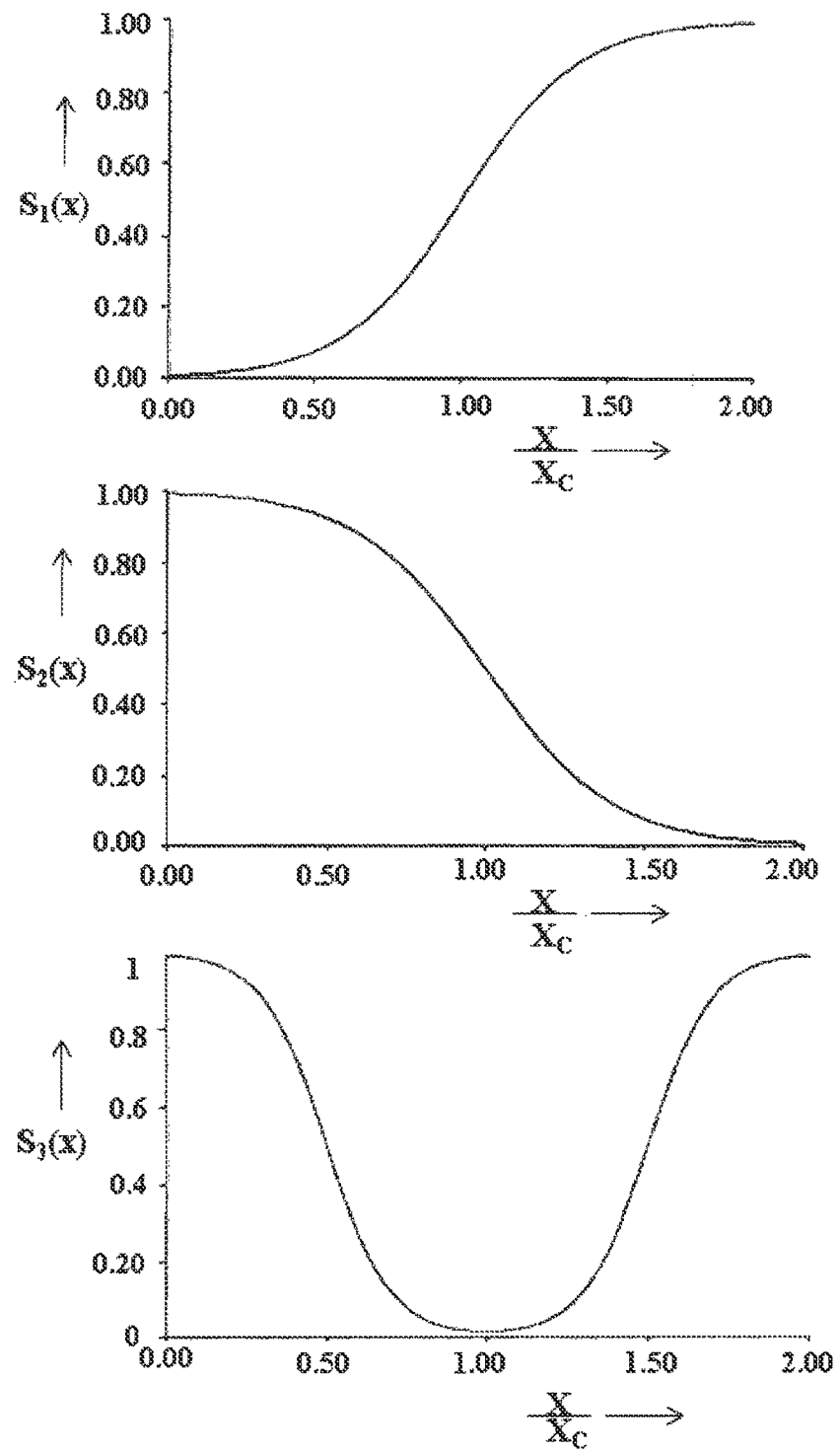
FIG. 5 is a graphical representation of continuous computational procedures to determine feature scores in accordance with some embodiments of the invention.

Table 2 shows various computational procedures that can be used to convert the features F1 through F10 to the common scale. Computational procedures D1 through D3 are discrete mathematical equations that result in an output of either 0 or 1. As shown in FIG. 4, computational procedure D1 indicates a value of 1 when a determinant or threshold $X_c$ is exceeded and otherwise indicates a value of 0. computational procedure D2 is similar except a value of 1 is indicated for a value less than determinant or threshold $X_c$. Computational procedure D3 provides a value of 1 when the value deviates from a set point by an amount $X_c$. The computational procedures S1, S2 and S3 are continuous mathematical functions with the possibility of any numerical value between 0 and 1. Computational procedures D1, D2 and D3 have the advantage of being easier to implement by a microprocessor because they only require a comparison of the argument X to a threshold value of $X_C$. However, the computational procedures D1, D2, and D3 do not provide any proportional response to the input. Computational procedures S1, S2 and S3 provide a more graded response, but impose a heavier computational burden on the microprocessor by either requiring a mathematical computation shown in Table 2 or the use of a look-up table. However, both discrete and continuous computational procedures are contemplated for use in the present invention. FIG. 5 presents exemplary plots for computational procedures S1, S2 and S3.

TABLE 2

Computational procedures used for the conversion of the features into scores

| Name | Mathematical Expression |
| --- | --- |
| D1 | $D_1(x, x_C) = \begin{cases} 1, & x > x_C \\ 0, & x \leq x_C \end{cases}$ |

TABLE 2-continued

Computational procedures used for the conversion of the features into scores

| Name | Mathematical Expression |
|---|---|
| D2 | $D_2(x, x_C) = \begin{cases} 0, & x > x_C \\ 1, & x \leq x_C \end{cases}$ |
| D3 | $D_3(x, x_C) = \begin{cases} 1, & |x| > x_C \\ 0, & |x| \leq x_C \end{cases}$ |
| S1 | $S_1(x, x_C, k) = \dfrac{1}{1 + e^{k(x_C - x)}}$ |
| S2 | $S_2(x, x_C, k) = \dfrac{1}{1 + e^{k(x - x_C)}}$ |
| S3 | $S_3(x, x_C, k) = \dfrac{1}{1 + e^{k(\frac{3}{2}x_C - x)}} + \dfrac{1}{1 + e^{k(x - \frac{x_C}{2})}}$ |

In one embodiment, computational procedures D1 and S1 are designed to indicate that the value of a feature is increasing, where an increased value is undesirable and will contribute to a disease risk score indicating an adverse condition. Computational procedures D2 and S2 represent the reverse situation where a decreased value indicates a contribution to a disease risk score and an adverse condition. Computational procedures D3 and S3 produce high scores indicative of an adverse condition when the feature deviates from a central value either by increasing or by decreasing.

Below is an example illustrating the use of the features and their conversion into raw scores using one of the discrete computational procedures D1 through D3. In this example, features F1 through F10 are as described in Table 1, and the value on the common scale are denoted with P1 through P10. That is, the list below exemplifies one embodiment for conversion of the scalar quantities for features F1 through F10 to value of 0 or 1 on the common scale using a computational procedure equivalent to one of D1 through D3.

If F1=P-R interval>200 msec, then P1=1, else P1=0;
If F2=QRS width>130 msec, then P2=1, else P2=0;
If F3=Q-T interval>220 msec, then P3=1, else P3=0 or if Standard Deviation of Q-T interval>20 msec, then P3=1, else P3=0;
If F4=P-wave amplitude<1 mV, then P4=1, else P4=0;
If F5=P-wave peak>1 mV/msec, then P5=1, else P5=0;
If F6=S-T segment depressed, then P6=1, else P6=0;
If F7=T-wave is inverted, then P7=1, else P7=0;
If F8=U-wave amplitude>2 mV, then P8=1, else P8=0;
If F9=T-wave peak amplitude>3 mV, then P9=1, else P9=0;
If F10=Heart Rate Variation (SDNN)<50 msec, then P10=1, else P10=0;

The correlation to the set of instructions described above can be expressed using the discrete computational procedures D1, D2 or D3 to compute the common scale values, which are shown below as P1 through P10:

P1=D1 (F1, 200 msec);
P2=D1 (F2, 130 msec);
P3=D1 (F3, 220 msec);
P4=D2 (F4, 1 mV);
P5=D1 (F5, 1 mV/msec);
P6=D2 (F6, 1.1 mV);
P7=D2 (F7, 0);
P8=D1 (F8, 2 mV);
P9=D1 (F9, 3 mV);
P10=D2 (F10, 50 msec);

Similar expressions for the raw scores P1 through P10 can be written using the continuous computational procedures S1 through S3 instead of D1 through D3. While not presented herein, the use of expressions S1 to S3 to generate common scale values being any real value between 0 and 1 is readily ascertainable by one having ordinary skill in the art upon applying a determinant $X_c$ and a factor k.

Afterwards, disease scores are calculated using the raw scores. Three examples are given below. In this case, DSL, DSH and DAR denote the disease scores for hypokalemic, hyperkalemic and arrhythmic outcomes respectively. Specifically, a higher value for DSL, DSH and DAR indicates an increased prevalence of the respective condition. WL1, WL5, WH2, WA1, etc. denote weighting coefficients. The weighting coefficients can be further refined as described below. In some embodiments, the weighting coefficients can be any number greater than or equal to zero.

$$DSL = WL1*P1 + WL6*P6 + WL7*P7 + WL8*P8 + WL10*P10 \quad \text{(Eq. 1)}$$

$$DSH = WL2*P2 + WL3*P3 + WL4*P4 + WL5*P5 + WL9*P9 + WL10*P10 \quad \text{(Eq. 2)}$$

$$DAR = WA1*P1 + WA2*P2 + \ldots + WA10*P10 \quad \text{(Eq. 3)}$$

For the calculation of the disease scores, weighting coefficients as well as the variables such as $X_C$ and k values will need to be determined. For the remainder of the discussions, these variables, weighting coefficients, $X_C$ and k, can be collectively denoted with the symbol M. These constants can be predetermined and adjusted as needed by the medical professionals attending the patient. Alternatively, the processing unit can adjust these constants based on the patient outcomes. In some embodiments, the weighting coefficients and value k can be set to 1, while the determinant value $X_C$ is as described above for each feature F1 through F10. That is, a disease score is calculated by a summation of individual weighed or non-weighted feature scores as shown in Equation 4, wherein $P_k$ is the feature score and $W_k$ is a weighting factor.

$$\text{Risk Score} = \sum_{k=1}^{n} W_k * P_k \quad \text{(Eq. 4)}$$

Figure 6:
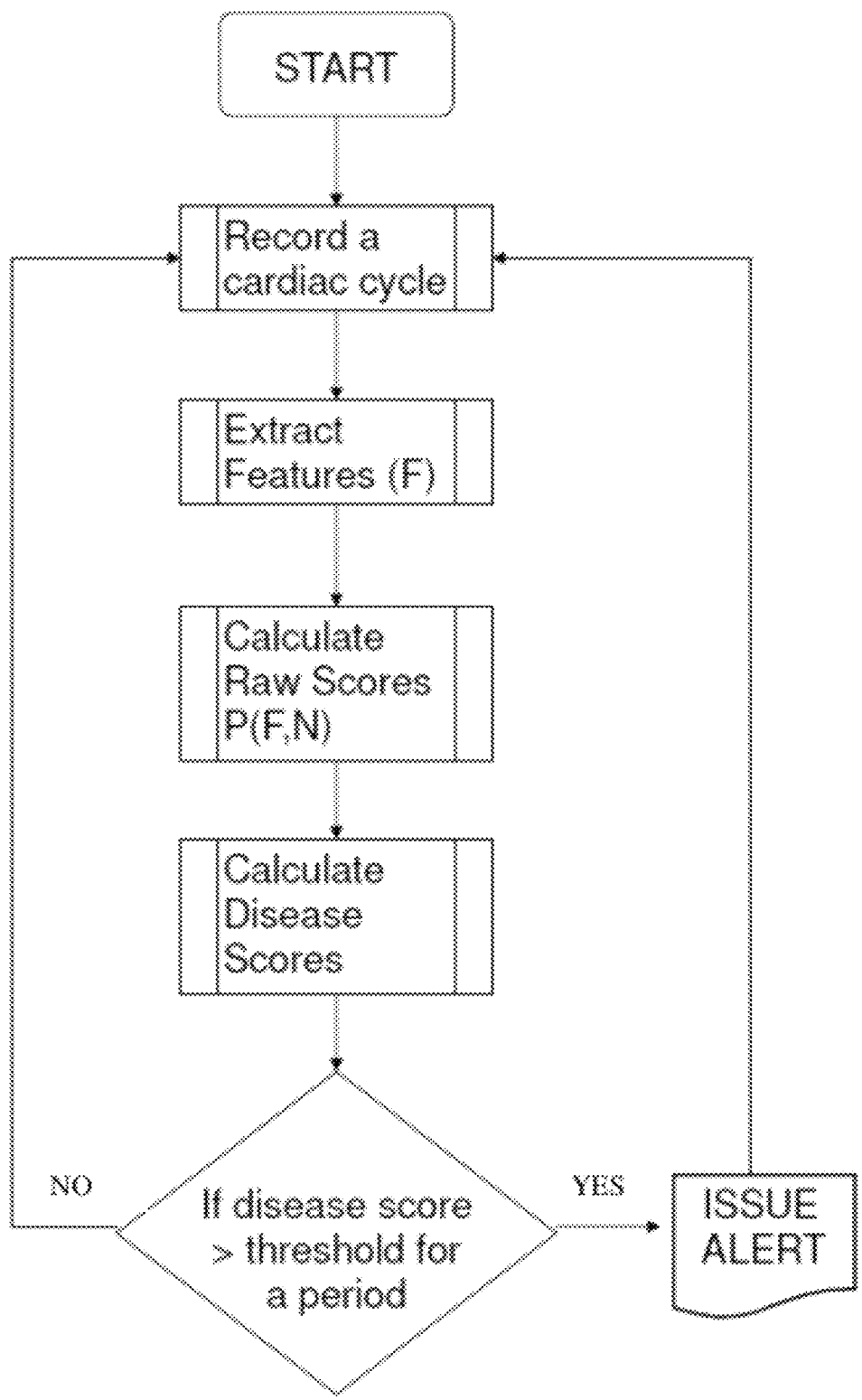
FIG. 6 is a flow chart of a process to issue an alert in accordance with some embodiments.

The flow chart for the overall forward computational procedure that monitors the patient is shown in FIG. 6 and outlined in steps below:

STEP 1: Record a cardiac cycle
STEP 2: Extract features F
STEP 3: Calculate raw scores P using features F and initial variables from M
STEP 4: Calculate disease scores D using raw scores P and weighting coefficients from M
STEP 5: If disease score>threshold for a period of time, issue alert
STEP 6: Go to step 1

Disease scores can be calculated for various conditions, including but not limited to, hypokalemia, hyperkalemia, arrhythmias, hospitalizations and acute heart failure.

Figure 7:
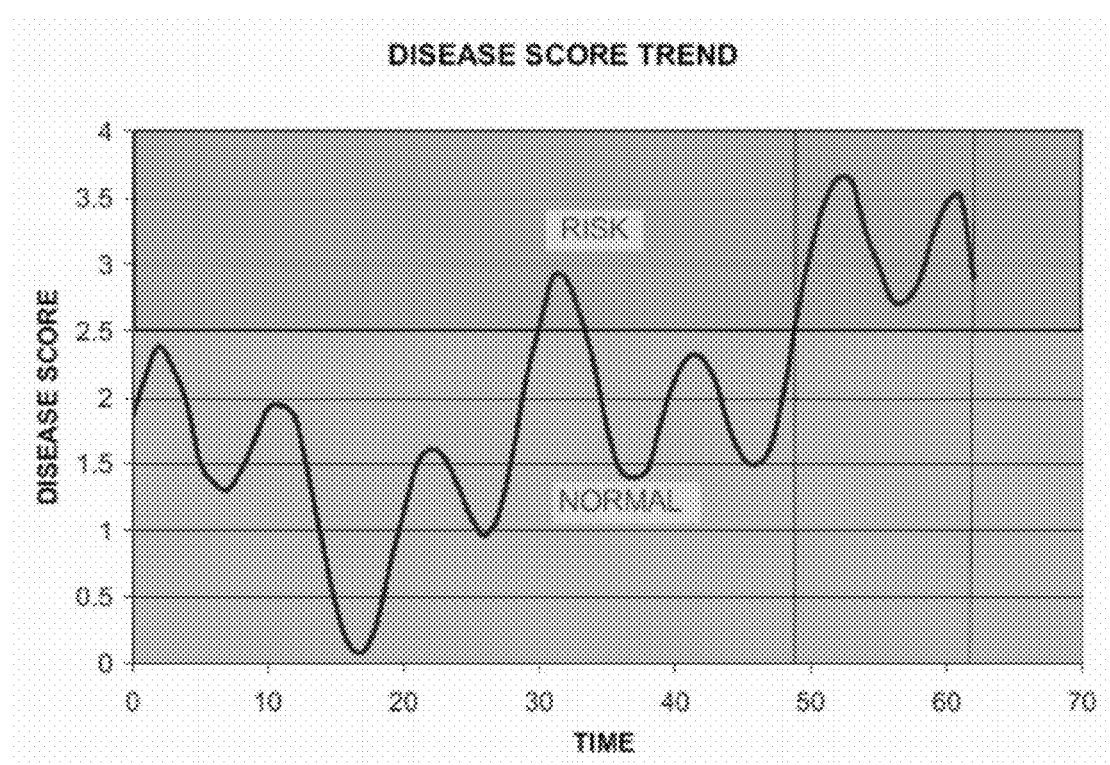
FIG. 7 is shows a disease risk score trend.

FIG. 7 shows an example trace for a disease score. In that case, the disease score exceeds the preset threshold of 2.5 at time index T=30, but subsequently returns back to a normal zone at time index T=34. Due to its short duration, this event does not trigger a warning. However, the disease score again enters into the risk zone at time index of T=49, and this time, it remains there for longer than 10 time indices resulting in the issuance of a warning. The selection of the threshold values as well as the minimum duration of risk can be chosen by the clinician depending on the conditions of the patient or could be determined by a backward computational procedure as described herein. Furthermore, the time duration before a warning is issued can be different for different disease scores. For example, for hyperkalemia time durations can be much longer than those for hypokalemia.

Figure 8:
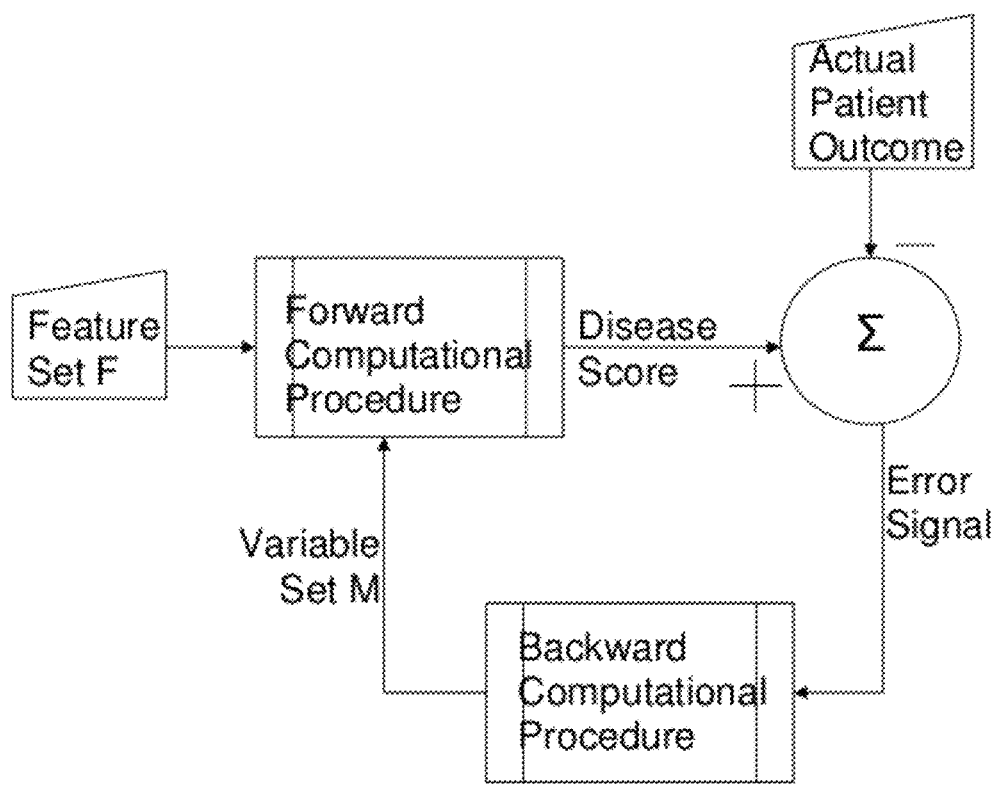
FIG. 8 shows the application of a correction to minimize error in accordance with some embodiments.

In certain embodiments, the controller works to identify the variables $X_c$, k as well as the weighting coefficients, and the thresholds and the time duration before a warning is issued, which are collectively called M. This is accomplished using a backward computational procedure wherein operation in the overall system is shown in FIG. 8. The feature set F is fed into the forward computational procedures as described above. Afterwards, the resulting disease score is compared to the actual patient outcome. The difference, called the error signal, is used to adjust the constant set M, which is used in the future execution of the forward computational procedures. For example, if the disease score and the patient outcome are the same, then the error signal would be zero, indicating that there is no reason to alter the constants. On the other hand, if there is discrepancy between the disease score and the actual patient outcomes, then the error signal would be a non-zero value, which in turn will drive the backward computational procedure to alter the constant set M. The backward computational procedures can be constructed using any of the many known statistical and signal processing methods such as the least squares and steepest descent.

Communication System

Figure 9:
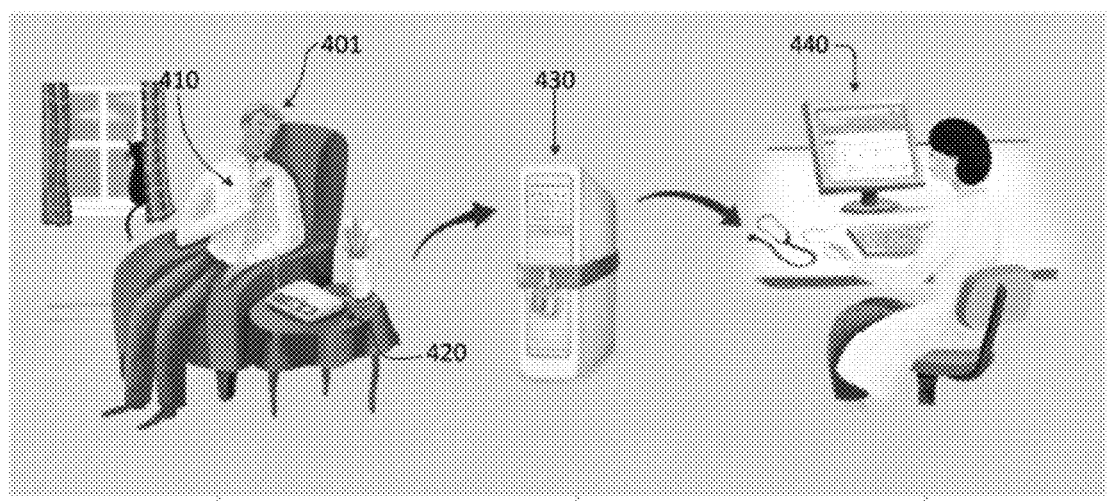
FIG. 9 shows a monitoring of a medical system or device in accordance with some embodiments.

The communication system allows the transfer of data as well as the disease scores and the variables from set M between the implanted medical device and the external devices for monitoring the patient 401 as shown in FIG. 9. In particular, the implanted medical device or external medical device 410 can be in wireless communication with a local monitor 420 located in the vicinity of the patient. The local monitor 420 can then communicate with either a local computer that can serve as a control processor for interpreting electrical signals from the patient, or the electrical signals from the patient can be transmitted to a remote control processor 430. In any scenario, a clinician 440 can monitor the control processor, provide the results of clinical observations or lab tests, or adjust the set M used in disease score calculation or modify thresholds or time periods for generating an alert. When an alert is generated as described below, the patient 401 can be made aware through a signal (e.g. audio, visual, etc.) from local monitor 420 and a clinician monitoring the control processor 430 can be made aware of any patient having an alert.

The implanted medical device and/or the local monitor can share and transmit data and instructions using any known method of wired or wireless telemetry. For example, a WMTS driver in any device can provide an interface for communication via protocols, such as conventional RF ranges allocated by Federal Communications Commission (FCC) for Wireless Medical Telemetry Service (WMTS). A 802.11 driver in any device can support an 802.11 wireless communication protocol such as 802.11a, 802.11b, or 802.11g. Similarly, a Bluetooth driver can support RF communications according to the Bluetooth protocol. Any device can also include CDMA and GSM drivers for supporting cellular communications according to the code division multiple access (CDMA) protocol, or the Global System for Mobile Communications (GSM) protocol, respectively. Software Applications can invoke Network Protocols to make use of these drivers for communication with the local monitor 420 and/or the control processor 430. Network Protocols in any device can implement a TCP/IP network stack, for example, to support the Internet Protocol or other communication protocols. The preceding is merely exemplary of methods of communication that can be used by an implanted medical device 410, the local monitor 420 or the remote control processor 430 wherein one of ordinary skill will understand that many ways of performing the objectives of the invention are known within the art.

Those skilled in the art will readily understand that the communication system can transmit other data in addition to the specific disease score data disclosed herein. Rather, many other patient parameters can be observed with sensors or inputted to evaluate the dialytic status of the patient, which can include both the effectiveness of dialysis treatment in replacing natural kidney function or complications due to dialysis treatment, such as undesirable changes in potassium ion levels. Data that can be collected and transmitted by the communication system include, but is not limited to, 1) Non-potassium electrolytes and biomarkers such as sodium and calcium; 2) metabolites such as urea, glucose and lactate; 3) hemodynamic parameters such as pulmonary artery pressure, left atrial pressure, right atrial pressure, left ventricular end diastolic pressure, $O_2$ saturation, and cardiac output; 4) serum biomarkers such as creatinine, albumin, beta-2-microglobin and nGAL; 5) ECG parameters and features; 6) cardiac, skeletal contraction and/or lung data obtained from accelerometer sensors; and 7) values inputted by the patient regarding physical condition.

As will be discussed in greater detail below, ECG parameters and features can be used to calculate specific risk scores. However, additional data can be used to evaluate an overall dialytic clinical risk score (DCRS). The DCRS can be evaluated qualitatively by a physician or a clinician to access the overall status of the patient. In other embodiments, a DCRS can be calculated in an automated fashion using an algorithm and the resulting information evaluable by a physician or a clinician, where a monitoring physician or clinician can be made aware of patients evaluated to have a DCRS that requires further evaluation in an automated fashion. That is, a change in DCRS can be used to trigger an automated alert for further evaluation by a physician or clinician. The further exploration by a physician or clinician can be assisted by the division of data components between differential diagnostic dashboards, wherein the physician or clinician can be directed to a specific diagnostic dashboard that contributed to the alert, for example, hyperkalemic, hyperglycemic, hypervolemic component, etc.

In certain embodiments, the DCRS does not need to include components from all data known about the patient. Rather, the DCRS can be calculated using a skip-logic method, wherein only certain parameters contribute to the score based upon certain criteria. For example, the measurement of a high pulse rate may trigger the calculation of DCRS based upon certain additional parameters such as $O_2$ saturation, respiration rate, blood glucose, contractile strength (as measured by accelerometer data), and electrolytes while excluding other parameters. As such, the basis for a DCRS score can change based upon specific patient data. Still further, in certain embodiments ECG data and/or heart contractile strength data can provide an indication of sodium ion concentration in the blood serum or in extracellular fluids.

Figure 10:
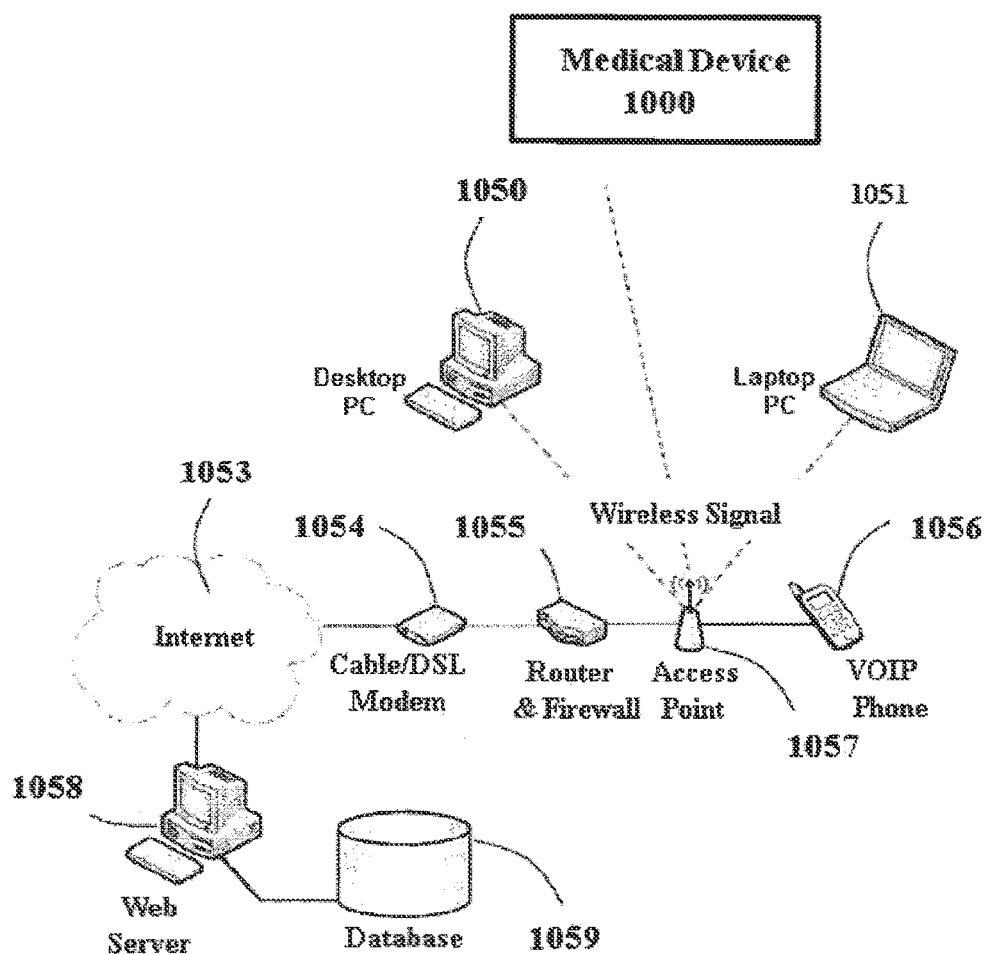
FIG. 10 shows an additional system for monitoring a medical device in accordance with some embodiments.

As discussed above, FIG. 9 shows a communication system in accordance with some embodiments where an implanted or external medical device 410 can be in wireless communication with a local monitor 420 located in the vicinity of the patient that can relay data from the medical device 410 to a remote process 430 and/or a clinician 440. FIG. 10 presents additional embodiments for the communication of data and other information from and to a medical device including medical devices for monitoring an ECG or other electrical signals, including internal or external medical devices. The medical device can also include sensors or other medical devices for measuring any patient parameter including the parameters discussed above such as electrolytes, hemodynamic parameters, serum biomarkers, cardiac or skeletal muscle response and respiration, or patient-reported information.

In FIG. 10, a medical device 1000, which can be any of the medical devices or sensors discussed above, is in wireless communication with an access point 1057 can be a local monitoring device or a Wi-Fi router or other device that provides networking capabilities. The identity of the access point 1057 is not particularly limit and can include any device capable of relaying data such as smart phone or an iPad® device (not shown). The medical device 1000 through the access point 1057 can transmit or receive data to or from a remote device via a computer network, pager network, cellular telecommunication network, and/or satellite communication network, or via an RF link such as Bluetooth, WiFi, or MICS or as described in U.S. Pat. No. 5,683,432 "Adaptive Performance-Optimizing Communication System for Communicating with an Implantable Medical Device" incorporated herein by reference in its entirety, wherein there is no requirement for the electronic controller to be implanted within the patient.

In certain embodiments, a telemetry circuit that enables programming of the medial device 1000 by means of a 2-way telemetry link. Uplink telemetry allows device status and diagnostic/event data to be sent to a clinician or physician or another party for review to track the treatment of a patient. Known telemetry systems suitable for use in the practice of the present invention are contemplated by the invention. Such 2-way communication with the medical device 1000 is typically done via a bi-directional radio-frequency telemetry link, such as the CareLink™ system (Medtronic, Inc., Minneapolis, Minn.). Further, a general purpose computer or any other device having computing power such as a smart phone, iPad® or like device.

As shown in FIG. 10, in some embodiments, transmission of data to and from the medical device 1000 can be accomplished through a number of different external devices. Through the access device 1057, different types of devices running applications for sending and receiving data from the medical device 1000 can be used, such as a desktop 1050 or laptop PC 1051 or a cellular phone or smart phone device 1056. In some embodiments, data can be transmitted over the internet 1053 via a local router 1055 and/or modem 1054 for placement on a secure web server 1058 and associated database 1059. The web server 1058 can be accessed by the patient and/or a physician or clinician to receive or send data to the medical device 1000.

Various telemetry systems for providing the necessary communications channels between an electronic controller and a medical device have been developed and are well known in the art, for example, telemetry systems suitable for the present invention include U.S. Pat. No. 5,127,404, entitled "Telemetry Format for Implanted Medical Device"; U.S. Pat. No. 4,374,382, entitled "Marker Channel Telemetry System for a Medical Device"; and U.S. Pat. No. 4,556,063 entitled "Telemetry System for a Medical Device," which are all incorporated herein by reference. In addition to transmission over the internet, any device shown in FIG. 10 can also directly share data with a 802.11 driver to support 802.11 wireless communication protocol such as 802.11a, 802.11b, or 802.11g. Similarly, a Bluetooth driver can support RF communications according to the Bluetooth protocol. Any device can also include CDMA and GSM drivers for supporting cellular communications according to the code division multiple access (CDMA) protocol, or the Global System for Mobile Communications (GSM) protocol, respectively.

Disease Scoring

Figure 11:
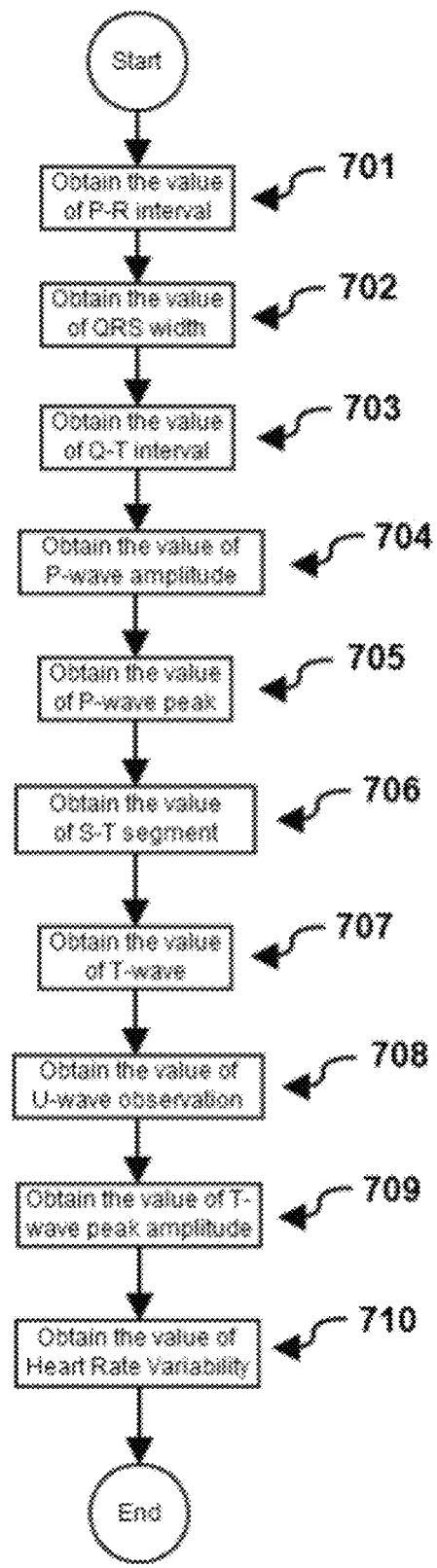
FIG. 11 shows the acquisition of feature values for an ECG.

The process for calculating a disease risk score by the processor unit will now be described with particularity. FIG. 11 presents a flowchart for a process to monitor the real-time electrical signals of the body of a subject that extracts values of different components from the electrical signals including PR interval, QRS width, QT interval, P wave amplitude, P wave peak, ST segment, T waves, U wave amplitude, T wave peak amplitude and heart rate variance corresponding to features F1 through F10 as discussed above. The sequence of determining values for Features F1 through F10 can be different than presented in FIG. 11; however, FIG. 11 presents the order of feature determination from an ECG associated with a particular time index in accordance with one embodiment. In step 701, the processor unit determines the value of the P-R interval from an ECG of one cardiac cycle associated with a time index. In step 702, the processor unit determines the value of the QRS width from the ECG of one cardiac cycle associated with the time index. In step 703, the processor unit determines the value of the Q-T interval from the ECG of one cardiac cycle associated with the time index. In step 704, the processor unit determines the value of the P-wave amplitude from the ECG of one cardiac cycle associated with the time index. In step 705, the processor unit determines the value of the P-wave peak from the ECG of one cardiac cycle associated with the time index. In step 706, the processor unit determines the value of the S-T segment from the ECG of one cardiac cycle associated with the time index. In step 707, the processor unit determines T wave inversion from the ECG of one cardiac cycle associated with the time index. In step 708, the processor unit determines the value of the U-wave amplitude from the ECG of one cardiac cycle associated with the time index. In step 709, the processor unit determines the value of the T-wave peak from the ECG of one cardiac cycle associated with the time index. In step 710, the processor unit determines the value of the heart rate variance from the ECG of one cardiac cycle associated with the time index.

Figure 12:
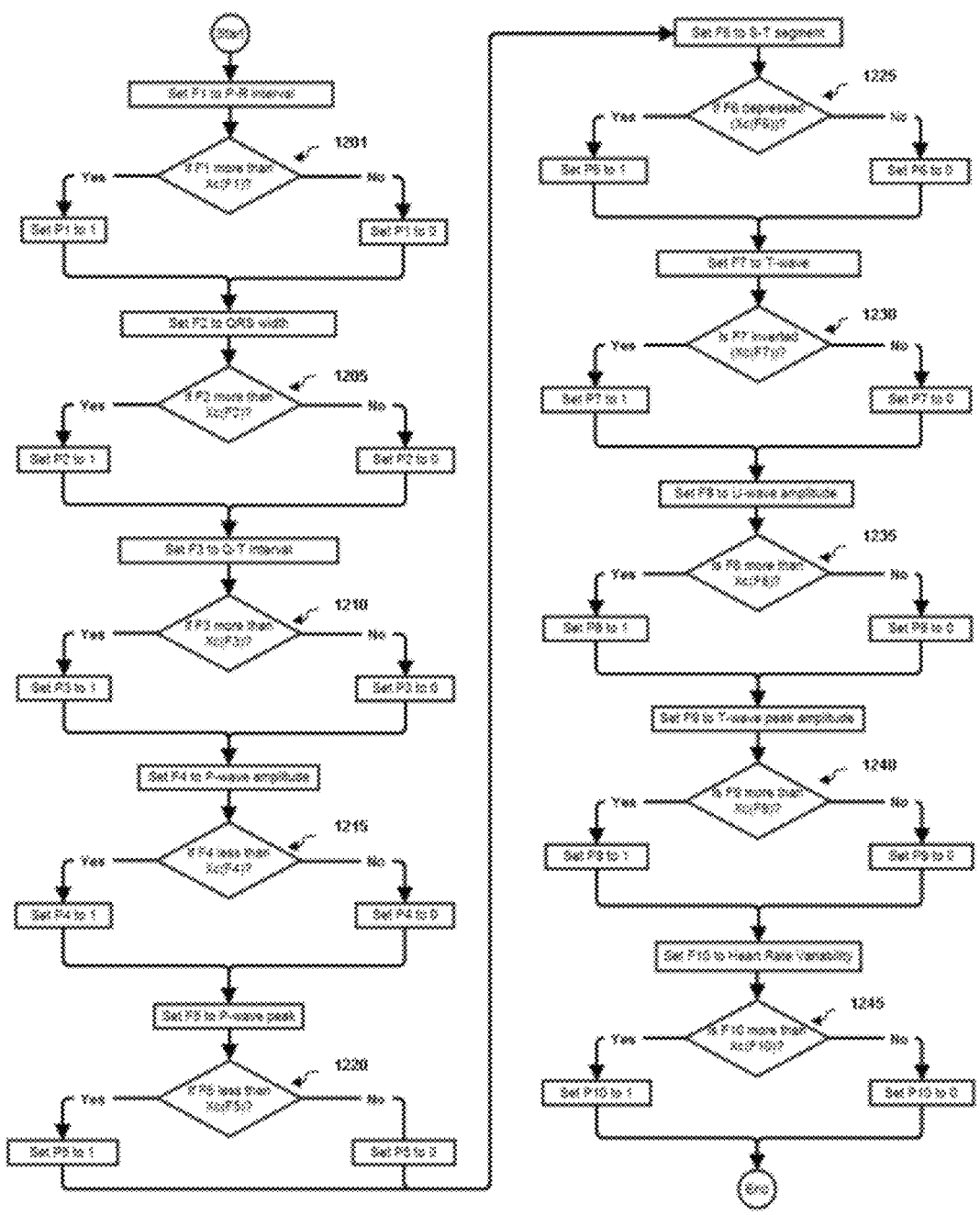
FIG. 12 shows a process for setting feature scores on a common scale in accordance with some embodiments.

In FIG. 12, a process for transforming the values for features F1 to F10 to scores on the common scale is shown. FIG. 10 shows the conversion performed using one of the discrete computational procedures D1 through D3 as described above. Using computational procedures D1 through D3, a determinant $X_c$ within set M must be determined. As described above, Xc can be set to initial values within set M or can be refined values as determined by application of the backwards computational procedure. In additional embodiments, the set M can include a value k to allow for use of one of the continuous computational procedures S1 through S3, as described above, for generation of one or more of the common scale values P1 through P10. In any scenario, the values for features F1 through F10 can be used to generate values P1 though P10 on the common scale provided that at least a determinant $X_c$ is set in set M for each of features F1 through F10. That is, each feature F1 through F10 is compared to a determinate $X_c$ for a specific feature, which can be denoted $X_c(F1)$, $X_c(F2)$, $X_c(F3)$, $X_c(F4)$ . . .

Xc(F10). Similarly, the value k associated with any specific feature can be referenced by similar nomenclature: k(F1), k(F2), k(F3), k(F4) . . . Xc(F10).

In step 1201 in FIG. 12, the value F1 for the P-R interval is compared to determinant $X_c(F1)$ to set the value of S1 to 0 or to set the value of S1 to 0 using a discrete computational procedure. In some embodiments, the determinant $X_c(F1)$ has a value of 200 msec. In step 1205, the value F2 for QRS width is compared to determinant $X_c(F2)$ to set the value of S1 to 0 or to set the value of S1 to 0 using a discrete computational procedure. In some embodiments, the determinant $X_c(F2)$ has a value of 130 msec. In step 1210, the value F3 for Q-T interval is compared to determinant $X_c(F3)$ to set the value of S1 to 0 or to set the value of S1 to 0 using a discrete computational procedure. In some embodiments, the determinant $X_c(F3)$ has a value of 220 msec. In step 1215, the value F4 for P-wave amplitude is compared to determinant $X_c(F4)$ to set the value of S1 to 0 or to set the value of S1 to 0 using a discrete computational procedure. In some embodiments, the determinant $X_c(F4)$ has a value of 1 mV. In step 1220, the value F5 for P-wave peak is compared to determinant $X_c(F5)$ to set the value of S1 to 0 or to set the value of S1 to 0 using a discrete computational procedures. In some embodiments, the determinant $X_c(F5)$ has a value of 1 mV msec−1. In step 1225, the value F6 for S-T segment is compared to determinant $X_c(F6)$ to set the value of S1 to 0 or to set the value of S1 to 0 using a discrete computational procedure. In some embodiments, the determinant $X_c(F6)$ is a yes or no determination of whether S-T segment is depressed. In step 1230, the value F7 for T-wave inversion is compared to determinant $X_c(F7)$ to set the value of S1 to 0 or to set the value of S1 to 0 using a discrete computational procedure. In some embodiments, the determinant $X_c(F7)$ is a yes or no determination of whether the T-wave is inverted. In step 1235, the value F8 for U-wave amplitude is compared to determinant Xc(F8) to set the value of S1 to 0 or to set the value of S1 to 0 using a discrete computational procedure. In some embodiments, the determinant $X_c(F8)$ has a value of 2 mV. In step 1240, the value F9 for T-wave peak is compared to determinant $X_c(F9)$ to set the value of S1 to 0 or to set the value of S1 to 0 using a discrete computational procedure. In some embodiments, the determinant $X_c(F9)$ has a value of 1 msec. In step 1245, the value F10 for heart rate variability is compared to determinant $X_c(F10)$ to set the value of S1 to 0 or to set the value of S1 to 0 using a discrete computational procedure. In some embodiments, the determinant $X_c(F10)$ has a value of 50 msec.

After the assignment of all set values, a DSL disease score is calculated for the time index using Eq. 1 described above. In some embodiments, the weighting coefficients WL1, WL2, etc. are set to 1. In other embodiments, the weighting coefficients WL1, WL2, etc. are set to a value found in the current set M. Similarly, a DSH disease score is calculated for the time index using Eq. 2 described above. In some embodiments, the weighting coefficients WL1, WL2, etc. are set to 1. In other embodiments, the weighting coefficients WL1, WL2, etc. are set to a value found in the current set M. Further a, a DAR disease score is calculated for the time index using Eq. 3 described above. In some embodiments, the weighting coefficients WA1, WA2, etc. are set to 1. In other embodiments, the weighting coefficients WA1, WA2, etc. are set to a value found in the current set M.

The DSL disease score calculated by Eq. 1 indicates the presence of a hypokalemia condition and the DSH disease score calculated by Eq. 2 indicates the presence of a hyperkalemia condition. The presence of hypokalemia condition and hyperkalemia condition are mutually exclusive. As such, in some embodiments the processor unit is configured to issue a warning for hypokalemia if requisite conditions are satisfied prior to issuing a warning for hyperkalemia if requisite conditions are satisfied.

Figure 13:
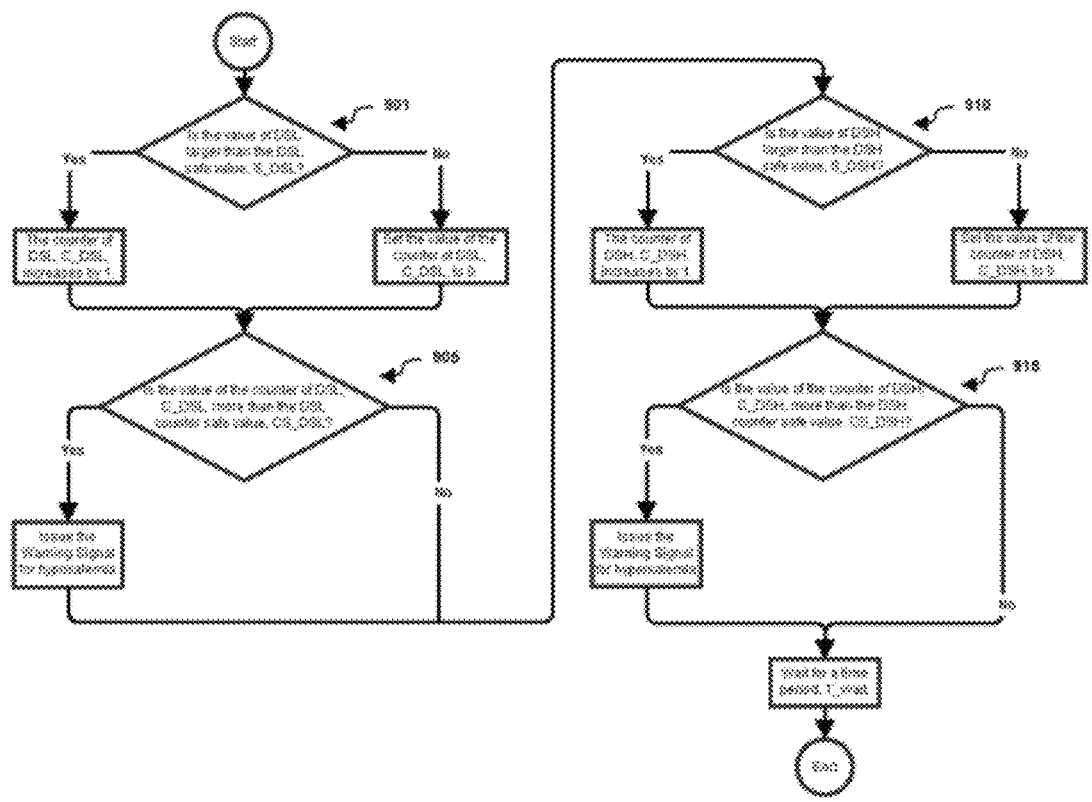
FIG. 13 shows a process for issuing an alert for hypokalemia or hyperkalemia in accordance with some embodiments.

FIG. 13 shows an embodiment for determining if conditions are satisfied for issuing an alert for hyperkalemia or hypokalemia. In FIG. 13, a warning is issued if a DSL risk score or a DSH disease score exceeds a threshold for a set number of consecutive time indices. The threshold for DSL disease score or DSH disease score can be separately set and can be refined as part of set M with the backward computational procedures. As explained above, a DSL disease score and DSH disease score are set for each time index. The time period between adjacent time indices is known by the processor unit. As such, a certain set of contiguous time indices can be associated with a specific time period by the processor unit.

In step 901, the DSL disease value for a time index is compared to a threshold for DSL disease score. If the threshold is exceeded, a counter for DSL disease score (C_DSL) is incremented by an integer value of 1. If the threshold is not exceeded, then the counter C_DSL is reset to 0. In step 905, the current count of the counter for DSL disease score (C_DSL) is compared to an alert time period which can be indicated by the C_DSL exceeding a safe value CS_DSL. For example, if the alert time period is 5 minutes and 15 seconds separate adjacent time indices, then the safe value CS_DSL for the counter can be set to 20, where an alert for hypokalemia is issued in step 905 if C_DSL exceeds CS_DSL. In step 910, the current count of the counter for DSH disease score (C_DSH) is incremented by an integer value 1 if the threshold for DSH disease score is exceeded. If the threshold for DSH disease score is not exceeded for a time index, then the counter C_DSH is reset to 0. In step 915, the current count of the C_DSH counter is compared to a safe value CS_DSH. An alert for hyperkalemia is issued in step 915 if the counter C_DSH exceeds CS_DSH.

Those skilled in the art will readily understand that the steps shown in FIG. 12 represent one embodiment for determining if a DSL disease score and/or DSH disease score exceed a threshold value for a significant period to warrant that an appropriate alert be issued. Those skilled in the art will readily recognize that whether the DSL disease score or DSH disease score exceeds a threshold a sufficient number of times or for a sufficient period of time can be evaluated by additional or alternative means without departing from the invention. As an example, step 901 can be modified such that the counter for DSL disease score (C_DSL) is not reset upon evaluation of a time index that does not have a DSL disease score below the threshold. As an alternative, the C_DSL counter can be set to zero if a certain prior number of time indices or time indices corresponding to a set period of time fall below the threshold for the DSL disease score. For example, the processor unit can be instructed to reset C_DSL to zero if all of the time indices from the last 3 minutes (or another appropriate time period) were below the threshold. As such, the observation of only a few time indices below the threshold will not reset the counter C_DSL nor increment the counter C_DSL by an integer value of 1; rather, the count value of C_DSL can be left unchanged until the DSL disease score is observed below a threshold for an intervening period of time. As such, the decision to issue an alert for hypokalemia in step 905 can be based upon a moving average time frame for a number of time indices that exceed the threshold value during a defined time window.

Step 910 for determining a count for C_DSH can be modified in the same manner as for C_DSL in step 901. Further, a counter for the DAR disease (C_DAR) score exceeding a threshold can be established in the same manner as for C_DSL and C_DSH with parallel protocols for deciding when the C_DAR has reached a requisite level to issue an alert for arrhythmia.

Those skilled in the art will understand that the threshold to which any of the described risk scores are compared to for the purposes of issuing an alert, as for example as in FIG. 12, is not required to be a fixed value. In some embodiments, the threshold can be a fixed value, which, for example, can be correlated to specific levels of potassium ions or other electrolytes. In other embodiment, the threshold can vary and can be recalculated during the course of monitoring of a patient. For example, the system can observe an average risk score for the patient over a period of time or a time window to establish a baseline risk score value. In some instances, the baseline risk score value can be established during a period defined by a patient user and/or a clinician. In other instances, the baseline risk score value can be determined periodically by calculating an average risk score during a period of time where no alarms or adverse conditions are reported. In some embodiments, the baseline risk score can be established over a period from 3 hours to about 2 weeks. In other embodiments, the baseline risk score can be established over a period from about 3 hours to about 1 week, from about 1 week to about 2 weeks, from about 3 days to about 2 weeks, from about 3 days to about 1 week or from about 1 day to about 2 weeks.

Once a baseline risk score for a patient is established, the threshold for any risk score described herein can be calculated based upon the baseline risk score. As discussed above, when a risk score (e.g. DSL, DSH, DAR) exceeds a threshold for the risk score, then a counter for the respective risk score (e.g. C_DSL, C_DSH, C_DAR) advances and an alert can be issued when the counter value exceeds a limit. The threshold to which a risk score is compared for purposes of advancing the corresponding counter can be a floating value that changes based upon the determined baseline risk score. In some embodiments, the threshold can be set at a value that is a certain percentage greater than the baseline risk score. In one embodiment, a threshold for a risk score can be any of from about 10 to about 100%, from about 15 to about 50%, from about 15 to about 40%, from about 20% to about 60% or from about 25% to about 50% greater than the determined baseline risk score. In other embodiments, a threshold for a risk score can be set as a specific absolute value over the determined baseline risk score.

Since the baseline risk score for each risk score DSL, DSH and DAR can be adjusted, a patient can be evaluated as being at risk as a result of a relative change in risk score since the last time the baseline risk score was calculated. As such, baseline risk scores and thresholds can account for patient-to-patient variability as well as gradual changes in patient ECG parameters that do not represent a greater susceptibility to hyperkalemia/hypokalemia or arrhythmias. That is, it is possible for the baseline risk score of patients to change overtime due to benign causes that do not represent an increased risk for hyperkalemia/hypokalemia or arrhythmias, where such changes are gradual over time. As described above, the system can account for such drift in baseline risk score, where an alarm is only triggered in response to a significant increase in risk score over a relatively short period of time rather than based upon an absolute risk score value.

Backward Computational Procedure

In FIG. 8, the features set to the common scale are provided in 501 for operation on by the forward computational procedure 505. As described above, the forward computational procedure is any of Equations 1 through 3 to calculate a disease risk score DSL, DSH and/or DAR. In step 510, periodic clinical data regarding measured patient condition can be supplied to the system. For example, information regarding serum potassium obtained from standard laboratory tests can periodically be inputted to the control processor and compared to the disease risk score generated at the time serum potassium was measured.

The threshold set for the disease risk score is correlated with an expected potassium serum level. A discrepancy between disease risk score and the clinical data from step 510 can result in an error value which is produced by the summation step ("sigma") in step 515. When an error is detected in step 515, the backward computational procedure can be applied in step 520 to adjust the set of weight, determinant ($X_c$) and/or k values in the set M used by the forward computational procedure to generate risk scores. The new set M can be used in the forward computational procedure in step 505 going forward to refine the set M in an iterative fashion.

Each of Equations 1 through 3 is a linear combination of the product of a weighting factor and a feature value (P) on the common scale. Refinement of determinant $X_c$ and/or k value will lead to a change in the feature value (P) that will modify the calculated disease score. Likewise, modification of the weighting factors will modify the calculated disease score. A disease score such as DSL in Equation 1 is a linear summation of 5 product terms. Linear functions and computational procedures are susceptible to refinement by known statistical techniques such as least squares regression fit and steepest descent. Such statistical techniques typical require the observation of more data points than the number of variable to be refined for an accurate refinement. In least square refinement, variables are brought to a state of best fit with the number of observations by reducing the value of the sum of squares of residuals, where the residuals are the distance from a best fit value and an observed value. Here, the summation of the squares of residuals between the calculated disease risk score calculated with refined set M and the observed potassium serum level can be performed.

In some embodiments, the backward computational procedures to refine set M is only applied to refining one of the weighting factors, the determinant $X_c$ or the value k. In other embodiments, each of weighting factors, the determinants $X_c$ and the values k are separately refined to generate separate sets M. That is, for example, weighting factors are refined without modifying determinants $X_c$ and the values k; determinants $X_c$ are refined without modifying weighting factors and the values k; and the values k are refined without modifying the determinants $X_c$ and the weighting factors. The refined set M having the best fit can be maintained and carried forward to step 505.

In some embodiments, the amount of refinement can be restrained to prevent over refinement or refinement error. In some embodiments, the amount of refinement to the determinants Xc can be restrained. For example, the amount that determinants Xc can be modified from their initial values can be limited to one of about 30% or less, about 25% or less, about 20% or less, about 15% or less, about 10% or less or about 5% or less. Similarly, the amount of the weighting factors can be restrained to not exceed a certain value. In some embodiments, the weighting factor can be limited to not exceed one or more from about 2.5, about 2 and about 1.5.

Chronic Monitoring of Electrolytes and pH

A patient can be monitored in a chronic fashion for changes in electrolytes in addition of potassium ion or in a manner to supplement monitoring by ECG data only. Similarly, the patient can be monitored for changes in pH.

One goal of hemodialysis, ultrafiltration, and like treatments is to ensure that the patient's blood pH and electrolyte concentrations are within acceptable ranges. Typical ranges of pH and blood electrolyte concentration that are desired during or following a blood fluid removal session are provided in Table 3 below. As indicated in Table 3, concentrations of various acids or bases (or salts or hydrates thereof) are often important in determining the pH of blood. Accordingly, some typical target concentrations of such acids or bases are presented in Table 3.

TABLE 3

Typical target ranges for pH and electrolytes
(ref. Medical Surgical Nursing, 7<sup>th</sup> Ed., 2007)

|  | Target Range |
|---|---|
| pH | 7.35-7.45 |
| Phosphate | 2.8-4.5 mg/dL |
| Bicarbonate | 22-26 mEq/L |
| $Cl^-$ | 96-106 mEq/L |
| $Mg^{2+}$ | 1.5-2.5 mEq/L |
| $Na^+$ | 135-145 mEq/L |
| $K^+$ | 3.5-5.0 mEq/L |
| $Ca^{2+}$ | 4.5-5.5 mEq/L |

In hemodialysis sessions, a patient's blood is dialyzed against a dialysate through an artificial dialysis membrane or using the peritoneal membrane in the case of peritoneal dialysis. The dialysate can also serve as a replacement fluid where ultrafiltration is performed to remove fluid from the blood. Suitable components that may be used in dialysate or replacement fluid include bicarbonate, acetate, lactate, citrate, amino acid and protein buffers. The concentration and composition of the buffers and components thereof may be adjusted based on monitored pH of the patient's blood. Similarly, the concentration of electrolytes such as sodium, potassium, calcium, and chloride in replacement fluid or dialysate may be set or altered based the monitored levels of electrolytes.

The methods, systems and devices described herein may be used, in some embodiments, to set the initial electrolyte concentration and pH (buffer components and concentration) based on monitoring that occurs before a blood fluid removal or dialysis session starts, herein referred to as a blood fluid removal session. In some embodiments, the monitoring is chronic; e.g., monitoring is performed intermittently, periodically or continuously over the course of days, weeks, months or years. In an attempt to minimize interference with the patient's lifestyle, the monitoring system, or components thereof, can be implantable or wearable similar to the devices described above.

In some embodiments, one or more sensors are employed to detect one or more ions to gauge pH or electrolytes in the blood. In some embodiments, a sensor can have more than one transducer, even if leadless, that con monitor more than one ionic species. By measuring more than one ionic species, a more detailed understanding of the levels of various electrolytes or blood components may be had. For example, in some patients in some situations, one electrolyte may be at elevated levels while another may be at reduced levels. In some embodiments, more than one sensor for the same ion is employed for purposes of result confirmation and redundancy, which can improve reliability and accuracy. In some embodiments, sensors for the same ion may be configured to accurately detect different ranges of concentrations of the ion. In embodiments, more than one transducer is present in a single unit. This allows for convenient data collection and circuitry, as all the data may be collected in one place at the same time. Further, the multiple transducers may share the same fluid collection mechanism (e.g., a microdialyzer in the case of an implant), and if needed or desired, may share the same data processing and memory storage components.

Sensor that measure pH or electrolytes by direct contact with bodily fluids can be employed, such as ion-selective electrodes. Similarly, pacemakers or external or implantable ECG monitors (such as the Reveal® system) can be used to monitor electrolytes and can optionally be used in conjunction with sensor that take measurements through direct contact with bodily fluids.

Implantable sensors or sensors in which the transducer is chronically inserted in a tissue or blood of a patient may be calibrated prior to implant by placement of the transducer in blood (or other conditions mimicking the implant environment) with known pH or electrolyte concentrations. The sensors can be recalibrated while implanted in the patients. For example, blood pH and electrolyte concentration can be measured external to the patient, e.g., via blood draws, and results of the external monitoring can be communicated to the implanted sensor by receiving input, e.g., from healthcare providers. Thus, the sensor, if sensor has necessary electronics, can recalibrate based on the input regarding the external measurements. Alternatively, or in addition, the sensor may have an internal reference built in, such as with the Medtronic, Inc. Bravo® pH sensor. Alternatively, in cases where the sensor outputs raw data to an external device, the external device may be calibrated to interpret the raw data from the sensor with regard to input regarding the external measurements.

Figure 14:
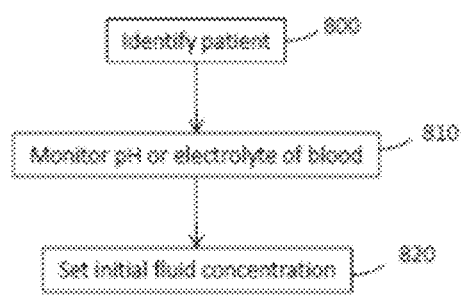
FIGS. 14-18 show flow diagrams illustrating methods in accordance with certain embodiments described herein.

Referring now to FIG. 14, the depicted method includes identifying, selecting or diagnosing a patient for which a blood fluid removal or dialysis session is indicated 800 and monitoring pH or electrolyte levels of the blood of the patient 810. The monitoring 810 can be chronic and may employ one or more implantable sensors or an ECG monitoring device. Based on the monitored pH or electrolyte concentration, the fluid (e.g., dialysate or replacement fluid) composition (e.g., electrolyte concentration, buffer composition and concentration) for use initial use in a blood fluid removal session may be set 820. As described above, the ability to chronically monitor pH or electrolyte concentrations of the patient's blood provides the ability to tailor the fluid composition prior to each blood fluid removal session, as opposed to current standard practice in which the fluid composition is adjusted on a monthly basis (or thereabout). As multiple blood fluid removal sessions (e.g., two to three a week) may occur with a month, setting the fluid composition on a monthly basis may result in the patient undergoing several blood fluid removal sessions with a fluid composition that may no longer be well suited for the patient.

Figure 15:
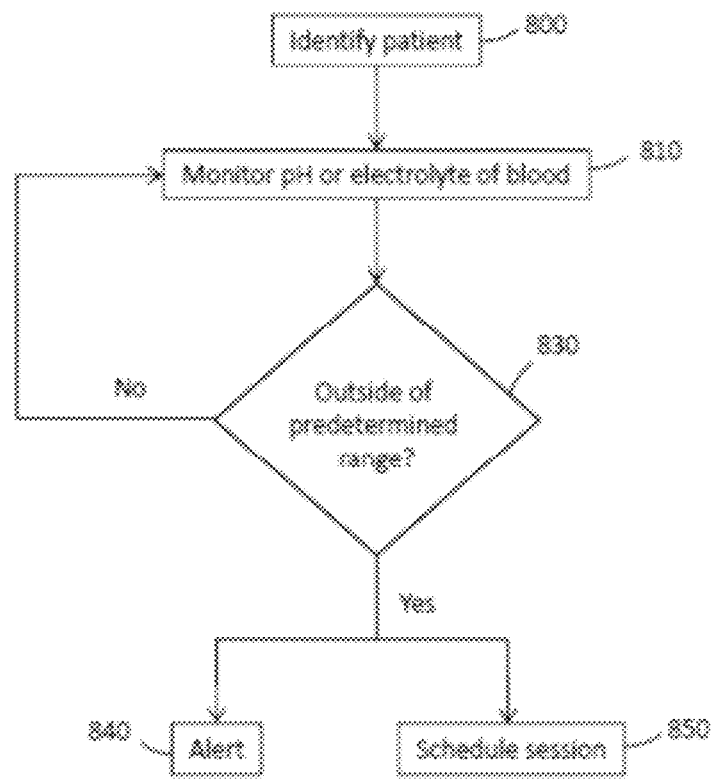

Referring now to FIG. 15, method includes identifying, selecting or diagnosing a patient for which a blood fluid removal or dialysis session is indicated 800 and monitoring pH or electrolyte levels of the blood of the patient 810. As with the method in FIG. 14, the monitoring 810 may be chronic and may employ one or more implantable sensors or an ECG monitoring device. The method depicted in FIG. 16 includes determining whether the pH or electrolyte concentration is out of range 830 based on data acquired during the monitoring 810. For example, a determination 830 can be made as to whether pH or electrolyte levels crossed a threshold (e.g., a ceiling or floor). Suitable thresholds or ranges may be stored in, for example, a look-up table in memory of a sensor device, a blood fluid removal device, or other suitable device for purposes of determining whether the pH or electrolyte concentration is out of range 830 based on data acquired during the monitoring. If the pH or electrolytes are determined to be within range, monitoring 810 may continue. If the pH or electrolytes are determined to be out of range (e.g., cross a threshold), an alert 840 can be issued or a blood fluid removal session (850) may be scheduled.

The scheduled blood fluid removal session may take into account the monitored 810 pH or electrolytes, e.g. as described with regard to FIG. 14. The scheduling may occur automatically, e.g. the sensor or a device in communication with the sensor may transmit data and cause scheduling of session over internet, telephone, or other suitable network, or using any of the communication systems described above.

Any suitable alert 840 may be issued. The alert may be a tactile cue, such as vibration or audible alarm, generated by a sensor or a device in communication with sensor. The alert may provide the patient with notice that medical attention should be sought. The alert may also provide information to a healthcare provider regarding the nature of the health issue (e.g., pH or electrolytes out of range) and treatment (e.g., blood fluid removal session) for which the alert 840 was issued. The sensor or a device in communication with the sensor may alert the healthcare provider by transmitting the alert or related information over the internet, a telephone network, or other suitable network to a device in communication with the healthcare provider.

Figure 16:
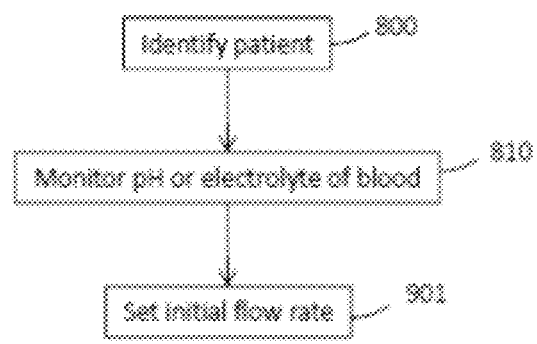

Referring now to FIG. 16, the depicted method includes identifying, selecting or diagnosing a patient for which a blood fluid removal or dialysis session is indicated 800 and monitoring pH or electrolyte levels of the blood of the patient 810. The monitoring 810 can be chronic and may employ one or more implantable sensors or an internal or external ECG measuring device. Based on the monitored pH or electrolyte concentration, the rate of flow of dialysate or blood, based in part on the concentration of electrolytes and pH composition of the dialysate, is set 901. As described above, the rate of flow of dialysate or blood affects the rate of transfer of electrolytes, etc. across the dialysis membrane. Accordingly, depending on the composition of the dialysate used, the rate of flow of the dialysate or blood may be adjusted or set so that desirable blood pH and electrolyte levels may be achieved during the course of a treatment session.

Figure 17:
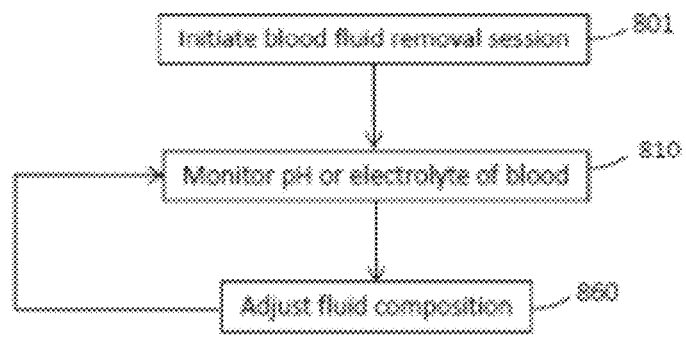

In additionally embodiments, the one or more sensors used to monitor pH and/or electrolytes described above can be used to modify the composition of a dialysate or a replacement fluid during dialysis. Referring now to FIG. 17, the depicted method includes initiating a blood fluid removal or dialysis session 801 and monitoring pH or electrolyte concentration of blood 810. As discussed above, the monitoring may occur via one or more implanted sensors or an internal or external ECG measuring device. Based on the monitored pH or electrolytes, the pH or electrolyte composition or concentration of fluid (e.g., dialysate or replacement fluid) used in the blood fluid removal session may be adjusted 860. For example, based one or more of the current value of a monitored ionic species or the rate of change in the monitored ionic species, the fluid composition may be adjusted, e.g. as discussed above.

Figure 18:
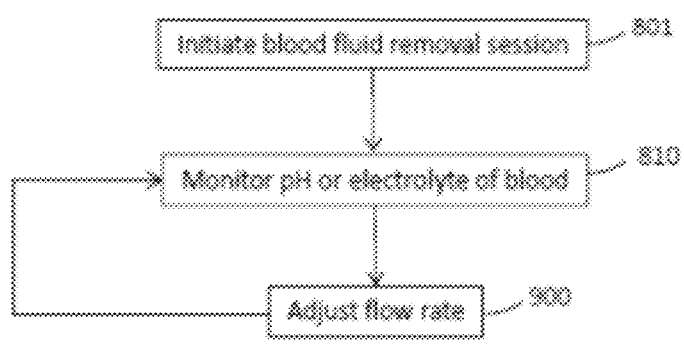

Referring now to FIG. 18, the depicted method show a method where blood electrolyte concentration or pH is adjusted by altering the flow rate of dialysate or blood. The method includes initiating a blood fluid removal session 801, such as a hemodialysis session, and monitoring an indicator of pH or electrolyte 810, which can be in the patient, upstream of the device, downstream of the device, within the device, or the like. Based on the monitored data (810), adjustments to the flow of dialysate or blood may be made 900 to adjust the electrolyte concentration or pH in the blood that gets returned to the patient.

Automated Updating of Dialysis Parameters

In certain embodiments, the monitoring of patient electrolytes or pH, as described above, between dialysis treatment sessions can be used to assist in determining the appropriate scheduling or length of a future dialysis session and/or an appropriate dialysate or replacement solution to be used in such a session. By comparing the patient's past responses to dialysis parameters or changes in dialysis parameters, a system can be able to avoid future use of parameters that may harm the patient and can learn which parameters are likely to be most effective in treating the patient in a blood fluid removal or dialysis session. Dialysis parameters include scheduling, length of dialysis sessions as well as dialysate or replacement fluid composition, which are referred to as system parameters herein.

Figure 19:
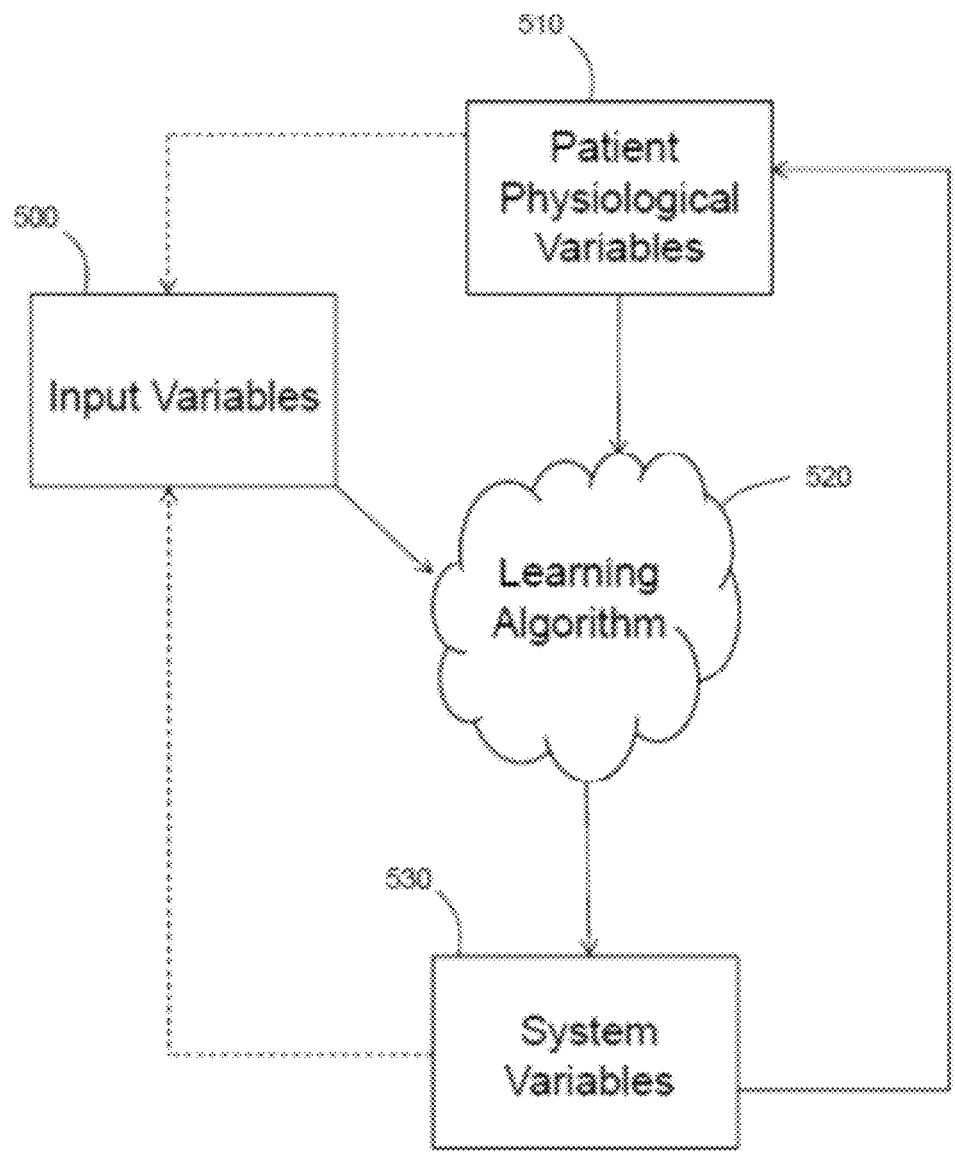
FIGS. 19-25 show flow diagrams illustrating methods in accordance with certain embodiments described herein.

Referring to FIG. 19, a high level schematic overview of embodiments of the present disclosure is shown. As shown in FIG. 19, a learning algorithm 520 is employed to determine what system parameters work well to produce desired patient physiological results based on input. Any suitable input variable 500 can be considered by the algorithm 520 in the learning process. For example, variables such as how long it has been since the patient's last blood removal session may be input. Such input could be important as patients undergoing, for example, hemodialysis on a Monday, Wednesday, Friday schedule are more likely to suffer an adverse cardiac event just before, during or after the Monday blood fluid removal session. Accordingly, the algorithm 520 may consider whether a different set of system parameters should be employed when the patient has not undergone a session in 72 hours relative to when the patient has not undergone a session in 48 hours. Input variables 500 may also include whether the patient has limited time to undergo a blood fluid removal session. The algorithm 520 can determine whether a faster fluid removal rate should be used or whether a partial session at a reduced fluid removal rate would likely be more effective based on the patient's history of response to fast fluid removal rates. Alternatively, the patient may have additional time to undergo a blood fluid removal session, and the algorithm 520 can take such input 500 into account to determine whether there may be an advantage to slower fluid removal rates or slower adjustment of a concentration of an electrolyte based on the patient's history. Of course, it will be understood that any other suitable input variables 500 may be entered regarding target outcomes (e.g., quick session, long session, etc.), patient history (e.g., time since last session), or the like. In embodiments, input that takes into account future patient behavior or needs may be entered into the system. For example, if a patient knows that they will miss a session or the time until their next session will be delayed from normal, time until next session may be entered, which may affect the system parameters (e.g., may remove additional fluid, etc.). By way of another example, if the patient knows that they will eat or drink an amount more than optimal before the session, expected consumption levels may be input in the system.

As shown in FIG. 19, the algorithm 520, based on input variables 500, and patient physiological variables 510 may determine appropriate system variables 530 to employ based on the patient's history with blood fluid sessions under the algorithm. During a blood fluid session, system variables 530 may be changed and the patient physiological response may be monitored in response to the changed system variables. If one or more of the patient's physiological variables 510 improve, the algorithm 530 can associate the changed system variables 530 with the improved patient outcome so that the changed system variables 530 may be used later in the session or in a future session when the patient has a similar set of physiological variables 510. If one or more of the patient's physiological variables 510 worsen, the algorithm 530 can associate the changed system variables 530 with a worsened patient outcome so that the changed system variables 530 may be avoided later in the session or in a future session when the patient has a similar set of physiological variables 510.

In embodiments, the input variables 500 include patient physiological variables that have occurred in a time period preceding a blood fluid removal session. For example, the time period may be a period of time (e.g., all or one or more portions of time) since the patient's last session. In embodiments, the input variables include input indicating (i) how long favorable patient variables 510 (e.g., above or below a predetermined threshold) were observed after the last session; (ii) the rate of change of patient variables 510 following the last session, (iii) etc., all of which may be compared against system parameters 530 used in the previous session. If the patient physiological 510 or other variables (e.g. patient input regarding how the patient has felt), were favorable since the last session, the system may employ similar variables in future sessions. It may also or alternatively be desirable to monitor patient physiological or other variables in a time period leading up to a session and input such variables into the algorithm 520 or system before the session. The system or algorithm 520 can then determine whether the patient has presented with similar symptoms or parameters in previous sessions and employ system variables 530 to which the patient responded favorably, either in the session, after the session, or both in the session and after the session. Accordingly, the system or algorithm 520 may monitor patient well-being, which may be derived from patient physiological variable 510 or input variables 500, within a session and between sessions to determine which system variables should be employed and changed based on the patient response to previous sessions. As indicated by the dashed lines and arrows in FIG. 19, patient physiological variables 510 obtained between sessions and system variables 530 used in a prior session may be input variables 500 in a current or upcoming session.

In embodiments, the physiological variables 510 are monitored by sensors that feed data regarding the variables directly into the algorithm 520 or electronics running the algorithm. The sensors may monitor fluid volume in the patient's blood; fluid volume in the patient's tissue; concentrations of electrolytes in the patient's blood; pH of the patient's blood; one or more cardiovascular parameter of the patient, such as blood pressure, heart rhythm, heart rate; or combinations or indicators thereof. The sensors may monitor the patient physiological parameters before, during or after a blood fluid removal session.

A sensor configured to monitor hemoglobin levels may also be used as an indicator of blood fluid volume, as hemoglobin concentration is typically proportional to red blood cell concentration. Thus, lower the hemoglobin concentrations may be indicative of higher blood fluid volume. Any suitable sensor may be used to measure hemoglobin concentration, such as sensors used in pulse oximeters which measure adsorption of red and infrared light to determine concentration of oxygenated hemoglobin and deoxyhemoglobin, respectfully. The sensors (which may include the associated light source(s)) may be placed in any suitable location, such as around tubing that carries blood from the patient to the blood fluid removal device or from the blood fluid removal device to the patient, within the blood fluid removal device, or the like. In addition or alternatively, a sensor may be implanted in a patient and disposed about a blood vessel to measure hemoglobin levels, and thus hematocrit and blood fluid levels. By way of further example, total blood protein or albumin concentrations and blood pressure, alone or in combination, can be used to evaluate blood volume. High blood pressure combined with low hematocrit or low blood protein may indicate a higher possibility of blood fluid overloading. Alternatively or additionally, blood viscosity may be used as an indicator of blood fluid volume and may be measured by pressure or flow. Impedance, capacitance, or dialectic constant sensors may be employed to monitor fluid volume. For example, impedance may be monitored between two electrodes. The electrodes may be operably coupled to control and processing electronics via leads. The electronics are configured to generate a voltage differential between the electrodes, current may be measured, and impedance calculated. The measurement may be done in either DC or AC mode. Impedance or phase angle may be correlated to tissue fluid volume. Tissue impedance sensing for purposes of monitoring tissue fluid volume has been well documented. One example of a well studied system that may be used or modified for use herein is Medtronic, Inc.'s OptiVol® fluid status monitoring system. Such a system, or other similar systems, have well-documented procedures for determining acceptable ranges of tissue impedance and thus fluid volume. See, e.g., (i) Siegenthalar, et al. Journal of Clinical Monitoring and Computing (2010): 24:449-451, and (ii) Wang, Am. J. Cardiology, 99(Suppl):3G-1-G, May 21, 2007. Alternatively or in addition, tissue impedance may be monitored for a suitable period of time to establish as suitable baseline, and patient markers or clinician input may be used to instruct whether the patient is fluid overloaded or underloaded. The data acquired by impedance sensor and input data regarding fluid status of the patient at the time the sensor data is acquired may be used to establish suitable ranges for impedance values.

Suitable transducers may include an ion selective electrode configured to detect $H^+$ ions, $K^+$ ions, $Na^+$ ions, $Ca^{2+}$ ions, $Cl^-$ ions, phosphate ions, magnesium ions, acetate ions, amino acids ions, or the like. Such electrodes, and components of sensors employing such electrodes, are known in the art and may be employed, or modified to be employed, for use in the monitoring described herein. One or more sensors may be employed to detect one or more ions to gauge pH or electrolytes in the blood. In some embodiments, a sensor may have more than one transducer, even if leadless, that may monitor more than one ionic species. By measuring more than one ionic species, a more detailed understanding of the levels of various electrolytes or blood components may be had. For example, in some patients in some situations, one electrolyte may be at elevated levels while another may be at reduced levels. In some embodiments, more than one sensor for the same ion is employed for purposes of result confirmation and redundancy, which can improve reliability and accuracy. In some embodiments, sensors for the same ion may be configured to accurately detect different ranges of concentrations of the ion. In embodiments, more than one transducer is present in a single unit. This allows for convenient data collection and circuitry, as all the data may be collected in one place at the same time. Further, the multiple transducers may share the same fluid collection mechanism (e.g., a microdialyzer in the case of an implant), and if needed or desired, may share the same data processing and memory storage components. A sensor (or transducer) for detecting pH, electrolyte concentration, or the like may be placed at any suitable location for purposes of monitoring electrolytes or pH. For example, the sensor may be implanted in the patient, located external to the patient an upstream of a blood fluid removal device, located external to the patient and downstream of the blood fluid removal device, or the like.

One suitable implantable sensor device that is configured to monitor a patient's ECG signals is a Medtronic, Inc.'s Reveal® series insertable cardiac monitor described above. In embodiments, the sensor device may be a suitably equipped pacemaker or defibrillator already implanted in the patient. Monitored cardiac signals from such a device may be transmitted to a blood fluid removal device or intermediate device for use in the blood fluid removal session or for setting the prescription for the blood fluid removal session. Blood pressure monitors, which may be external or implantable (such as Medtronic Inc.'s active leadless pressure sensor (ALPS), which generally takes the form of a stent to anchor the device within a vessel), may be employed. Such a device may be placed in any suitable blood vessel location, such as in a femoral artery or pulmonary artery. A wearable sensor system, such as a Holter sensor system, may be used to monitor ECG activity of the patient. Regardless of whether the sensor or sensor system employed, or components thereof, is implantable, wearable, part of a larger stand-alone device, or part of a blood fluid monitoring device, the sensor may monitor any suitable cardiovascular parameter of a patient. In various embodiments, the sensors or monitoring systems are configured to monitor one or more of heart rate, heart rhythm or a variable thereof, or blood pressure. Examples of variables of heart rhythm that may be measured are heart rate variability (HRV), heart rate turbulence (HRT), T-wave alternans (TWA), P-wave dispersion, T-wave dispersion, Q-T interval, ventricular premature depolarization (VPD), or the like.

As indicated above, sensors for monitoring patient physiological parameters may be, or may have components that are, implantable or wearable. In embodiments, multiple sensors may be connected via telemetry, body bus, or the like. The connected sensors may be of the same or different type (e.g., pH or impedance). Such connected sensors may be placed (e.g., internal or external) for purposes of monitoring at various locations of the patient's body.

Monitoring may alternatively or additionally include receiving patient or physician feedback regarding the patient's state. For example, the patient may indicate a point in time when cramping begins, which often happens when too much fluid is removed. The blood fluid monitoring device may include an input, such as a keyboard or touch screen display for entering such data. Alternatively, a separate device such as a patient programmer, laptop computer, tablet computer, personal data assistance, smart phone or the like may be used to input the data; or the like.

Figure 20:
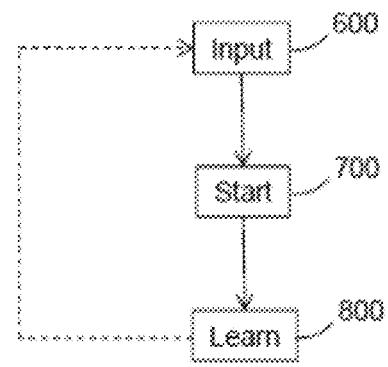

Referring now to FIG. 20, a high level flow diagram of a method is described. The method includes providing input 600, such as input variables discussed above with regard to FIG. 20, to a blood fluid removal system. The method also includes initiating or starting 700 a blood fluid removal or dialysis session, and learning 800 from the session. The learning 800 may be as discussed above with regard to FIG. 19 with system parameters being varied and patient physiological parameters being monitored to determine which system parameter adjustments result in desirable patient physiologic outcomes. The learning may also occur over multiple sessions by monitoring patient variables within the sessions or by monitoring patient variables between sessions to determine how well the patient responded prior sessions to predict how well a patient will respond to future sessions (or to set initial parameters for future sessions based on prior experiences).

Figure 21A:
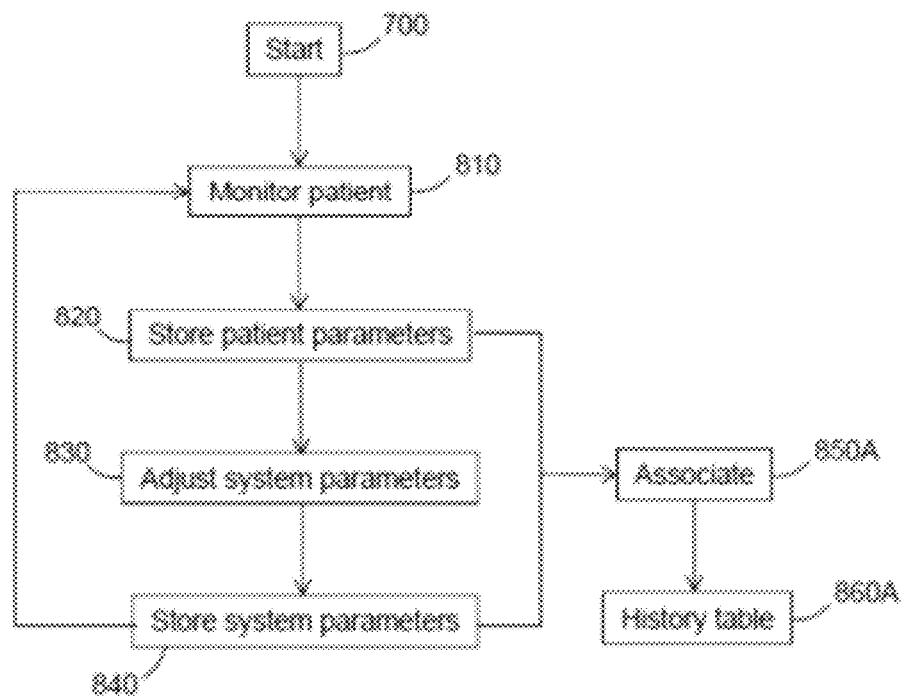

For example and with reference to FIG. 21A, additional detail regarding an embodiment of a learning process that may occur during a blood fluid removal or dialysis session is shown. The blood fluid removal or dialysis session is started 700 and the patient is monitored 810. Monitored patient parameters, such as patient physiological variables as discussed above, are stored 820; e.g., in memory of the blood fluid removal system. The system parameters, such as system variables described above, which may include rate of fluid removal from the blood or electrolyte concentration of a dialysate or replacement fluid, are adjusted 830 and the system parameters are stored 840; e.g., in memory of the blood fluid removal, monitoring system, or dialysis system, and patient monitoring 810 continues. The set of stored patient parameters 820 are associated 850A with a set of stored system parameters 840 so that the system may recall particular system parameters that were employed at the time the patient had a given set of parameters. The data regarding the stored patient parameters 820 and the stored system parameters 840 may be tagged with, for example, a time event to associate the two sets of data. Of course any other suitable method or mechanism for associating the data sets may be employed. In some embodiments, the associated data, or a portion thereof, is placed in a lookup table tracking the patient's history of physiological response to changing system parameters 860A.

Figure 21B:
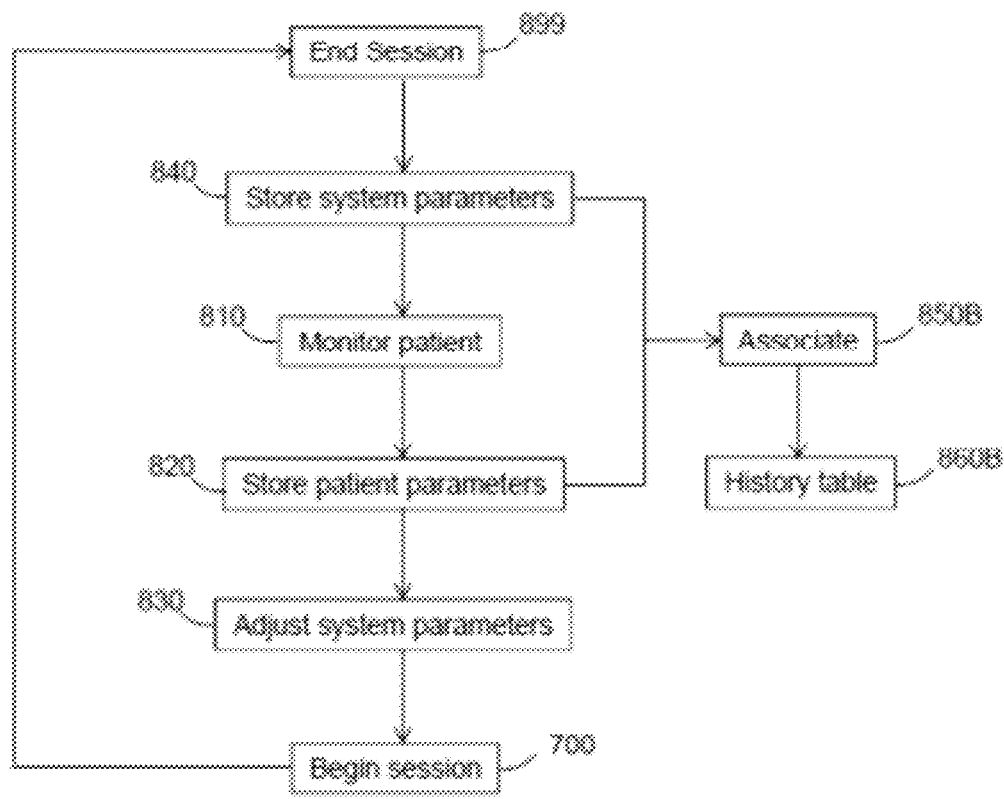

Referring now to FIG. 21B, an overview of a learning process that may occur with monitoring between blood fluid removal or dialysis sessions is shown. Before, during or after a blood fluid removal or dialysis session is ended 899, system parameters used in the session are stored 840. The system parameters, such as system variables described above, which may include rate of fluid removal from the blood or electrolyte concentration of a dialysate or replacement fluid, as well as any adjustments made during the session that has just ended may be stored in memory and associated with the patient. During one or more time periods between the end of the session 899) and the start of the next session 700, the patient is monitored 810. Monitored patient parameters, such as patient physiological variables as discussed above, are stored 820; e.g., in memory of the blood fluid removal system or in memory of a device capable of communicating with, or a part of, the blood fluid removal system. For example, if monitoring 810, or a portion thereof, occurs via an implanted device, the implantable monitoring device may be configured to wirelessly communicate with a blood fluid removal system or a device capable of communicating with the blood fluid removal system. If monitoring includes assays or other diagnostic procedures for which data is presented to a user, such as a health care provider, the data may be entered into a blood fluid removal system or device in communication with the blood fluid removal system. The set of stored system parameters 840 are associated 850B with a set of patient system parameters 820 so that the system may recall particular system parameters that were employed in prior sessions that resulted in a given set of patient parameters. The data regarding the stored patient parameters 820 and the stored system parameters 840 may be tagged with, for example, a time event to associate the two sets of data. Of course any other suitable method or mechanism for associating the data sets may be employed. In some embodiments, the associated data, or a portion thereof, is placed in a lookup table tracking the patient's history of physiological response to system parameters 860B. Depending on the patient's response (patient monitoring 810) to the prior sessions, the system parameters may be adjusted 83) prior to beginning the next session 700. The patient's responses between sessions may also affect changes made during a session.

Figure 21C:
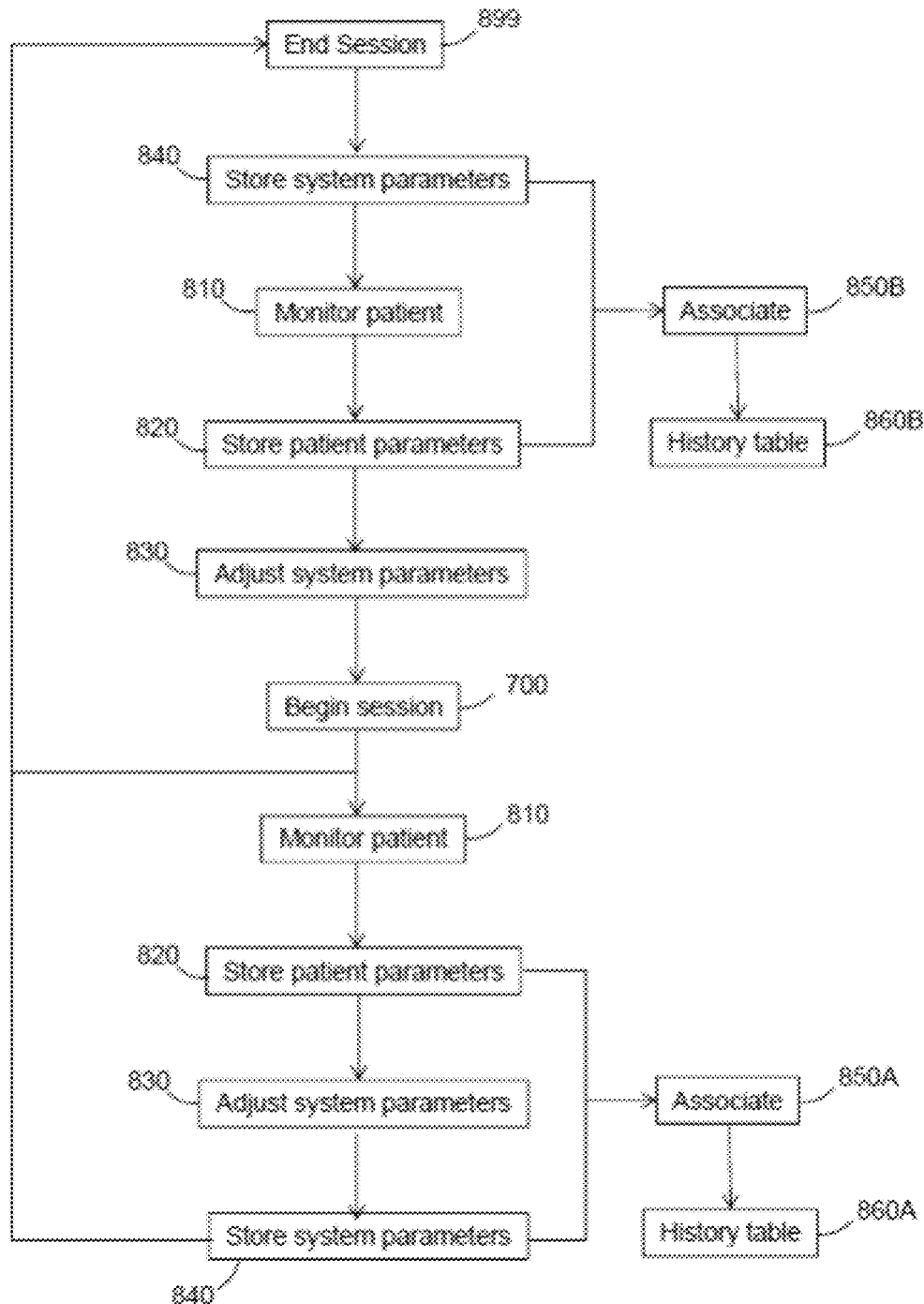

Referring now to FIG. 21C, an overview of a learning process that accounts for both inter-session and intra-session patient monitoring is shown. The process depicted in FIG. 21C is mainly a composite of the processes depicted and described above with regard to FIGS. 21A-B. As depicted in FIG. 21C, the process or algorithm may include associating 850A system parameters 840, and adjustments thereof 830, that result in good or bad outcomes with regard to patient parameters 820 and may recall those associations for later use, e.g. in the form of a lookup table 860A for purposes of making future adjustments to system parameters 830 based on patient response 810 within a session. Prior patient responses occurring between prior sessions (i.e., between end of session 899 and beginning of session 700) may also be taken into account (e.g., associated parameters (850B) that include patient parameters obtained between sessions) by, for example, referring to lookup table 860B. If, for example, changes in systems parameters (830) within a session are associated with good (effective) or bad (ineffective) patient responses (810) between sessions, similar changes may be made or avoided, as relevant, within a session. In addition, the patient response (810) to a prior session or the patient's condition (810) before a session may warrant adjustment of system parameters (830) prior to beginning a session (700). The patient response (810) within prior sessions may also be taken into account (e.g., by reference to history table 860A) in making system adjustments prior to beginning a session.

Figure 22A:
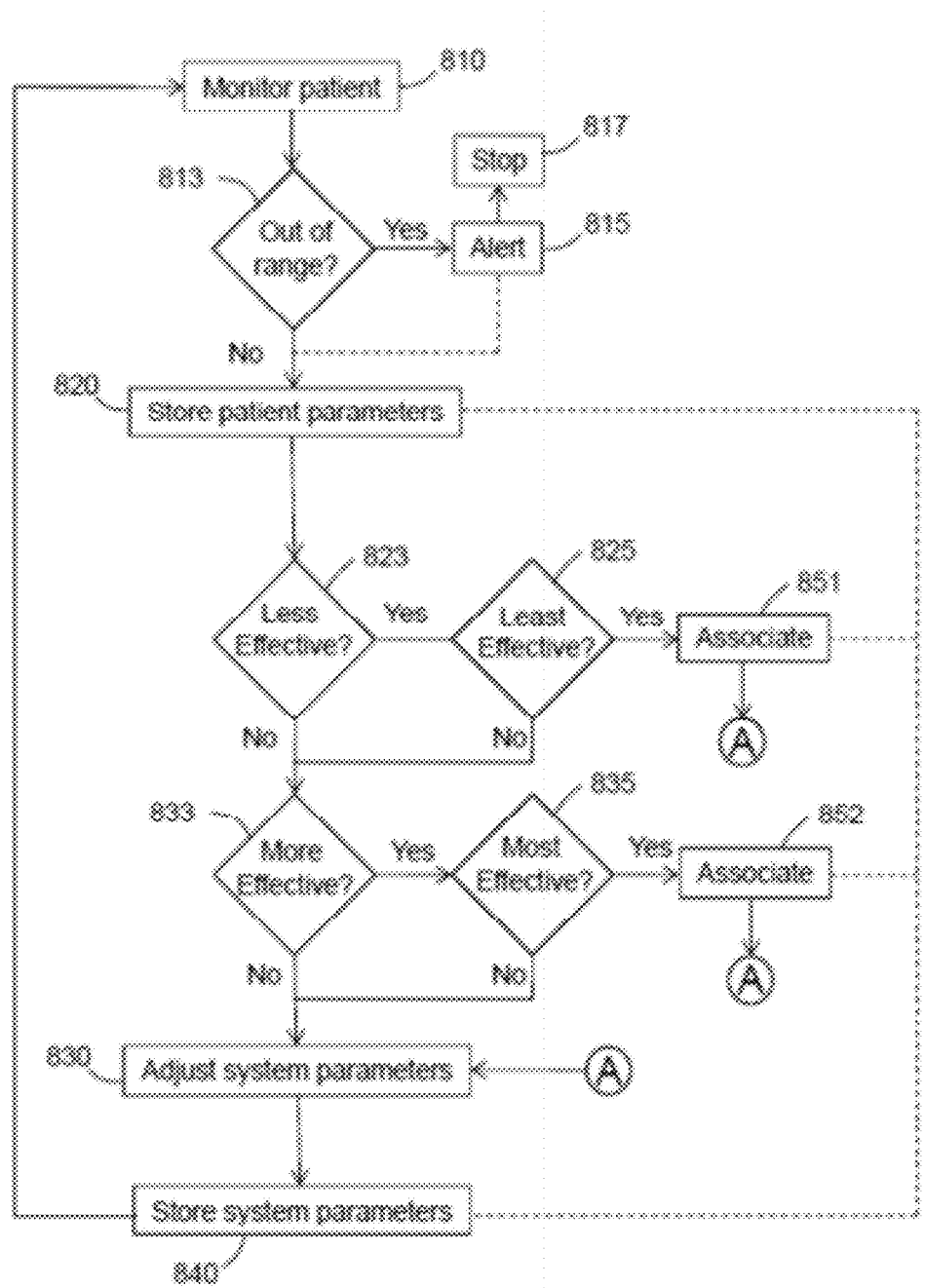
Figure 23A:
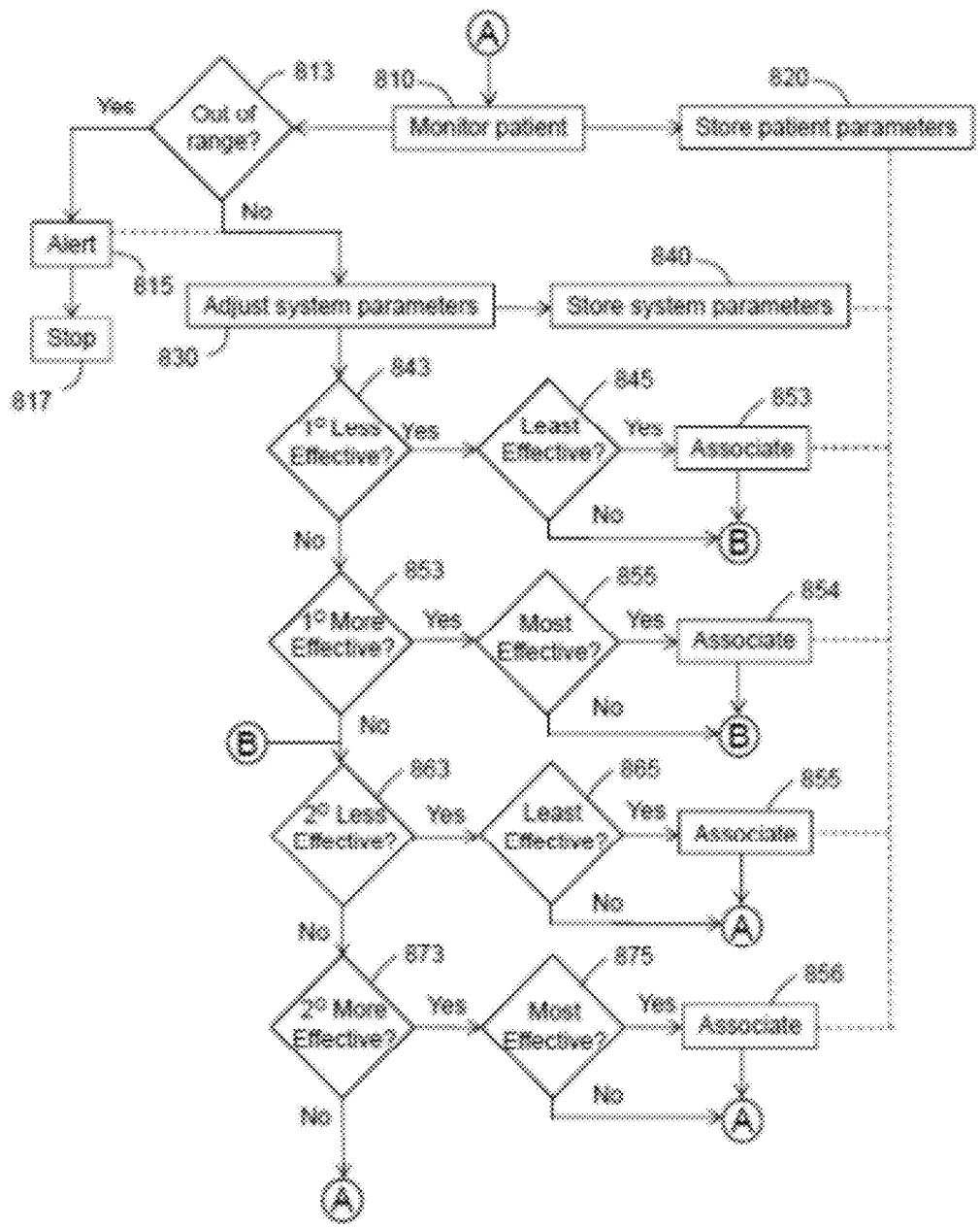

A more detailed embodiment of a within-session learning algorithm, or method is presented in FIG. 23A. In the embodiment depicted in FIG. 22A, a patient is monitored 810 during a blood fluid removal session. It may be desirable to determine whether data acquired from patient monitoring is out of range 813. As used herein, "out of range" means that a value of a monitored parameter exceeds (i.e., is above or below) a predetermined range of values. The predetermined range of values may be indicative of a patient safety concern. If the data is out of range, an alert may be issued 815 or the session may be stopped 817. In some cases, it may be desirable to continue with the session, even if the monitored data, or some aspect thereof is out of range. In the depicted embodiment, if the session is continued, (e.g., due to choice or to the monitored data not being out of range), data regarding the monitored patient parameters is stored 820 and is compared to stored patient data previously obtained (e.g., in a prior session or earlier in the session). A determination may be made as to whether the present patient parameter data is less effective 823 than stored patient parameter data resulting from system parameter adjustments 830 that occurred just prior to the current set of system parameters. If the data is determined to be less effective 823, the stored current patient parameters 820 may be associated 851 with stored current system parameters 840; e.g., as discussed above. In some cases, it may be desirable to determine whether the current patient parameter data, or a portion or aspect thereof, is the least effective that has been detected in the patient in a current or previous blood fluid removal session 825; e.g. by comparing the current patient data to a history of collected patient data. If the current patient data is the least effective observed 825 to date, the stored current patient parameters 820 can be associated 851 with stored current system parameters 840. In this way, only the "least effective" patient conditions are tracked, as opposed to all patient conditions, which can save on memory and processing power. In any case, once the patient and system parameter data is associated 851, the system parameters may be adjusted 830 and the process repeated.

If the present patient parameter data is determined to not be less effective than stored patient parameter data resulting from system parameter adjustments that occurred just prior to the current set of system parameters, a determination may be made as to whether the present patient parameter data is more effective 833 than stored patient parameter data resulting from system parameter adjustments 830 that occurred just prior to the current set of system parameters. If the data is determined to be more effective 833, the stored current patient parameters 820 may be associated 852 with stored current system parameters 840; e.g., as discussed above. In some cases, it may be desirable to determine whether the current patient parameter data, or a portion or aspect thereof, is the most effective that has been detected in the patient in a current or previous blood fluid removal session 835; e.g. by comparing the current patient data to a history of collected patient data (e.g., "history table" in FIG. 21). If the current patient data is the most effective observed 835 to date, the stored current patient parameters 820 can be associated 852 with stored current system parameters 840. In this way, only the "most effective" patient conditions are tracked, as opposed to all patient conditions, which can save on memory and processing power. In any case, once the patient and system parameter data is associated 852, the system parameters may be adjusted 830 and the process repeated.

Figure 22B:
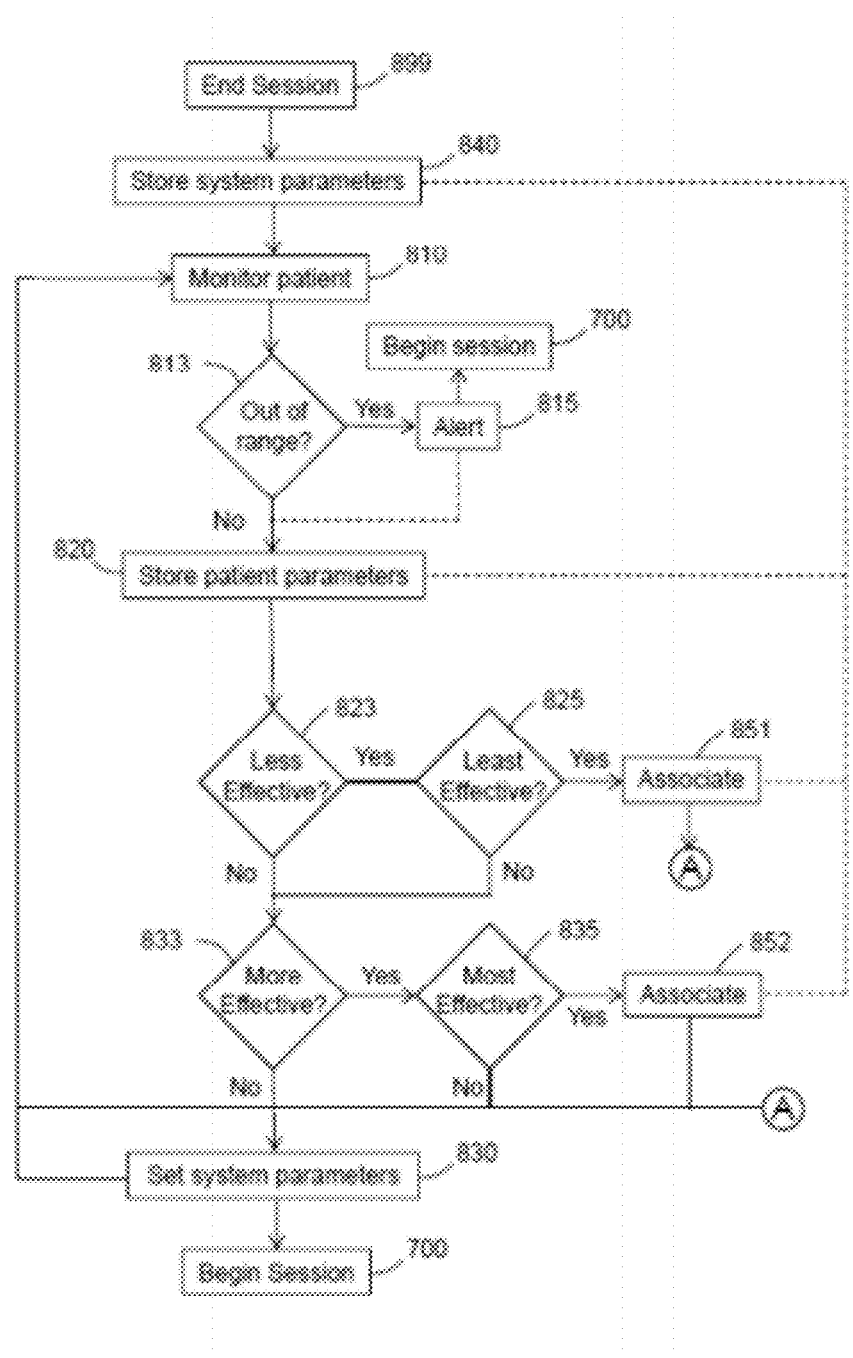

A more detailed embodiment of a between-session learning algorithm, or method is presented in FIG. 22B. In the embodiment depicted in FIG. 22B, patient is monitored 810 between a blood fluid removal or dialysis sessions. It may be desirable to determine whether data acquired from patient monitoring 810 is out of range 813. If the data is out of range, an alert may be issued 815 prompting the patient to seek medical attention or prompting a health care or an implanted system or device to take action. In some cases, a new session may be begun 700 if patient conditions warrant. If a new session is not initiated, the inter-session process may continue. In the depicted embodiment, if the process is continued, data regarding the monitored patient parameters is stored 820 and is compared to stored patient data previously obtained (e.g., between prior sessions). A determination may be made as to whether the present patient parameter data is less effective 823 than stored patient parameter data obtained between previous sessions. If the data is determined to be less effective 823, the stored current patient parameters 820 may be associated 851 with stored system parameters 840 from the previous session that had ended 899. In some cases, it may be desirable to determine whether the current patient parameter data, or a portion or aspect thereof, is the least effective that has been detected in the patient between blood fluid removal sessions 825; e.g. by comparing the current patient data to a history of collected patient data. If the current patient data is the least effective observed 825 to date, the stored current patient parameters 820 can be associated 851 with stored system parameters 840 from the previous session that had ended 899. In this way, only the "least effective" patient conditions are tracked, as opposed to all patient conditions, which can save on memory and processing power. In any case, once the patient and system parameter data is associated 851, a recommendation as to system parameters to be used in the next session may be made (e.g., the system parameters for the future session can be set 830 based on the patient response or prior patient responses) can be adjusted 830 and the process repeated until the next session begins 700.

If the present patient parameter data is determined to not be less effective than stored patient parameter data obtained from time periods between prior sessions, a determination may be made as to whether the present patient parameter data is more effective 833 than stored patient parameter data obtained from between prior sessions. If the data is determined to be more effective 833, the stored current patient parameters 820 may be associated 852 with stored current parameters 840 from the previous session that had ended 899. In some cases, it may be desirable to determine whether the current patient parameter data, or a portion or aspect thereof, is the most effective that has been detected in the patient in a time between sessions 835; e.g. by comparing the current patient data to a history of collected patient data (e.g., "history table" in FIG. 21). If the current patient data is the most effective observed 835 to date, the stored current patient parameters 820 may be associated 852 with stored system parameters 840 from the previous session that had ended 899. In this way, only the "most effective" patient conditions are tracked, as opposed to all patient conditions, which can save on memory and processing power. In any case, once the patient and system parameter data is associated 852, recommendation system parameters may set 830 based on the patient response or prior patient responses, and the process repeated until the next session begins 700.

It will be understood that the processes or algorithms depicted in, and discussed above with regard to, FIGS. 22A-B may be combined (e.g., in a manner similar to the combination of FIGS. 21A and 21B into FIG. 21C). In this way, setting of system parameters for an upcoming session can take into account how a patient responded to such parameters within prior sessions, or altering of system parameters within a session may take into account how a patient responded to such alterations between prior sessions.

Referring now to FIG. 23A, an embodiment of a method where more than one patient parameter variable is evaluated in a manner similar to that described with regard to FIG. 22A. In the embodiment depicted in FIG. 23A, two patient parameter variables are evaluated. However, it will be understood that any number of patient parameter variables may be evaluated by employing a method as depicted in FIG. 23A or using any other suitable method. In the embodiment depicted in FIG. 23A, the variables are labeled "primary" and "secondary", as it may be desirable to prioritize patient parameter variables. For example, in some cases it may be desirable to monitor blood pressure and attempt to achieve a stable blood pressure at or near a target range throughout the session because hypotension is one of the most common side effects of blood fluid removal sessions. That is, as long as other patient parameters are not out of a predetermined range, the system may attempt to keep blood pressure in check and make adjustments to that end. However, in some cases, reducing arrhythmias is the primary goal, as many patients for which a blood fluid removal process is indicated dire from complications due to arrhythmias. If arrhythmias are determined to be the primary patient parameter, the blood fluid removal system may attempt to keep arrhythmias in check and make adjustments to this effect without regard to other patient parameters, e.g., as long as the other patient parameters remain within acceptable limits.

The method depicted FIG. 23A includes monitoring patient parameters 810 (at least a primary and secondary patient parameter), storing patient parameter data 820, and determining whether a parameter, or aspect thereof, is out of a predetermined range 813. If the parameter is out of range, an alert may be issued 815, the blood fluid removal session may be stopped 817 or the session may continue. If the parameters are determined to not be out of range 813, the system parameters may be adjusted 843 and stored 840. A determination may then be made as to whether the primary patient parameter is less effective 843, e.g. by comparing current patient parameter data to stored patient parameter data resulting from system parameter adjustments that occurred just prior to the current set of system parameters. If the primary patient parameter is determined to be less effective 843, the current stored patient parameter data may be associated 853 with the current stored system parameters. Alternatively or in addition, a determination may be made as to whether the current patient parameter data regarding the primary parameter is the least effective that has been detected in the patient in a current or previous blood fluid removal session 845; e.g., as discussed above with regard to FIG. 22A. If it is the least effective, the current stored patient parameter data may be associated 853 with the current stored system parameters as described above with regard to FIG. 22A. Similarly determinations as to whether the primary patent parameter data is more effective 853 or the most effective to date 855 can be made and stored system and patient parameters may be associated 854. Similar determinations regarding whether the secondary patient parameter, or a value associated therewith, is less effective 863, the least effective 865, more effective 873, the most effective 875 and appropriate associations 855, 856 can be made. In this manner, the system may identify and learn how system parameters may affect individually monitored patient parameters, such as blood pressure, heart rate, fluid volume, and electrolyte concentration. Based on this information, the system may make choices as to which system parameters may be employed to produce results that are likely to be favorable to the patient.

Figure 23B:
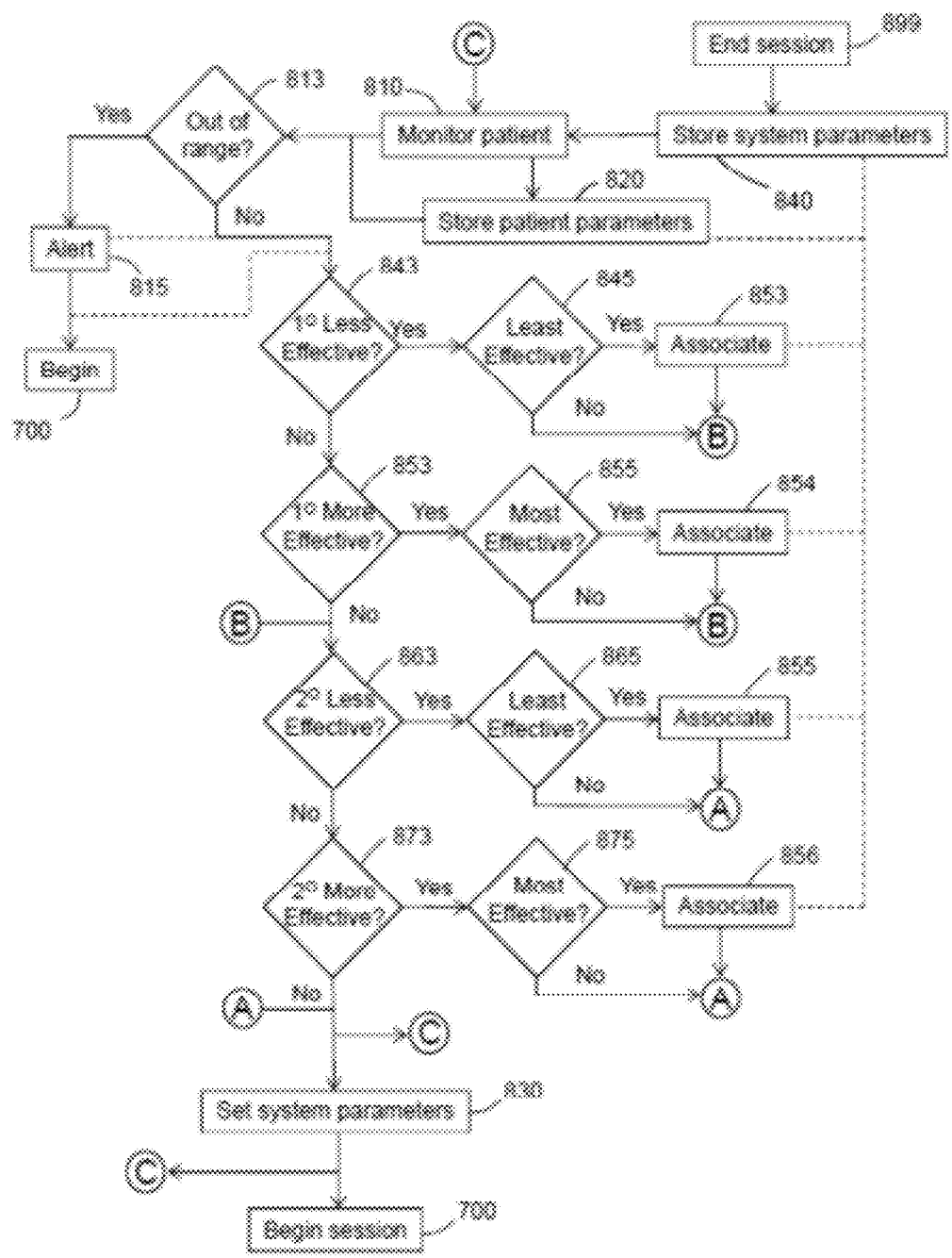

Referring now to FIG. 23B, an embodiment of a method where more than one patient parameter variable is evaluated between blood fluid removal or dialysis sessions in a manner similar to that described with regard to FIG. 22B. In the embodiment depicted in FIG. 23B, two patient parameter variables are evaluated. However, it will be understood that any number of patient parameter variables may be evaluated by employing a method as depicted in FIG. 23B or using any other suitable method. In the embodiment depicted in FIG. 23B, the variables are labeled "1°" and "2°". However, such labeling does not necessarily imply that one variable is more important than another. While one variable may, in some circumstances be considered more important, the labeling of "primary" and "secondary" may merely imply that the variables being monitored and tracked are different from one another.

The method depicted FIG. 23B includes ending a blood fluid removal session 899 and storing system parameters 840 from the ended session, which may be done during the session or after the session has ended (as depicted). The method also includes monitoring patient parameters 810 (at least a primary and secondary patient parameter), storing patient parameter data 820, and determining whether a parameter, or aspect thereof, is out of a predetermined range 813. If the parameter is out of range, an alert may be issued 815, prompting the patient to seek medical attention or prompting a healthcare provider or system or device to take action. In some cases, a blood fluid removal process can be initiated 700, e.g. if warranted or desired. If the parameters are determined to not be out of range 813 or if a blood fluid session is not initiated, a determination may be made as to whether the primary patient parameter is less effective 843, e.g. by comparing current patient parameter data to stored patient parameter data resulting from system parameters used in the previous session. If the primary patient parameter is determined to be less effective 843, the current stored patient parameter data may be associated 853 with the stored system parameters from the previous session. Alternatively or in addition, a determination may be made as to whether the current patient parameter data regarding the primary parameter is the least effective that has been detected in the patient between blood fluid removal sessions 845; e.g., as discussed above with regard to FIG. 22B. If it is the least effective, the current stored patient parameter data can be associated 853 with the stored system parameters as described above with regard to FIG. 22B. Similarly determinations as to whether the primary patent parameter data is more effective 853 or the most effective to date 855 can be made and stored system and patient parameters may be associated 854. Similar determinations regarding whether the secondary patient parameter, or a value associated therewith, is less effective 863, the least effective 865, more effective 873, the most effective 875 and appropriate associations 855, 856 can be made. In this manner, the system may identify and learn how system parameters employed in previous sessions may affect individually monitored patient parameters, such as blood pressure, heart rate, fluid volume, and electrolyte concentration. Based on this information, the system may make choices as to which system parameters may be employed in future sessions to produce results that are likely to be favorable to the patient.

As depicted in FIG. 23B, recommended system parameters may be set 830 based on how the patient responded to the prior session or the patient's condition prior to the upcoming session. The recommended system parameters may be adjusted or set 830 more than once during the process of monitoring the patient between sessions or at the end of the inter-session monitoring before initiating the next blood fluid removal session 700.

It will be understood that the processes or algorithms depicted in, and discussed above with regard to, FIGS. 23A-B may be combined (e.g., in a manner similar to the combination of FIGS. 21A and 21B into FIG. 21C). In this way, setting of system parameters for an upcoming session may take into account how a patient responded to such parameters within prior sessions, or altering of system parameters within a session may take into account how a patient responded to such alterations between prior sessions.

Figure 24A:
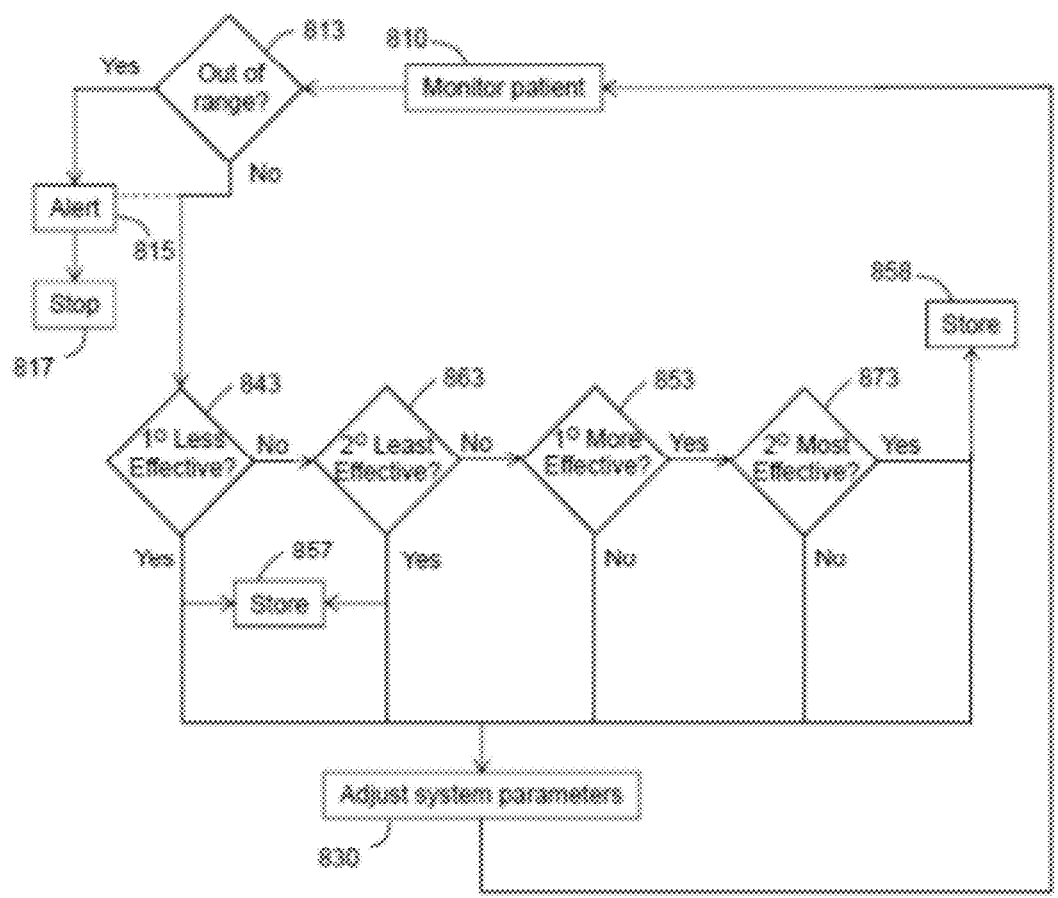

Referring now to FIG. 24A, a flow diagram depicting a process where the combined response of two or more patient parameters to changes in system parameters 830 is tracked within a session. For the purposes of convenience some of the steps depicted and described above with regard to FIGS. 22A and 23A are omitted from FIG. 24A. However, it will be understood that the same or similar steps may be employed with regard to the method depicted in FIG. 24A. In the depicted embodiment, patient parameters and system parameters are stored 857, 858 only when both the primary and secondary patient parameters are determined to become less effective 843, 863 or more effective 853,873. In this manner, the system may identify or learn which system parameters result in desirable (or undesirable) changes in multiple patient parameters.

Figure 24B:
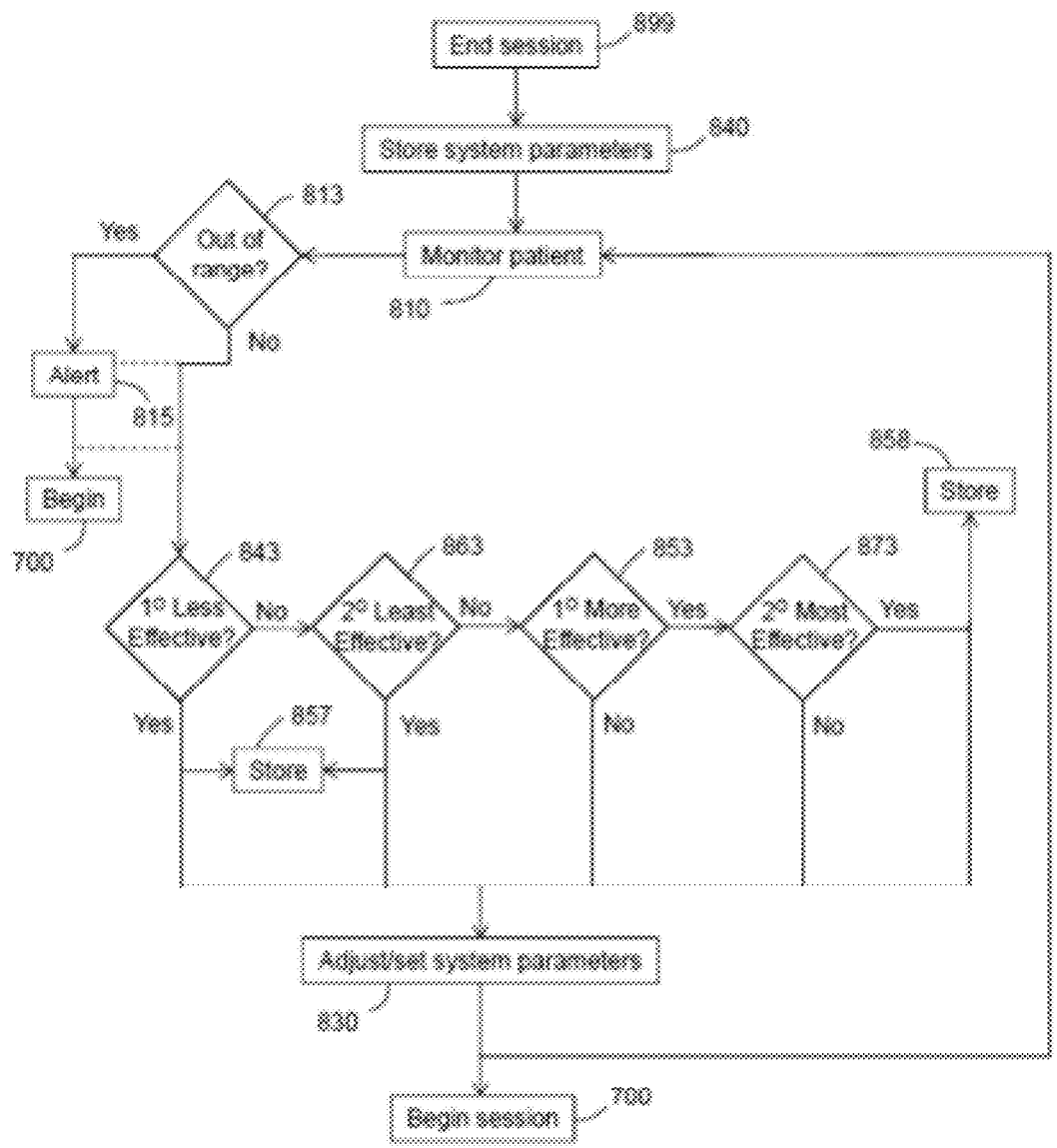

Referring now to FIG. 24B, a flow diagram depicting a process where the combined response of two or more patient parameters to changes in system parameters 830 is tracked between sessions. For the purposes of convenience some of the steps depicted and described above with regard to FIGS. 22B and 23B are omitted from FIG. 25B. However, it will be understood that the same or similar steps may be employed with regard to the method depicted in FIG. 24B. In the depicted embodiment, patient parameters are stored 857, 858 only when both the primary and secondary patient parameters are determined to become less effective 843, 863 or more effective 853, 873 and can be associated with stored system parameters 840 for the previously ended session 899. In this manner, the system may identify or learn which system parameters result in desirable (or undesirable) changes in multiple patient parameters.

Through the association of patient parameter data and system parameter data as shown in FIGS. 21-24 and discussed above, a history of patient responses, within sessions or between sessions, to changing system parameters may be obtained. This history, which may be in the form of one or more lookup table, may be consulted prior to or during a blood fluid removal session to determine which system parameters, given the patient's physiological parameters at a given point in time, are more likely to cause the patient to respond favorably and which system parameters are more likely to cause the patient to respond negatively. Accordingly, the system may respond by adjusting or setting parameters to those that are more likely to cause the patient to respond favorably.

Figure 25:
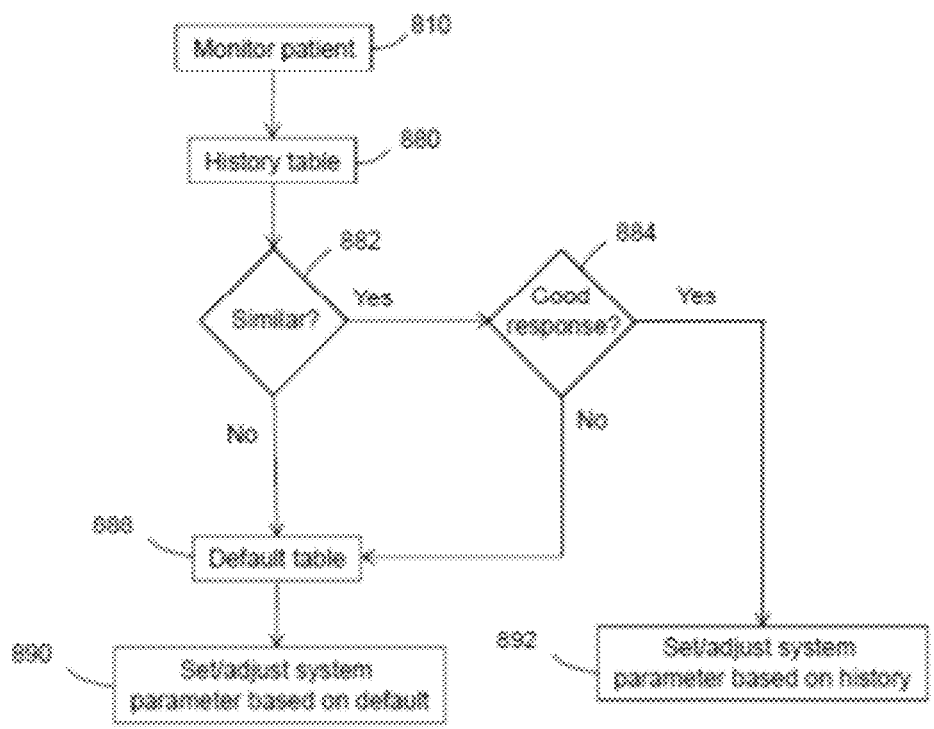

For example and with reference to FIG. 25, a flow diagram is shown that depicts and embodiment of how stored and associated data (e.g., as discussed above with regard to FIGS. 21-24) can be used to determine which system parameters to use at a given time in or before a blood fluid removal session. The method includes monitoring patient parameters 810, within a blood fluid removal session or between sessions, and consulting history lookup table 880, which may be generated by associating system parameters and patient parameters as described above with regard to FIGS. 21-24. Monitoring the patient 810 may include monitoring physiological variables or receiving input from the patient, a healthcare provider, or the like. A value associated with the current patient parameter data (obtained from monitoring 810) is compared to data regarding a corresponding value in the lookup table, and a determination is made as to whether the current patient parameter is similar to prior patient parameter data stored in the history table 882. By way of example, a value of a current patient parameter data set may be determined to be similar to a corresponding value in the lookup table if the values are within 10%. The system may consult the lookup table to identify the closest corresponding value, if more than one corresponding value is within the predetermined cutoff for being considered similar (e.g., within 10%). As used herein, a "corresponding" value is a value of the same parameter obtained at different times. The value may be a magnitude, a rate of change, an average, or the like. The parameter may be blood pressure, heart rate, fluid volume, concentration of electrolyte, or the like.

If more than one parameter or value of a parameter is compared to data in the lookup table, the system may determine whether each value for each parameter is within the predetermined cutoff for being considered similar and identify a prior patient parameter data set as being most similar by prioritizing or weighting parameters or by summing the percent differences between all of the current values and the corresponding values in the lookup table. Regardless of how the system determines whether a current patient parameter data set is similar, or most similar, to a prior patient data set stored in the history table, a determination may be made as to whether the patient's response to the system parameters associated with the stored patient parameter data table was a favorable response 884; e.g., was "more effective" or "most effective" as discussed above with regard to FIGS. 22-24. If the prior patient response was determined to be a good response, the system parameters may be set or adjusted according to the parameters stored in the lookup table 892. If the prior patient response was considered to not to be similar 882 or good 884, a default table may be consulted 888 which contains non-patient specific system parameters that would generally be considered suitable in general circumstances or that would be considered suitable for a patient presenting with the current physiological parameters. The system parameters may then be set or adjusted according to the parameters stored in the default table 890.

It will be understood that prior patient negative responses (e.g., "less effective", "least effective to date") may be stored in a lookup table, accessed and used in a similar manner to that described with regard to the "good" responses in FIG. 25. In some embodiments, separate lookup tables are maintained for "more effective" responses (e.g., an "increased effectiveness" data table) and for "less effective responses" (e.g., a "decreased effectiveness" data table). In some embodiments, the "increased effectiveness" lookup table and the "decreased effectiveness" lookup table are the same data table, which stores patient parameters and associated system parameters that resulted in "more effective", "most effective", "less effective" or "least effective" patient parameters. As discussed above, lookup tables may include information regarding patient data obtained within a session or between sessions.

Figure 26:
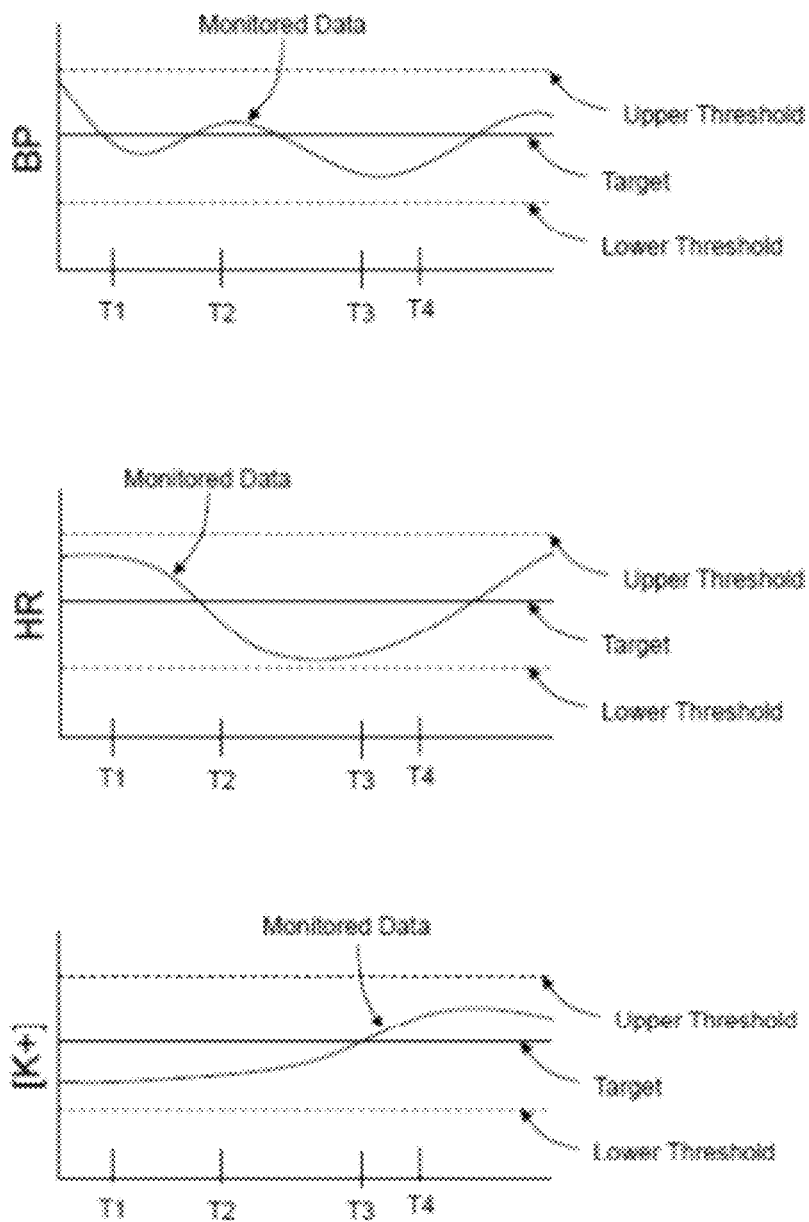
FIG. 26 shows a schematic graphical representation of monitored prophetic data shown for purposes of illustration.

For purposes of example and to provide some clarity with regard to how one (or a blood fluid removal or dialysis system or monitoring system) can determine whether patient parameter data is "out of range", "more effective", "less effective", and the like (e.g., as discussed above with regard to FIGS. 22-24), graphical schematic data is presented in FIG. 26 showing representations of monitored data (not actual data) for blood pressure (BP), heart rate (HR), and potassium concentration in the patient's blood ([$K^+$]). In the schematic illustration, a blood fluid removal session is initiated at T1 and is ended at T4. System parameters are changed at times T2 and T3. The patient parameters (BP, HR, [$K^+$]) are shown as changing in response to the changes in blood fluid removal system parameters and continuing to change after the session ends. As shown, not all patient parameters will respond similarly (e.g., more effective or less effective) in response to a system parameter change or session. In the depicted schematic illustrations, a desired target value is shown for each patient parameter. If the monitored data value achieves or approaches the target, a determination may be made that the change in system parameter or an overall session resulted in an increased effectiveness or "more effective" state for that parameter. If the monitored data value deviates from the target, a determination may be made that the change in system parameter or overall session parameters resulted in a decreased effectiveness or "less effective" state for that parameter. It will be understood that the timing of the patient parameter response to a change in system parameters may vary greatly from patient parameter to patient parameter. In some cases, changes in a patient parameter may be observed within seconds or minutes of a change in a system parameter. In other cases, a change in a patient parameter in response to a change in a system parameter may take hours or more to be fully appreciated or observed.

In the graphical depictions of the represented monitored data presented in FIG. 27, a lower threshold value and an upper threshold value are depicted by horizontal dashed lines. If the monitored data for a patient parameter exceeds the upper threshold value or crosses below the lower threshold value, a determination may be made that the value for that parameter is "out of range."

It will be understood that the condition of a patient may deteriorate with time, which is typical of patients having chronic kidney disease. Accordingly, the targets and upper and lower thresholds may vary with time. These targets and thresholds may be modified by input from, for example, a healthcare provider from time to time based on, e.g., the patient's health or status of patient parameters. Alternatively, the system may automatically adjust target or threshold values over time based on population data or based on data of a particular patient indicative of a generally deteriorating condition. If the target or thresholds are adjusted to or near predetermined cutoff values, an alert may be issued to that effect.

Further, target and threshold values for one or more parameters can be modified on a session-by-session basis. For example, if the patient is excessively fluid overloaded prior to a given session, the target or threshold tissue fluid levels may be adjusted upward for the next or current session. The negative consequences of too much fluid removal in one session or at too fast of a rate may outweigh the negative consequences of higher fluid levels remaining in the patient. Additional or more frequent fluid removal sessions may be employed to return the patient to more desirable fluid levels.

As shown in the examples presented in FIG. 26, the patient parameters change over time. In embodiments, values of one or more patient parameters are averaged over a period of time to account for fluctuations that may occur. The averaged value may be compared to the target and thresholds for determining whether a patient is improving. By averaging values over time, the effect of an anomalous value that may deviate significantly from the target value or may be out of bounds may be diminished. Of course, thresholds may be set for single occurrences, for example if the values of those occurrences may present an imminent health concern to the patient. In embodiments, the presence a single occurrence that deviates significantly from other recent occurrences may result in activation of a subroutine or monitoring method for detecting similar subsequent deviations. In embodiments, consecutive significant deviations, a percent of significant deviations within a given number of samples, or the like, may result in activation or an alert or alarm.

Additional examples of systems and teachings useful in practicing the above embodiments can be found in, for example, U.S. Provisional Patent Application No. 61/480, 532, filed on Apr. 29, 2011, and U.S. patent application Ser. No. 13/424,479 filed Mar. 20, 2012, both entitled ELECTROLYTE AND pH MONITORING FOR FLUID REMOVAL PROCESSES, U.S. patent application Ser. No. 13/424,429 filed Mar. 20, 2012, entitled INTERSESSION MONITORING FOR BLOOD FLUID REMOVAL THERAPY, and U.S. Provisional Patent Application No. 61/480,544, filed on Apr. 29, 2011, and U.S. patent application Ser. No. 13/424,525 filed Mar. 20, 2012, both entitled CHRONIC pH OR ELECTROLYTE MONITORING, all which applications are hereby incorporated herein by reference in their entirety to the extent that they do not conflict with the present disclosure.

The particular embodiments disclosed above are illustrative only, as the invention may be modified and practiced in different but equivalent manners apparent to those skilled in the art having the benefit of the teachings provided herein. Furthermore, no limitations are intended with respect to the details of construction or the design shown herein, other than as described in the claims below. It is therefore evident that the particular embodiments disclose above may be altered or modified and that all such variations are considered to be within the scope and spirit of the present invention.

We claim:

1. A medical monitor, comprising:
   a medical device for determining body potassium status by monitoring electrical signals of the body of a subject;
   a processor for applying a forward computational procedure to the electrical signals monitored from the body in communication with the medical device; and
   a communication system indicating a condition of hyperkalemia, hypokalemia or arrhythmia of the subject based on at least one risk score;
   wherein the medical device associates a cardiac cycle of the subject with a time index and calculates the at least one risk score, wherein the at least one risk score is associated with the time index;
   wherein the at least one risk score is calculated by the forward computational procedure by the addition of a plurality of features converted to scalar feature scores on a common scale, wherein the addition of the feature scores can be weighted or non-weighted as provided in Equation 4:
   Risk Score=

$$\Sigma_{k=1}^{n} W_k * P_k \quad \text{(Eq. 4)}$$

wherein $W_k$ is a weighting factor, $P_k$ is a feature score, k is a feature number, and n is a number of features; and wherein the addition of the features scores is non-weighted when $W_k=1$;
   wherein the processor is configured to receive clinical information regarding the physiological state of the subject associated with the time index and makes an adjustment to the forward computational procedure based upon an error between the at least one risk score and the clinical information, and wherein the adjustment to the forward computational procedure based upon an error between the at least one risk score and the clinical information is done by the processor using a backward computational procedure, wherein the backward computational procedure adjusts exponential factors used to calculate the scalar feature score.

2. The medical monitor of claim 1, wherein the medical device is implantable in the subject.

3. The medical monitor of claim 1, wherein the medical device is an external device comprising a plurality of electrodes for placement on the skin of the subject.

4. The medical monitor of claim 1, wherein the processor identifies a plurality of features of the cardiac cycle and compares the plurality of features to determinant values to calculate the at least one risk score using the forward computational procedure.

5. The medical monitor of claim 4, wherein the plurality of features includes one or more selected from the group consisting of P-R interval, QRS width, Q-T interval, QT-dispersion, P-wave amplitude, P-wave peak, S-T segment depression, T-wave inversion, U-wave amplitude, T-wave peak amplitude, and heart rate variability.

6. The medical monitor of claim 4, wherein a first risk score is calculated for a time index by applying a first forward computational procedure to one or more of the features of P-R interval, S-T segment depression, T-wave inversion and U-wave amplitude, wherein the processor increases a first alert counter by an incremental amount for each time index where the first risk score exceeds a predetermined risk score threshold and an alert is issued when the first alert counter exceeds a predetermined alert threshold.

7. The medical monitor of claim 6, wherein the predetermined risk score threshold is determined based upon a baseline risk score value of the subject.

8. The medical monitor of claim 6, wherein the first alert counter is increased for each consecutive time index where the first risk score exceeds the predetermined risk score threshold.

9. The medical monitor of claim 8, wherein the predetermined risk score threshold is determined based upon a baseline risk score value of the subject.

10. The medical monitor of claim 6, wherein the first alert counter is periodically reset if a sufficient number of time indices where the first risk score exceeds the predetermined risk score threshold is not observed over a time period.

11. The medical monitor of claim 10, wherein the predetermined risk score threshold is determined based upon a baseline risk score value of the subject.

12. The medical monitor of claim 6, wherein the first forward computational procedure determines a non-weighted or weighted sum of feature scores P1, P6, P7, P8 and P10 to calculate the first risk score and the feature scores are assigned a zero or non-zero value based on the following:
    P1 based upon the feature P-R interval in time units,
    P6 based upon the feature of depression of the S-T segment,
    P7 based upon the feature of inversion of the T-wave,
    P8 based upon the feature of U-wave amplitude in potential units, and
    P10 is heart rate variation in time units.

13. The medical monitor of claim 4, wherein at least one feature is monitored at a first time index and at a second time index defining a curve, wherein the processor increases an alert when the area under the curve exceeds a predetermined threshold.

14. The medical monitor of claim 4, wherein the plurality of features includes one or more selected from the group consisting of QRS width, Q-T interval, P-wave amplitude, P-wave peak, T-wave amplitude and heart rate variation, and wherein a second risk score is calculated for a time index by applying a second forward computational procedure to the features of QRS width, Q-T interval, P-wave amplitude, P-wave peak, T-wave amplitude, and heart rate variation.

15. The medical monitor of claim 14, wherein the second forward computational procedure determines a non-weighted or weighted sum of feature scores P2, P3, P4, P5, P9 and P10 and feature scores are assigned a zero or non-zero value based on the following:
- P2 based upon the feature QRS width in time units,
- P3 based upon the feature Q-T interval in time units,
- P4 based upon the feature P-wave amplitude in potential units per time unit,
- P5 based upon the feature P-wave peak in potential units,
- P9 based upon the feature of T-wave amplitude in potential units and,
- P10 is heart rate variation in time units.

16. The medical monitor of claim 4, wherein a third risk score is calculated for a time index by applying a third forward computational procedure to one or more of the features of P-R interval, QRS width, Q-T interval, P-wave amplitude, P-wave peak, S-T segment, T-wave inversion, U-wave amplitude, T-wave peak amplitude, and heart rate variability.

17. The medical monitor of claim 16, wherein the third forward computational procedure determines a non-weighted or weighted sum of feature scores P1 through P10 and feature scores are assigned a zero or non-zero value based on the following:
- P1 based upon the feature P-R interval in time units,
- P2 based upon the feature QRS width in time units,
- P3 based upon the feature Q-T interval in time units,
- P4 based upon the feature P-wave amplitude in potential units per time unit,
- P5 based upon the feature P-wave peak in potential units,
- P6 based upon the feature of depression of the S-T segment,
- P7 based upon the feature of inversion of the T-wave,
- P8 based upon the feature of U-wave amplitude in potential units,
- P9 based upon the feature of T-wave amplitude in potential units, and
- P10 is heart rate variation in time units.

18. The medical monitor of claim 17, wherein the backward computational procedure adjusts one or more selected from the determinant values $X_C$, weighting factors $W_k$ and an exponential factor k.

19. The medical monitor of claim 1, wherein the feature value $P_k$ has a value of 0 or 1 or another integer value as determined by applying a discrete function to a corresponding feature of the cardiac function.

20. The medical monitor of claim 1, wherein the feature value $P_k$ can have a non-integer value.

21. The medical monitor of claim 1, wherein the backward computational procedure adjusts weighting factors $W_k$.

22. The medical monitor of claim 1, wherein the backward computational procedure adjusts determinant values to calculate the risk score and feature scores $P_k$.

23. The medical monitor of claim 1, wherein the feature score $P_k$ is determined by any one of the following computational procedures where x is a feature extracted from the electrical signals, $x_c$ is a determinant value, and k is an exponential factor:

$$D_1(x, x_C) = \begin{cases} 1, & x > x_C \\ 0, & x \leq x_C \end{cases},$$

$$D_2(x, x_C) = \begin{cases} 0, & x > x_C \\ 1, & x \leq x_C \end{cases},$$

$$D_3(x, x_C) = \begin{cases} 1, & |x| > x_C \\ 0, & |x| \leq x_C \end{cases},$$

$$S_1(x, x_C, k) = \frac{1}{1 + e^{k(x_C - x)}},$$

$$S_2(x, x_C, k) = \frac{1}{1 + e^{k(x - x_C)}}, \text{ and}$$

$$S_3(x, x_C, k) = \frac{1}{1 + e^{k\left(\frac{3}{2}x_C - x\right)}} + \frac{1}{1 + e^{k\left(x - \frac{x_C}{2}\right)}}.$$

24. The medical monitor of claim 1, wherein the communication system indicates a condition of hyperkalemia or hypokalemia of the subject.

25. The medical monitor of claim 1, wherein the feature score $P_k$ is determined by any one of the following computational procedures where x is a feature extracted from the electrical signals, $x_c$ is a determinant value, and k is an exponential factor:

$$S1(x, x_c, k) = \frac{1}{1 + e^{k(x_c - x)}},$$

$$S2(x, x_c, k) = \frac{1}{1 + e^{k(x - x_c)}}, \text{ and}$$

$$S3(x, x_c, k) = \frac{1}{1 + e^{k\left(\frac{3}{2}x_c - x\right)}} + \frac{1}{1 + e^{k\left(x - \frac{x_c}{2}\right)}}.$$

* * * * *